US011453723B1

(12) United States Patent
Bramson et al.

(10) Patent No.: US 11,453,723 B1
(45) Date of Patent: Sep. 27, 2022

(54) BCMA T CELL-ANTIGEN COUPLERS AND USES THEREOF

(71) Applicant: McMaster University, Hamilton (CA)

(72) Inventors: Jonathan Lorne Bramson, Oakville (CA); Joanne Alicia Hammill, Hamilton (CA); Christopher W. Helsen, Oakville (CA)

(73) Assignee: McMaster University, Hamilton (CA)

( * ) Notice: Subject to any disclaimer, the term of this patent is extended or adjusted under 35 U.S.C. 154(b) by 0 days.

(21) Appl. No.: 17/304,924

(22) Filed: Jun. 28, 2021

Related U.S. Application Data

(60) Provisional application No. 63/202,839, filed on Jun. 25, 2021.

(51) Int. Cl.
| | |
|---|---|
| *C07K 16/28* | (2006.01) |
| *C07K 14/73* | (2006.01) |
| *A61K 35/17* | (2015.01) |
| *A61P 35/00* | (2006.01) |
| *A61K 39/00* | (2006.01) |

(52) U.S. Cl.
CPC .......... *C07K 16/2878* (2013.01); *A61K 35/17* (2013.01); *A61P 35/00* (2018.01); *C07K 14/70514* (2013.01); *C07K 16/2809* (2013.01); *A61K 2039/505* (2013.01); *C07K 2317/622* (2013.01); *C07K 2319/00* (2013.01)

(58) Field of Classification Search
None
See application file for complete search history.

(56) References Cited

U.S. PATENT DOCUMENTS

| | | | |
|---|---|---|---|
| 7,083,785 B2 | 8/2006 | Browning et al. | |
| 7,947,805 B2 | 5/2011 | Belloir et al. | |
| 8,084,030 B2 | 12/2011 | Kalled et al. | |
| 9,718,893 B2 | 8/2017 | Jung et al. | |
| 10,435,453 B2 | 10/2019 | Bramson et al. | |
| 10,640,562 B2 | 5/2020 | Bramson et al. | |
| 10,822,408 B2 | 11/2020 | Hamburger et al. | |
| 11,001,621 B1 | 5/2021 | Bramson et al. | |
| 11,008,376 B2 | 5/2021 | Bramson et al. | |
| 11,110,123 B2 | 9/2021 | Bramson et al. | |
| 11,111,298 B2 * | 9/2021 | Bramson | C07K 14/70514 |
| 11,198,737 B2 | 12/2021 | Helsen et al. | |
| 2002/0081296 A1 | 6/2002 | Theill et al. | |
| 2002/0107869 A1 | 8/2002 | Leroy | |
| 2003/0012783 A1 | 1/2003 | Kindsvogel | |
| 2003/0095967 A1 | 5/2003 | MacKay et al. | |
| 2004/0162411 A1 | 8/2004 | Lanzavecchia | |
| 2006/0233791 A1 | 10/2006 | Tedder et al. | |
| 2007/0048221 A1 | 3/2007 | Kindsvogel | |
| 2007/0048319 A1 | 3/2007 | Kindsvogel | |
| 2007/0049735 A1 | 3/2007 | Kindsvogel | |
| 2008/0044413 A1 | 2/2008 | Hammond et al. | |
| 2008/0095766 A1 | 4/2008 | Koenig et al. | |
| 2008/0260737 A1 | 10/2008 | Ponce et al. | |
| 2008/0267965 A1 | 10/2008 | Kalled et al. | |
| 2012/0082661 A1 | 4/2012 | Kalled et al. | |
| 2012/0213768 A1 | 8/2012 | Oh et al. | |
| 2013/0101599 A1 | 4/2013 | Borges et al. | |
| 2013/0156770 A1 | 6/2013 | Kufer et al. | |
| 2013/0273055 A1 | 10/2013 | Borges et al. | |
| 2013/0280280 A1 | 10/2013 | Algate et al. | |
| 2013/0330323 A1 | 12/2013 | Dunn et al. | |
| 2015/0119555 A1 | 4/2015 | Jung et al. | |
| 2015/0322169 A1 | 11/2015 | June et al. | |
| 2016/0228546 A1 | 8/2016 | Stagliano et al. | |
| 2016/0362472 A1 | 12/2016 | Bitter et al. | |
| 2016/0368964 A1 | 12/2016 | Bramson et al. | |
| 2019/0153115 A1 | 5/2019 | Schellenberger et al. | |
| 2020/0024345 A1 | 1/2020 | Bramson et al. | |
| 2020/0071377 A1 | 3/2020 | Bramson et al. | |
| 2020/0239571 A1 | 7/2020 | Bramson et al. | |
| 2020/0261500 A1 | 8/2020 | Bramson et al. | |
| 2020/0270330 A1 | 8/2020 | Bramson et al. | |
| 2020/0308278 A1 | 10/2020 | Bramson et al. | |
| 2020/0392247 A1 | 12/2020 | Helsen et al. | |
| 2021/0369780 A1 | 12/2021 | Bramson et al. | |

FOREIGN PATENT DOCUMENTS

| | | |
|---|---|---|
| WO | WO-9957268 A1 | 11/1999 |
| WO | WO-2004106380 A2 | 12/2004 |
| WO | WO-2005040220 A1 | 5/2005 |
| WO | WO-2010037835 A2 | 4/2010 |
| WO | WO-2012066058 A1 | 5/2012 |
| WO | WO-2012163805 A1 | 12/2012 |
| WO | WO-2013092001 A1 | 6/2013 |
| WO | WO-2013123061 A1 | 8/2013 |
| WO | WO-2013132268 A1 | 9/2013 |
| WO | WO-2014011988 A2 | 1/2014 |

(Continued)

OTHER PUBLICATIONS

Acuto et al. T cell activation and the cytoskeleton. Annu. Rev. Immunol. 18:165-184 (2000).
Alabanza et al. Function of Novel Anti-CD19 Chimeric Antigen Receptors with Human Variable Regions Is Affected by Hinge and Transmembrane Domains. Mol Ther25(11):2452-2465 (2017).
Anderson et al. Comodulation of CD3 and CD4. Evidence for a specific association between CD4 and approximately 5% of the CD3:T cell receptor complexes on helper T lymphocytes. J Immunol 140:1732-1737 (1988).
Apuri, S., et al., "Outcomes in Patients with Acute Myeloid Leukemia Preceded by Breast Cancer", Blood, 120(21): 4316 (2012).
Arcaro et al. Essential role of CD8 palmitoylation in CD8 coreceptor function. J. Immunol. 165:2068-2076 (2000).
Chames et al. Bispecific antibodies for cancer therapy: the light at the end of the tunnel? MAbs 1:539-547 (2009).

(Continued)

*Primary Examiner* — Zachary S Skelding
(74) *Attorney, Agent, or Firm* — Goodwin Procter LLP

(57) ABSTRACT

BCMA T cell antigen coupler (TAC) polypeptides having (i) an antigen-binding domain that binds BCMA, (ii) an antigen-binding domain that binds a protein associated with a TCR complex, and (iii) a T cell receptor signaling domain polypeptide are provided.

15 Claims, 10 Drawing Sheets
Specification includes a Sequence Listing.

(56) References Cited

FOREIGN PATENT DOCUMENTS

| WO | WO-2014122144 A1 | 8/2014 |
|---|---|---|
| WO | WO-2015006749 A2 | 1/2015 |
| WO | WO-2015117229 A1 | 8/2015 |
| WO | WO-2016166139 A1 | 10/2016 |
| WO | WO-2017040344 A2 | 3/2017 |
| WO | WO-2017087723 A1 | 5/2017 |
| WO | WO-2018027155 A1 | 2/2018 |
| WO | WO-2018121605 A1 | 7/2018 |
| WO | WO-2019071358 A1 | 4/2019 |
| WO | WO-2020018727 A1 | 1/2020 |

OTHER PUBLICATIONS

Chervin et al. The impact of TCR-binding properties and antigen presentation format on T cell responsiveness. J. Immunol. 183:1166-1178 (2009).
Compte et al. Inhibition of tumor growth in vivo by in situ secretion of bispecific anti-CEA x anti-CD3 diabodies from lentivirally transduced human lymphocytes. Cancer Gene Therapy 14:380-388 (2007).
Deans et al. Interaction of CD4:lck with the T cell receptor/CD3 complex induces early signaling events in the absence of CD45 tyrosine phosphatase. Eur J Immunol 22:661-668 (1992).
Dotti et al. Fifteen years of gene therapy based on chimeric antigen receptors: "are we nearly there yet?" Hum. Gene Ther. 20:1229-1239 (2009).
EP15746948.7 Communication pursuant to Rule 114(2) EPC dated Jan. 21, 2019.
Finney et al. Activation of resting human primary T cells with chimeric receptors: costimulation from CD28, inducible costimulator, CD134, and CD137 in series with signals from the TCR zeta chain. J. Immunol. 172:104-113 (2004).
Fournier et al. Bispecific antibodies and trispecific immunocytokines for targeting the immune system against cancer: preparing for the future. BioDrugs 27:35-53 (2013).
Fragoso et al. Lipid raft distribution of CD4 depends on its palmitoylation and association with Lck, and evidence for CD4-induced lipid raft aggregation as an additional mechanism to enhance CD3 signaling. J. Immunol. 170:913-921 (2003).
Frankel et al. Targeting T cells to tumor cells using bispecific antibodies. Curr Opin Chem Biol 17(3):385-392 (2013).
Fry et al. T-cell adoptive immunotherapy for acute lymphoblastic leukemia. Hematology Am. Soc. Hematol. Educ. Program 2013:348-353 (2013).
Geiger et al. Integrated src kinase and costimulatory activity enhances signal transduction through single-chain chimeric receptors in T lymphocytes. Blood 98(8):2364-2371 (2001).
Geyer et al. Review: Current clinical applications of chimeric antigen receptor (CAR) modified T cells. Cytotherapy 18(11):1393-1409 (2016).
Hammond et al. Selective targeting and potent control of tumor growth using an EphA2/CD3-Bispecific single-chain antibody construct. 67(8):3927-3935 (2007).
Han et al. Chimeric antigen receptor-engineered T cells for cancer immunotherapy: progress and challenges. J. Hematol. Oncol. 6:4 7 (2013).
He et al. T-cell antigen receptor triggering and lipid rafts: a matter of space and time scales. Talking Point on the involvement of lipid rafts in T-cell activation. EMBO Rep. 9:525-530 (2008).
Helsen et al. The chimeric TAC receptor co-opts the T cell receptor yielding robust anti-tumor activity without toxicity. Nature Communications 9:3049 (2018).
Helsen et al. Tri-functional T cell receptor antigen coupler (Tri-TAC): a novel methodto direct T cells against tumors. J Immunother Cancer 2(Supp 3):p. 17 (2014).
Hexham et al. Optimization of the anti-(human CD3) immunotoxin DT389-scFv(UCHT1) N-terminal sequence to yield a homogeneous protein. Biotechnol Appl Biochem 34(Pt 3):183-187 (2010).

Humphries. Adoptive cell therapy: Honing that killer instinct. Nature 504:S13-15 (2013).
Itano et al. The cytoplasmic domain of CD4 promotes the development of CD4 lineage T cells. J Exp Med. 183(3)731-741 (1996).
Jamal, S., et al., "Immunophenotypic Analysis of Peripheral T-Cell Neoplasms", Am. J. Clin. Pathol., vol. 116, pp. 512-526, (2001).
Kiewe, P., et al., "Phase I Trial of the Trifunctional Anti-HER2 x Anti-CD3 Antibody Ertumaxomab in Matastatic Breast Cancer", Clin. Cancer Res., 12(10), pp. 3085-3091, (2006).
Kim et al. A zinc clasp structure tethers Lck to T cell coreceptors CD4 and CD8. Science 301:1725-1728 (2003).
Kimchi-Sarfaty, C., et al., "A 'silent' polymorphiosm in the MDR1 gene changes substrate specificity", Science, 315:525-528, (2007).
Klinger et al. Harnessing T cells to fight cancer with BiTE® antibody constructs—past developments and future directions. Immunol Rev. 270(1):193-208 (2016).
Kochenderfer et al. Treating B-cell cancer with T cells expressing anti-CD19 chimeric antigen receptors. Nat. Rev. Clin. Oncol. 10:267-276 (2013).
Kuhns et al. TCR Signaling Emerges from the Sum of Many Parts. Front. Immunol. 3:159 (2012).
Löffler et al. A recombinant bispecific single-chain antibody, CD19 X CD3, induces rapid and high lymphoma-directed cytotoxicity by unstimulated T lymphocytes. Blood 95(6):2098-2103 (2000).
Methi et al. Short-interfering RNA-mediated Lck knockdown results in augmented downstream T cell responses. J. Immunol. 175(11):7398-7406 (2005).
Milone et al. Chimeric receptors containing CD137 signal transduction domains mediate enhanced survival of T cells and increased antileukemic efficacy in vivo. Mol. Ther. 17: 1453-1464 (2009).
Molhoj, et al. CD19-/CD3-bispecific antibody of the BiTE class is far superior to tandem diabody with respect to redirected tumor cell lysis. Mol Immunol. Mar. 2007;44(8):1935-43. Epub Nov. 2, 2006.
Nagorsen et al. Immunomodulatory therapy of cancer with T cell-engaging BiTE antibody blinatumomab. Exp Cell Res 317(9):1255-1260 (2011).
Nagorsen et al. Immunotherapy of lymphoma and leukemia with T-cell engaging BiTE antibody blinatumomab. Leuk Lymph 50(6): 886-891 (2009).
Panka et al. Variable region framework differences result in decreased or increased affinity of variant anti-digoxin antibodies. PNAS USA 85:3080-3084 (1988).
PCT/CA2015/000068 International Preliminary Report on Patentability dated Aug. 9, 2016.
PCT/CA2015/000068 International Search Report and Written Opinion dated May 4, 2015.
PCT/CA2018/051290 International Search Report and Written Opinion dated Jan. 17, 2019.
PCT/US2019/042297 International Search Report and Written Opinion dated Oct. 30, 2019.
Pllozzi et al. Co-expression of CD79a (JCB117) and CD3 by lymphoblastic lymphoma. J Pathol 186(2):140-143. (1998).
Popik, et al. CD4 receptor localized to non-raft membrane microdomains supports HIV-1 entry. Identification of a novel raft localization marker in CD4. J Biol Chem 279(1):704-712 (2004).
Portell et al. Clinical and pharmacologic aspects of blinatumomab in the treatment of B-cell acute lymphoblastic leukemia. Clin. Pharmacol. 5(Suppl 1):5-11 (2013).
Rosenberg, et al. Use of tumor-infiltrating lymphocytes and interleukin-2 in the immunotherapy of patients with matastatic melanoma. A preliminary report. NEJM 319: 1676 (1988).
Rudikoff et al. Single amino acid substitution altering antigen-binding specificity. PNAS USA 79:1979-1983 (1982).
Thompson et al. CLUSTAL W: improving the sensitivity of progressive multiple sequence alignment through sequence weighting, position-specific gap penalties and weight matrix choice. Nucleic Acid Res. 22:4673-4680 (1994).
Till et al. CD20-specific adoptive immunotherapy for lymphoma using a chimeric antigen receptor with both CD28 and 4-1 BB domains: pilot clinical trial results. Blood 119(17):3940-3950 (2012).
U.S. Appl. No. 17/301,884, filed Apr. 16, 2021.
U.S. Appl. No. 15/117,173 Office Action dated Jan. 24, 2018.
U.S. Appl. No. 15/117,173 Office Action dated Jun. 21, 2019.

(56) References Cited

OTHER PUBLICATIONS

U.S. Appl. No. 15/117,173 Office Action dated Oct. 24, 2018.
U.S. Appl. No. 15/929,510 Office Action dated Nov. 9, 2020.
U.S. Appl. No. 15/929,513 Office Action dated May 11, 2021.
U.S. Appl. No. 15/929,513 Office Action dated Nov. 30, 2020.
U.S. Appl. No. 16/442,274 Office Action dated Nov. 6, 2019.
U.S. Appl. No. 16/904,451 Office Action dated Dec. 1, 2020.
U.S. Appl. No. 16/904,451 Office Action dated May 10, 2021.
U.S. Appl. No. 17/248,174 Office Action dated Mar. 11, 2021.
Velasquez. T cells expressing CD19-specific Engager Molecules for the Immunotherapy of CD19-positive Malignancies. Sci Rep 6:27130 (2016).
Voet, D., et al., Biochemistry, John Wiley and Sons, New York, pp. 126-128, (1990).
Wels et al. Construction, Bacterial Expression and Characterization of a Bifunctional Single-Chain Antibody-Phosphatase Fusion Protein Targeted to the human ERBB-2 receptor. Nature Biotech 10: 1128-1132 (1992).
Wittlich et al. Structural characterization of the transmembrane and cytoplasmic domains of human CD4. Biochimica et Biophysica Acta 1768:2949-2960 (2007).
Wykosky, J., et al. The EphA2 repector and ephrinA1 ligand in solid tumors: function and therapeutic targeting, Mol Cancer Res, 6(12):1795-1806 (2008).
Yin et al. Crystal structure of a complete ternary complex of T-cell receptor, peptide-MHC, and CD4. PNAS USA 109:5405-5410 (2012).
Zahnd et al. Efficient Tumor Targeting with High-Affinity Designed Ankyrin Repeat Proteins: Effects of Affinity and Molecular Size. Cancer Res 70: 1595-1605 (2010).
Zahnd et al. Selection and Characterization of Her2 Binding-designed Ankyrin Repeat Proteins. The Journal of Biological Chemistry 281 (46):35167-35175 (2006).
Zhang et al. Sequestration of CD4-associated Lck from the TCR complex may elicit T cell hyporesponsiveness in nonobese diabetic mice. J Immunol 160:1148-1157 (1998).
Zhukovsky et al. Bispecific antibodies and CARs: generalized immunotherapeutics harnessing T cell redirection. Curr Opin Immunol 40:24-35 (2016).
Carpenter, R.O., et al., B-cell maturation antigen is a promising target for adoptive T-cell therapy of multiple myeloma, Clin Cancer Res, 19(8): 2048-2060 (2013).
Chiu, A., et al., Hodgkin lymphoma cells express TACI and BCMA receptors and generate survival and proliferation signals in response to BAFF and APRIL, Blood, 109(2): 729-739 (2007).
De Novo, New Products from R&D Systems, Antibody catalog including BCMA mAB, pp. 1-10 (Mar. 2004).
Deng, S., et al., B-lymphocyte-induced maturation protein 1 up-regulates the expression of B-cell maturation antigen in mouse plasma cells, Mol Biol Rep, 37(8): 3747-3755 (2010).
Deshayes, S., et al., Cell-penetrating peptides: tools for intracellular delivery of therapeutics, Cell Mol Life Sci, 62(16): 1839-1849 (2005).
Guadagnoli, M., et al., Development and characterization of APRIL antagonistic monoclonal antibodies for treatment of B-cell lymphomas, Blood, 117(25): 6856-6865 (2011).
Marsden, H.R., et al., Model systems for membrane fusion, Chem Soc Rev, 40(3): 1572-1585 (2011).
Novak, A.J., et al., Expression of BLyS and its receptors in B-cell non-Hodgkin lymphoma: correlation with disease activity and patient outcome, Blood, 104(8): 2247-2253 (2004).
Ryan, M.C., et al., Antibody targeting of B-cell maturation antigen on malignant plasma cells, Mol Cancer Ther, 6(11): 3009-3018 (2007).
Tai, Y-T., et al., Novel Fc-Engineered Anti-B Cell Maturation Antigen-Monomethyl Auristatin F Antibody-Drug Conjugate (GSK2857916) Induces Potent and Selective Anti-Multiple Myeloma Activity via Enhanced Effector Function and Direct Tumor Cell Killing, Blood, 122(21): 877 (2013).
U.S. Appl. No. 16/547,421 Office Action dated Nov. 24, 2021.
U.S. Appl. No. 17/394,280, filed Aug. 4, 2021.
U.S. Appl. No. 17/394,280 Office Action dated Dec. 10, 2021.
Wang, M., et al., Efficient delivery of genome-editing proteins using bioreducible lipid nanoparticles, PNAS, 113(11): 2868-2873 (2016).
Yong, K. L., et al., Evaluation of BCMA as a Therapeutic Target in Multiple Myeloma Using an Antibody-Drug Conjugate, Blood, 122(21): 4447 (2013).

* cited by examiner

BCMA T CELL-ANTIGEN COUPLERS AND USES THEREOF

CROSS-REFERENCE

This application claims priority to U.S. Provisional Application No. 63/202,839 filed on Jun. 25, 2021, which is incorporated herein by reference in its entirety.

SEQUENCE LISTING

The instant application contains a Sequence Listing which has been submitted electronically in ASCII format and is hereby incorporated by reference in its entirety. Said ASCII copy, created on Jul. 19, 2021, is named TMV_007_SL.txt and is 97,033 bytes in size.

SUMMARY

Disclosed herein, in certain embodiments, are polynucleotides encoding a BCMA (B Cell Maturation Antigen) T cell-antigen coupler (BCMA-TAC) polypeptide. In some embodiments, the polynucleotide comprises a sequence set forth in SEQ ID NO: 68, SEQ ID NO: 70, SEQ ID NO: 72, or SEQ ID NO: 74. In some embodiments, the polynucleotide consists of a sequence set forth in SEQ ID NO: 68, SEQ ID NO: 70, SEQ ID NO: 72, or SEQ ID NO: 74.

Disclosed herein, in certain embodiments, are expression vectors comprising a polynucleotide disclosed herein (e.g., a polynucleotide encoding a BCMA-TAC). In some embodiments, the expression vector comprises a promoter functional in a mammalian cell. In some embodiments, the expression vector is a lentiviral vector, for example, a VSV-G pseudotyped lentiviral vector. In some embodiments, the expression vector is a γ retroviral vector, for example, a GALV pseudotyped γ-retroviral vector.

Disclosed herein, in certain embodiments, are BCMA (B Cell Maturation Antigen) T cell-antigen coupler (BCMA-TAC) polypeptides. In some embodiments, the BCMA-TAC polypeptide comprises a sequence set forth in SEQ ID NO: 67, SEQ ID NO: 69, SEQ ID NO: 71, or SEQ ID NO: 73. In some embodiments, the BCMA-TAC polypeptide consists of a sequence set forth in SEQ ID NO: 67, SEQ ID NO: 69, SEQ ID NO: 71, or SEQ ID NO: 73.

Disclosed herein, in certain embodiments, are T cells comprising a polynucleotide disclosed herein, an expression vector disclosed herein, or a BCMA-TAC polypeptide disclosed herein.

Disclosed herein, in certain embodiments, are pharmaceutical compositions comprising a T cell disclosed herein, and a pharmaceutically acceptable excipient.

Disclosed herein, in certain embodiments, are methods of treating a BCMA-expressing cancer in an individual in need thereof, comprising administering to the individual a T cell or a pharmaceutical composition disclosed herein. In some embodiments, the cancer is a B cell malignancy. In some embodiments, the cancer is selected from the group consisting of: multiple myeloma (MM), B cell lymphoma, acute lymphoblastic leukemia (ALL), chronic lymphocytic leukemia (CLL), Non-Hodgkin lymphoma (NHL), Hodgkin lymphoma, and Waldenstrom's macroglobulinemia. In some embodiments, the cancer is multiple myeloma.

BRIEF DESCRIPTION OF THE DRAWINGS

The invention can be more completely understood with reference to the following drawings.

DETAILED DESCRIPTION

Figure 1:
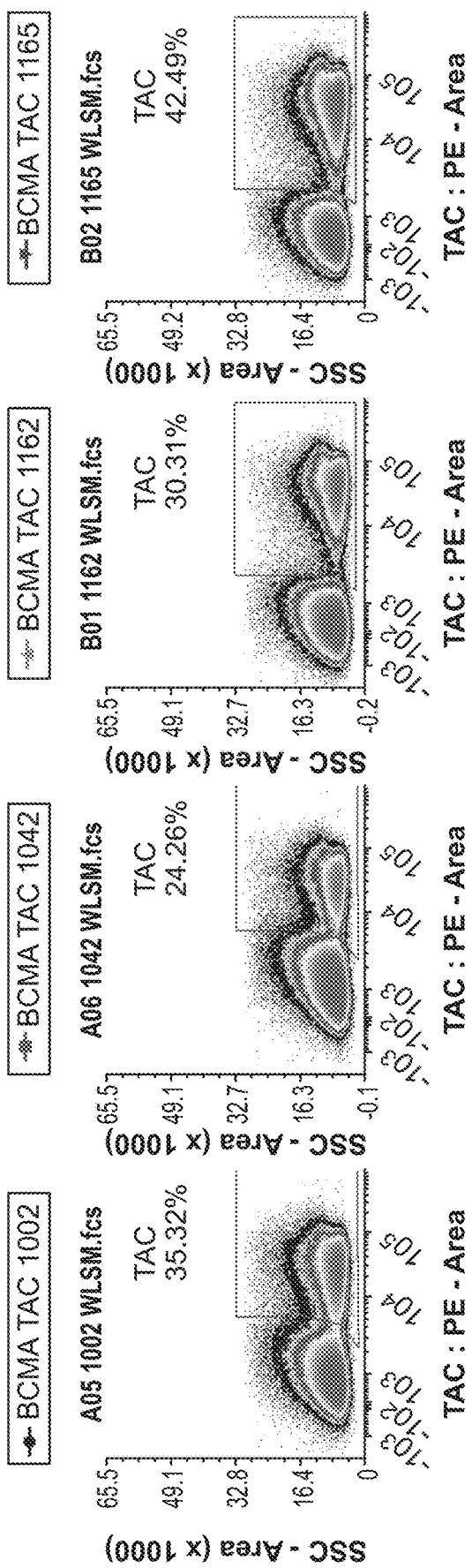
FIG. 1 depicts transduction efficiency for T cells engineered to express the indicated TACs.

Cancer is a major health challenge. According to the American Cancer Society, more than one million people in the United States are diagnosed with cancer each year. While patients with early stage disease are sometimes treated effectively by conventional therapies (surgery, radiation, chemotherapy), few options are available to patients with advanced disease, and those options are typically palliative in nature.

Active immunotherapy seeks to employ the patient's immune system to clear tumors and offers an option to patients who have failed conventional therapies. Generally, this treatment involves infusing patients with large numbers of tumor-specific T cells. This approach has proven to be successful in early phase clinical trials for a number of diseases, including melanoma, myeloma, leukemia, lymphoma and synovial sarcoma. As a specific example, several clinical studies have demonstrated that immunotherapy with T cells are curative in patients with advanced melanoma, confirming the utility of this approach. Additionally, patients suffering from chronic lymphocytic leukemia (CLL) and acute lymphoblastic leukemia (ALL) have also been effectively treated and cured with T cell immunotherapy.

To this point, most engineered T cell therapies involving genetic modification of the T cells yield: (i) forced expression of T cell receptor (TCR); or (ii) a chimeric antigen receptor (CAR) specific for antigen targets on the tumor. To date, the chimeric antigen receptors used for engineering T cells consist of: (i) a targeting domain, usually a single-chain fragment variable (scFv); (ii) a transmembrane domain; and (iii) a cytosolic domain that contains signaling elements from the T cell receptor and associated proteins. Such chimeric antigen receptors have also been referred to as "T-body" or "Chimeric Immune Receptor" (CIR), but currently, most researchers use the term "CAR". One advantage of the CAR approach is that it allows any patient's immune cells to be targeted against any desirable target in a major histocompatibility complex (MHC) independent manner. This is appealing as MHC presentation is often defective in tumor cells.

CARs are considered in modular terms and scientists have spent considerable time investigating the influence of different cytoplasmic signaling domains on CAR function. Conventional CARs generally share two main components: (i) the CD3 zeta cytoplasmic domain, which contains immunotyrosine activation motifs (ITAMs) critical for T cell activation; and (ii) components of costimulatory receptors that trigger important survival pathways such as the Akt pathway.

The first-generation CARs employed a single signaling domain from either CD3ζ or FcεRIγ. Second-generation CARs combined the signaling domain of CD3ζ with the cytoplasmic domain of costimulatory receptors from either the CD28 or TNFR family of receptors. Most CAR-engineered T cells that are currently being tested in the clinic employ second-generation CARs where CD3ζ is coupled to the cytoplasmic domain of either CD28 or CD137. These second generation CARs have demonstrated anti-tumor activity in CD19-positive tumors. Third-generation CARs combined multiple costimulatory domains, but there is concern that third-generation CARs may lose antigen-specificity.

While CAR-engineered T cells have shown considerable promise in clinical application, they rely on a synthetic method for replacing the native activation signal that is provided by the T cell receptor (TCR). Since this synthetic receptor does not deliver all of the signaling components associated with the TCR (ex. ITAMs on CD3γ, CD3δ, CD3ε), it remains unclear whether the T cells are optimally activated by the CAR or how the CAR activation affects T cell differentiation (ex. progression to memory). Furthermore, since the CAR signaling domains are disconnected from their natural regulatory partners by the very nature of the CAR structure, there is an inherent risk that CARs may lead to a low-level of constitutive activation, which could result in off-target toxicities. Therefore, the synthetic nature of the prototypic CAR may disrupt canonical mechanisms that limit TCR activation, and may underpin the severe toxicity often associated with therapeutic doses of conventional CAR T cells.

Given these limitations, it is preferable to re-direct T cells to attack tumors via their natural TCR. An alternate chimeric receptor, termed a T cell Antigen Coupler (TAC or TAC) receptor, has been developed which employs a distinct biology to direct the T cell to attack tumors. While the CAR is a fully synthetic receptor that stitches together components of T cell receptor (TCR) signaling complex, the TAC receptor re-directs the TCR towards tumor targets and recapitulates the native TCR signaling structure. For example, in some embodiments, the TACs disclosed herein activate natural Major Histocompatibility complex (MHC) signaling through the T cell receptor (TCR), while retaining MHC-unrestricted targeting. Further, the TACs disclosed herein recruit the T Cell Receptor (TCR) in combination with co-receptor stimulation. Moreover, in some embodiments, TACs disclosed herein show enhanced activity and safety.

Certain Terminology

The term "antigen-binding domain," refers to any substance or molecule that binds, directly or indirectly, to a target (e.g., BCMA). Antigen-binding domains include antibodies or fragments thereof, peptides, peptidomimetics, proteins, glycoproteins, proteoglycans, carbohydrates, lipids, nucleic acids, or small molecules that bind to a target.

As used herein, unless otherwise indicated, the term "antibody" is understood to mean an intact antibody (e.g., an intact monoclonal antibody), or a fragment thereof, such as a Fc fragment of an antibody (e.g., an Fc fragment of a monoclonal antibody), or an antigen-binding fragment of an antibody (e.g., an antigen-binding fragment of a monoclonal antibody), including an intact antibody, antigen-binding fragment, or Fc fragment that has been modified, engineered, or chemically conjugated. In general, antibodies are multimeric proteins that contain four polypeptide chains. Two of the polypeptide chains are called immunoglobulin heavy chains (H chains), and two of the polypeptide chains are called immunoglobulin light chains (L chains). The immunoglobulin heavy and light chains are connected by an interchain disulfide bond. The immunoglobulin heavy chains are connected by interchain disulfide bonds. A light chain consists of one variable region ($V_L$) and one constant region ($C_L$). The heavy chain consists of one variable region ($V_H$) and at least three constant regions ($CH_1$, $CH_2$ and $CH_3$). The variable regions determine the binding specificity of the antibody. Each variable region contains three hypervariable regions known as complementarity determining regions (CDRs) flanked by four relatively conserved regions known as framework regions (FRs). The extent of the FRs and CDRs has been defined (Kabat, E. A., et al. (1991) SEQUENCES OF PROTEINS OF IMMUNOLOGICAL INTEREST, FIFTH EDITION, U.S. Department of Health and Human Services, NIH Publication No. 91-3242; and Chothia, C. et al. (1987) J. MOL. BIOL. 196:901-917). The three CDRs, referred to as $CDR_1$, $CDR_2$, and $CDR_3$, contribute to the antibody binding specificity. Naturally occurring antibodies have been used as starting material for engineered antibodies, such as chimeric antibodies and humanized antibodies. Examples of antibody-based antigen-binding fragments include Fab, Fab', (Fab')$_2$, Fv, single chain antibodies (e.g., scFv), minibodies, and diabodies. Examples of antibodies that have been modified or engineered include chimeric antibodies, humanized antibodies, and multispecific antibodies (e.g., bispecific antibodies). An example of a chemically conjugated antibody is an antibody conjugated to a toxin moiety.

The term "T cell" as used herein refers to a type of lymphocyte that plays a central role in cell-mediated immunity. T cells, also referred to as T lymphocytes, are distinguished from other lymphocytes, such as B cells and natural killer cells, by the presence of a T-cell receptor (TCR) on the cell surface. There are several subsets of T cells with distinct functions, including but not limited to, T helper cells, cytotoxic T cells, memory T cells, regulatory T cells and natural killer T cells.

The term "γδ T cell" or "gamma delta T cell" or "gd T cell" as used herein refers to any lymphocyte having a γδ T cell receptor (TCR) on its surface, including one γ-chain and one δ-chain.

The term "T cell antigen coupler" or TAC is used interchangeably with "trifunctional T cell antigen coupler" or Tri-TAC and refers to an engineered nucleic acid construct or polypeptide comprising (a) an antigen-binding domain that binds a target, (b) an antigen-binding domain that binds a protein associated with a T cell receptor (TCR) complex, and (c) a T cell receptor signaling domain.

The term "polynucleotide" and/or "nucleic acid sequence" and/or "nucleic acid" as used herein refers to a sequence of nucleoside or nucleotide monomers consisting of bases, sugars and intersugar (backbone) linkages. The term also includes modified or substituted sequences comprising non-naturally occurring monomers or portions thereof. The nucleic acid sequences of the present application may be deoxyribonucleic acid sequences (DNA) or ribonucleic acid sequences (RNA) and may include naturally occurring bases including adenine, guanine, cytosine, thymidine and uracil. The sequences may also contain modified bases. Examples of such modified bases include aza and deaza adenine, guanine, cytosine, thymidine and uracil; and xanthine and hypoxanthine. The nucleic acids of the present disclosure may be isolated from biological organisms, formed by laboratory methods of genetic recombination or obtained by chemical synthesis or other known protocols for creating nucleic acids.

The term "isolated polynucleotide" or "isolated nucleic acid sequence" as used herein refers to a nucleic acid substantially free of cellular material or culture medium when produced by recombinant DNA techniques, or chemical precursors, or other chemicals when chemically synthesized. An isolated nucleic acid is also substantially free of sequences which naturally flank the nucleic acid (i.e. sequences located at the 5' and 3' ends of the nucleic acid) from which the nucleic acid is derived. The term "nucleic acid" is intended to include DNA and RNA and is either double stranded or single stranded, and represents the sense or antisense strand. Further, the term "nucleic acid" includes the complementary nucleic acid sequences.

The term "recombinant nucleic acid" or "engineered nucleic acid" as used herein refers to a nucleic acid or polynucleotide that is not found in a biological organism. For example, recombinant nucleic acids may be formed by laboratory methods of genetic recombination (such as molecular cloning) to create sequences that would not otherwise be found in nature. Recombinant nucleic acids may also be created by chemical synthesis or other known protocols for creating nucleic acids.

The terms "peptide", "polypeptide," and "protein" as used herein mean a chain of amino acids. The term protein as used herein further means a large molecule comprising one or more chains of amino acids and, in some embodiments, is a fragment or domain of a protein or a full length protein. Furthermore, as used herein, the term protein either refers to a linear chain of amino acids or to a chain of amino acids that has been processed and folded into a functional protein. The protein structure is divided into four distinct levels: (1) primary structure—referring to the sequence of amino acids in the polypeptide chain, (2) secondary structure—referring to the regular local sub-structures on the polypeptide backbone chain, such as α-helix and β-sheets, (3) tertiary structure—referring to the three-dimensional structure if monomeric and multimeric protein molecules, and (4) quaternary structure—referring to the three-dimensional structure comprising the aggregation of two or more individual polypeptide chains that operate as a single functional unit. The use of peptide or polypeptide herein does not mean that the chain of amino acids is not also a protein (i.e., a chain of amino acids having a secondary, tertiary or quaternary structure).

The term "isolated polypeptide" refers to a polypeptide substantially free of cellular material or culture medium when produced by recombinant DNA techniques, or chemical precursors or other chemicals when chemically synthesized.

The term "vector" as used herein refers to a polynucleotide that is used to deliver a nucleic acid to the inside of a cell. In some embodiments, a vector is an expression vector comprising expression control sequences (for example, a promoter) operatively linked to a nucleic acid to be expressed in a cell. Vectors known in the art include, but are not limited to, plasmids, phages, cosmids and viruses.

The term "tumor antigen" or "tumor associated antigen" as used herein refers to an antigenic substance produced in tumor cells that triggers an immune response in a host (e.g. which is presented by MHC complexes). In some embodiments, a tumor antigen is on the surface of a tumor cell.

As used herein, the term "transmembrane and cytosolic domain" refers to a polypeptide that comprises a transmembrane domain and a cytosolic domain of a protein associated with the T cell receptor (TCR) complex. In some embodiments, such transmembrane and cytosolic domain may include, but is not limited to, protein domains that (a) associate with the lipid raft and/or (b) bind Lck.

A "TCR co-receptor" as used herein, refers to a molecule that assists the T cell receptor (TCR) in communicating with an antigen-presenting cell and may be considered part of the first signal that leads to the activation of the TCR. Examples of TCR co-receptors include, but are not limited to, CD4, LAG3, and CD8.

A "TCR co-stimulator" or "co-stimulatory domain" as used herein, refers to a molecule that enhances the response of a T cell to an antigen and may be considered as the second signal that leads to the activation of the TCR. Examples of TCR co-stimulators include, but are not limited to, ICOS, CD27, CD28, 4-1BB (CD 137), OX40 (CD134), CD30, CD40, lymphocyte fiction-associated antigen 1 (LFA-1), CD2, CD7, LIGHT, NKG2C, B7-H3, and a ligand that specifically binds CD83.

The terms "recipient", "individual", "subject", "host", and "patient", are used interchangeably herein and in some embodiments, refer to any mammalian subject for whom diagnosis, treatment, or therapy is desired, particularly humans. "Mammal" for purposes of treatment refers to any animal classified as a mammal, including humans, domestic and farm animals, and laboratory, zoo, sports, or pet animals, such as dogs, horses, cats, cows, sheep, goats, pigs, mice, rats, rabbits, guinea pigs, monkeys etc. In some embodiments, the mammal is human. None of these terms require the supervision of medical personnel.

As used herein, the terms "treatment," "treating," and the like, in some embodiments, refer to administering an agent, or carrying out a procedure, for the purposes of obtaining an effect. The effect may be prophylactic in terms of completely or partially preventing a disease or symptom thereof and/or may be therapeutic in terms of affecting a partial or complete cure for a disease and/or symptoms of the disease. "Treatment," as used herein, may include treatment of a disease or disorder (e.g. cancer) in a mammal, particularly in a human, and includes: (a) preventing the disease or a symptom of a disease from occurring in a subject which may be predisposed to the disease but has not yet been diagnosed as having it (e.g., including diseases that may be associated with or caused by a primary disease; (b) inhibiting the disease, i.e., arresting its development; and (c) relieving the disease, i.e., causing regression of the disease. Treating may refer to any indicia of success in the treatment or amelioration or prevention of a cancer, including any objective or subjective parameter such as abatement; remission; diminishing of symptoms; or making the disease condition more tolerable to the patient; slowing in the rate of degeneration or decline; or making the final point of degeneration less debilitating. The treatment or amelioration of symptoms is based on one or more objective or subjective parameters; including the results of an examination by a physician. Accordingly, the term "treating" includes the administration of the compounds or agents of the present invention to prevent, delay, alleviate, arrest or inhibit development of the symptoms or conditions associated with diseases (e.g. cancer). The term "therapeutic effect" refers to the reduction, elimination, or prevention of the disease, symptoms of the disease, or side effects of the disease in the subject.

As used herein, singular forms "a", "and," and "the" include plural referents unless the context clearly indicates otherwise. Thus, for example, reference to "an antibody" includes a plurality of antibodies and reference to "an antibody" in some embodiments includes multiple antibodies, and so forth.

As used herein, all numerical values or numerical ranges include whole integers within or encompassing such ranges and fractions of the values or the integers within or encompassing ranges unless the context clearly indicates otherwise. Thus, for example, reference to a range of 90-100%, includes 91%, 92%, 93%, 94%, 95%, 95%, 96%, 97%, etc., as well as 91.1%, 91.2%, 91.3%, 91.4%, 91.5%, etc., 92.1%, 92.2%, 92.3%, 92.4%, 92.5%, etc., and so forth. In another example, reference to a range of 1-5,000 fold includes 1, 2, 3, 4, 5, 6, 7, 8, 9, 10, 11, 12, 13, 14, 15, 16, 17, 18, 19, 20, fold, etc., as well as 1.1, 1.2, 1.3, 1.4, 1.5, fold, etc., 2.1, 2.2, 2.3, 2.4, 2.5, fold, etc., and so forth.

"About" a number, as used herein, refers to range including the number and ranging from 10% below that number to 10% above that number. "About" a range refers to 10% below the lower limit of the range, spanning to 10% above the upper limit of the range.

"Percent (%) identity" refers to the extent to which two sequences (nucleotide or amino acid) have the same residue at the same positions in an alignment. For example, "an amino acid sequence is X % identical to SEQ ID NO: Y" refers to % identity of the amino acid sequence to SEQ ID NO: Y and is elaborated as X % of residues in the amino acid sequence are identical to the residues of sequence disclosed in SEQ ID NO: Y. Generally, computer programs are employed for such calculations. Exemplary programs that compare and align pairs of sequences, include ALIGN (Myers and Miller, 1988), FASTA (Pearson and Lipman, 1988; Pearson, 1990) and gapped BLAST (Altschul et al., 1997), BLASTP, BLASTN, or GCG (Devereux et al., 1984).

As used herein, the term "selective binding" refers to the higher affinity with which a molecule (e.g. protein such as an antigen-binding domain of TAC) binds its target molecule (e.g. target antigen such as BCMA) over other molecules. Unless indicated otherwise, the terms "selective binding" and "specific binding" are used interchangeably herein.

T Cell Antigen Couplers (TACs)

Disclosed herein, in certain embodiments, are nucleic acids encoding BCMA T cell-antigen coupler (TAC) polypeptides. In some embodiments, the nucleic acids encoding the BCMA TAC comprise: (a) a first polynucleotide encoding an antigen-binding domain that binds BCMA; (b) a second polynucleotide encoding an antigen-binding domain that binds the TCR complex; and (c) a third polynucleotide encoding a transmembrane domain and cytosolic domain. In some embodiments, the nucleic acids comprise, in order (e.g., from 5' to 3'): (a) the first polynucleotide; (b) the second polynucleotide; and (c) the third polynucleotide encoding a TCR co-receptor cytosolic domain and transmembrane domain. In some embodiments, the nucleic acids encoding the BCMA TAC do not encode a co-stimulatory domain. In some embodiments, the nucleic acids encoding the BCMA TAC do not encode a co-activation domain.

Further disclosed herein, in certain embodiments, are BCMA T cell-antigen coupler (TAC) polypeptides. In some embodiments, the BCMA TAC polypeptides comprise: (a) an antigen-binding domain that binds BCMA; (b) an antigen-binding domain that binds the TCR complex; and (c) a transmembrane domain and cytosolic domain. In some embodiments, the BCMA TAC polypeptides comprise, in order (e.g., from N-terminus to C-terminus) (a) the antigen-binding domain that binds BCMA; (b) the antigen-binding domain that binds the TCR complex; and (c) the transmembrane domain and cytosolic domain. In some embodiments, the BCMA TAC polypeptides do not include a co-stimulatory domain. In some embodiments, the BCMA TAC polypeptides do not include a co-activation domain.

Further disclosed herein, in certain embodiments, are expression vectors comprising a nucleic acid encoding a BCMA TAC polypeptide as described herein.

Further disclosed herein, in certain embodiments, are T cells comprising a nucleic acid encoding a BCMA TAC polypeptide as described herein, T cells comprising an expression vector encoding a BCMA TAC polypeptide as described herein, or T cells comprising a BCMA TAC polypeptide as described herein.

Further disclosed herein, in certain embodiments, are methods of treating a cancer in an individual in need thereof, comprising administering to the individual a T cell comprising a BCMA T cell-antigen coupler (TAC) polypeptide as described herein.

BCMA Antigen-Binding Domain

In certain embodiments, the BCMA TAC polypeptide comprises a BCMA antigen-binding domain. In some embodiments, the BCMA antigen-binding domain selectively binds BCMA. In some embodiments, the BCMA antigen-binding domain binds to BCMA on a target cell. In some embodiments, a target cell is a cell associated with a disease state, including, but not limited to, cancer. In some embodiments, a target cell is a tumor cell.

In some embodiments, the BCMA antigen-binding domain is an antibody or a fragment thereof. In some embodiments, the BCMA antigen-binding domain is selected from single chain antibodies (e.g., single-chain fragment variable antibodies (scFvs)), single domain antibodies (e.g., heavy-chain-only antibodies (VHH), shark heavy-chain-only antibodies (VNAR)), nanobodies, diabodies, minibodies, Fab fragments, Fab' fragments, F(ab')2 fragments, or Fv fragments that bind to BCMA.

In some embodiments, the BCMA antigen-binding domain is selected from ankyrin repeat proteins (DARPins), affibodies, adnectins, affilins, phylomers, fynomers, affimers, peptide aptamers, lectins, knottins, centyrins, anticalins, peptides, peptidomimetics, proteins, glycoproteins, or proteoglycans that bind to BCMA, or naturally occurring ligands for BCMA. In some embodiments, the BCMA antigen-binding domain is a non-protein compound that binds to BCMA, including but not limited to carbohydrates, lipids, nucleic acids, or small molecules.

In some embodiments, the BCMA antigen-binding domain is a designed ankyrin repeat (DARPin) targeted to BCMA. In some embodiments, the BCMA antigen-binding domain is a single-chain variable fragment (ScFv) targeted to BCMA. In some embodiments, the BCMA antigen-binding domain is a nanobody targeted to BCMA.

In some embodiments, the antigen-binding domain that binds BCMA comprises (i) a heavy chain variable region comprising the amino acid sequence of SEQ ID NO: 58 (3625—CDRH1), SEQ ID NO: 59 (3625—CDRH2), and SEQ ID NO: 60 (3625—CDRH3); and (ii) a light chain variable region comprising the amino acid sequence of SEQ ID NO: 53 (3625—CDRL1), SEQ ID NO: 54 (3625—CDRL2), and SEQ ID NO: 55 (3625—CDRL3). In some embodiments, the antigen-binding domain that binds BCMA comprises (i) an amino acid sequence having at least 80% sequence identity with the amino acid sequence of SEQ ID NO: 56 (3625 VL); and (ii) an amino acid sequence having at least 80% sequence identity with the amino acid sequence of SEQ ID NO: 61 (3625 VH). In some embodiments, the antigen-binding domain that binds BCMA comprises (i) an amino acid sequence having at least 85% sequence identity with the amino acid sequence of SEQ ID NO: 56 (3625 VL); and (ii) an amino acid sequence having at least 85% sequence identity with the amino acid sequence of SEQ ID NO: 61 (3625 VH). In some embodiments, the antigen-binding domain that binds BCMA comprises (i) an amino acid sequence having at least 90% sequence identity with the amino acid sequence of SEQ ID NO: 56 (3625 VL); and (ii) an amino acid sequence having at least 90% sequence identity with the amino acid sequence of SEQ ID NO: 61 (3625 VH). In some embodiments, the antigen-binding domain that binds BCMA comprises (i) an amino acid sequence having at least 95% sequence identity with the amino acid sequence of SEQ ID NO: 56 (3625 VL); and (ii) an amino acid sequence having at least 95% sequence identity with the amino acid sequence of SEQ ID NO: 61 (3625 VH). In some embodiments, the antigen-binding domain that binds BCMA comprises (i) an amino acid sequence having at least 96% sequence identity with the amino acid sequence of SEQ ID NO: 56 (3625 VL); and (ii) an amino acid sequence having at least 96% sequence identity with the amino acid sequence of SEQ ID NO: 61 (3625 VH). In some embodiments, the antigen-binding domain that binds BCMA comprises (i) an amino acid sequence having at least 97% sequence identity with the amino acid sequence of SEQ ID NO: 56 (3625 VL); and (ii) an amino acid sequence having at least 97% sequence identity with the amino acid sequence of SEQ ID NO: 61 (3625 VH). In some embodiments, the antigen-binding domain that binds BCMA comprises (i) an amino acid sequence having at least 98% sequence identity with the amino acid sequence of SEQ ID NO: 56 (3625 VL); and (ii) an amino acid sequence having at least 98% sequence identity with the amino acid sequence of SEQ ID NO: 61 (3625 VH). In some embodiments, the antigen-binding domain that binds BCMA comprises (i) an amino acid sequence having at least 99% sequence identity with the amino acid sequence of SEQ ID NO: 56 (3625 VL); and (ii) an amino acid sequence having at least 99% sequence identity with the amino acid sequence of SEQ ID NO: 61 (3625 VH). In some embodiments, the antigen-binding domain that binds BCMA comprises (i) the amino acid sequence of SEQ ID NO: 56 (3625 VL); and (ii) the amino acid sequence of SEQ ID NO: 61 (3625 VH). In some embodiments, the antigen-binding domain that binds BCMA comprises an amino acid sequence having at least 80% sequence identity with the amino acid sequence of SEQ ID NO: 63 (3625 scFv VL-VH). In some embodiments, the antigen-binding domain that binds BCMA comprises an amino acid sequence having at least 85% sequence identity with the amino acid sequence of SEQ ID NO: 63 (3625 scFv VL-VH). In some embodiments, the antigen-binding domain that binds BCMA comprises an amino acid sequence having at least 90% sequence identity with the amino acid sequence of SEQ ID NO: 63 (3625 scFv VL-VH). In some embodiments, the antigen-binding domain that binds BCMA comprises an amino acid sequence having at least 95% sequence identity with the amino acid sequence of SEQ ID NO: 63 (3625 scFv VL-VH). In some embodiments, the antigen-binding domain that binds BCMA comprises an amino acid sequence having at least 96% sequence identity with the amino acid sequence of SEQ ID NO: 63 (3625 scFv VL-VH). In some embodiments, the antigen-binding domain that binds BCMA comprises an amino acid sequence having at least 97% sequence identity with the amino acid sequence of SEQ ID NO: 63 (3625 scFv VL-VH). In some embodiments, the antigen-binding domain that binds BCMA comprises an amino acid sequence having at least 98% sequence identity with the amino acid sequence of SEQ ID NO: 63 (3625 scFv VL-VH). In some embodiments, the antigen-binding domain that binds BCMA comprises an amino acid sequence having at least 99% sequence identity with the amino acid sequence of SEQ ID NO: 63 (3625 scFv VL-VH). In some embodiments, the antigen-binding domain that binds BCMA comprises the amino acid sequence of SEQ ID NO: 63 (3625 scFv VL-VH). In some embodiments, the CDR sequences of the antigen-binding domain that binds BCMA have 100% identity with the CDR sequences of the amino acid sequence of SEQ ID NO: 63 (3625 scFv VL-VH), and the non-CDR (e.g., framework) sequences of the antigen-binding domain that binds BCMA have at least 80% sequence identity with the non-CDR (e.g., framework) sequences of the amino acid sequence of SEQ ID NO: 63 (3625 scFv VL-VH). In some embodiments, the CDR sequences of the antigen-binding domain that binds BCMA have 100% identity with the CDR sequences of the amino acid sequence of SEQ ID NO: 63 (3625 scFv VL-VH), and the non-CDR (e.g., framework) sequences of the antigen-binding domain that binds BCMA have at least 85% sequence identity with the non-CDR (e.g., framework) sequences of the amino acid sequence of SEQ ID NO: 63 (3625 scFv VL-VH). In some embodiments, the CDR sequences of the antigen-binding domain that binds BCMA have 100% identity with the CDR sequences of the amino acid sequence of SEQ ID NO: 63 (3625 scFv VL-VH), and the non-CDR (e.g., framework) sequences of the antigen-binding domain that binds BCMA have at least 90% sequence identity with the non-CDR (e.g., framework) sequences of the amino acid sequence of SEQ ID NO: 63 (3625 scFv VL-VH). In some embodiments, the CDR sequences of the antigen-binding domain that binds BCMA have 100% identity with the CDR sequences of the amino acid sequence of SEQ ID NO: 63 (3625 scFv VL-VH), and the non-CDR (e.g., framework) sequences of the antigen-binding domain that binds BCMA have at least 95% sequence identity with the non-CDR (e.g., framework) sequences of the amino acid sequence of SEQ ID NO: 63 (3625 scFv VL-VH). In some embodiments, the CDR sequences of the antigen-binding domain that binds BCMA have 100% identity with the CDR sequences of the amino acid sequence of SEQ ID NO: 63 (3625 scFv VL-VH), and the non-CDR (e.g., framework) sequences of the antigen-binding domain that binds BCMA have at least 96% sequence identity with the non-CDR (e.g., framework) sequences of the amino acid sequence of SEQ ID NO: 63 (3625 scFv VL-VH). In some embodiments, the CDR sequences of the antigen-binding domain that binds BCMA have 100% identity with the CDR sequences of the amino acid sequence of SEQ ID NO: 63 (3625 scFv VL-VH), and the non-CDR (e.g., framework) sequences of the antigen-binding domain that binds BCMA have at least 97% sequence identity with the non-CDR (e.g., framework) sequences of the amino acid sequence of SEQ ID NO: 63 (3625 scFv VL-VH). In some embodiments, the CDR sequences of the antigen-binding domain that binds BCMA have 100% identity with the CDR sequences of the amino acid sequence of SEQ ID NO: 63 (3625 scFv VL-VH), and the non-CDR (e.g., framework) sequences of the antigen-binding domain that binds BCMA have at least 98% sequence identity with the non-CDR (e.g., framework) sequences of the amino acid sequence of SEQ ID NO: 63 (3625 scFv VL-VH). In some embodiments, the CDR sequences of the antigen-binding domain that binds BCMA have 100% identity with the CDR sequences of the amino acid sequence of SEQ ID NO: 63 (3625 scFv VL-VH), and the non-CDR (e.g., framework) sequences of the antigen-binding domain that binds BCMA have at least 99% sequence identity with the non-CDR (e.g., framework) sequences of the amino acid sequence of SEQ ID NO: 63 (3625 scFv VL-VH). In some embodiments, the antigen-binding domain that binds BCMA comprises an amino acid sequence having at least 80% sequence identity with the amino acid sequence of SEQ ID NO: 65 (3625 scFv VH-VL). In some embodiments, the antigen-binding domain that binds BCMA comprises an amino acid sequence having at least 85% sequence identity with the amino acid sequence of SEQ ID NO: 65 (3625 scFv VH-VL). In some embodiments, the antigen-binding domain that binds BCMA comprises an amino acid sequence having at least 90% sequence identity with the amino acid sequence of SEQ ID NO: 65 (3625 scFv VH-VL). In some embodiments, the antigen-binding domain that binds BCMA comprises an amino acid sequence having at least 95% sequence identity with the amino acid sequence of SEQ ID NO: 65 (3625 scFv VH-VL). In some embodiments, the antigen-binding domain that binds BCMA comprises an amino acid sequence having at least 96% sequence identity with the amino acid sequence of SEQ ID NO: 65 (3625 scFv VH-VL). In some embodiments, the antigen-binding domain that binds BCMA comprises an amino acid sequence having at least 97% sequence identity with the amino acid sequence of SEQ ID NO: 65 (3625 scFv VH-VL). In some embodiments, the antigen-binding domain that binds BCMA comprises an amino acid sequence having at least 98% sequence identity with the amino acid sequence of SEQ ID NO: 65 (3625 scFv VH-VL). In some embodiments, the antigen-binding domain that binds BCMA comprises an amino acid sequence having at least 99% sequence identity with the amino acid sequence of SEQ ID NO: 65 (3625 scFv VH-VL). In some embodiments, the antigen-binding domain that binds BCMA comprises the amino acid sequence of SEQ ID NO: 65 (3625 scFv VH-VL). In some embodiments, the CDR sequences of the antigen-binding domain that binds BCMA have 100% identity with the CDR sequences of the amino acid sequence of SEQ ID NO: 65 (3625 scFv VH-VL), and the non-CDR (e.g., framework) sequences of the antigen-binding domain that binds BCMA have at least 80% sequence identity with the non-CDR (e.g., framework) sequences of the amino acid sequence of SEQ ID NO: 65 (3625 scFv VH-VL). In some embodiments, the CDR sequences of the antigen-binding domain that binds BCMA have 100% identity with the CDR sequences of the amino acid sequence of SEQ ID NO: 65 (3625 scFv VH-VL), and the non-CDR (e.g., framework) sequences of the antigen-binding domain that binds BCMA have at least 85% sequence identity with the non-CDR (e.g., framework) sequences of the amino acid sequence of SEQ ID NO: 65 (3625 scFv VH-VL). In some embodiments, the CDR sequences of the antigen-binding domain that binds BCMA have 100% identity with the CDR sequences of the amino acid sequence of SEQ ID NO: 65 (3625 scFv VH-VL), and the non-CDR (e.g., framework) sequences of the antigen-binding domain that binds BCMA have at least 90% sequence identity with the non-CDR (e.g., framework) sequences of the amino acid sequence of SEQ ID NO: 65 (3625 scFv VH-VL). In some embodiments, the CDR sequences of the antigen-binding domain that binds BCMA have 100% identity with the CDR sequences of the amino acid sequence of SEQ ID NO: 65 (3625 scFv VH-VL), and the non-CDR (e.g., framework) sequences of the antigen-binding domain that binds BCMA have at least 95% sequence identity with the non-CDR (e.g., framework) sequences of the amino acid sequence of SEQ ID NO: 65 (3625 scFv VH-VL). In some embodiments, the CDR sequences of the antigen-binding domain that binds BCMA have 100% identity with the CDR sequences of the amino acid sequence of SEQ ID NO: 65 (3625 scFv VH-VL), and the non-CDR (e.g., framework) sequences of the antigen-binding domain that binds BCMA have at least 96% sequence identity with the non-CDR (e.g., framework) sequences of the amino acid sequence of SEQ ID NO: 65 (3625 scFv VH-VL). In some embodiments, the CDR sequences of the antigen-binding domain that binds BCMA have 100% identity with the CDR sequences of the amino acid sequence of SEQ ID NO: 65 (3625 scFv VH-VL), and the non-CDR (e.g., framework) sequences of the antigen-binding domain that binds BCMA have at least 97% sequence identity with the non-CDR (e.g., framework) sequences of the amino acid sequence of SEQ ID NO: 65 (3625 scFv VH-VL). In some embodiments, the CDR sequences of the antigen-binding domain that binds BCMA have 100% identity with the CDR sequences of the amino acid sequence of SEQ ID NO: 65 (3625 scFv VH-VL), and the non-CDR (e.g., framework) sequences of the antigen-binding domain that binds BCMA have at least 98% sequence identity with the non-CDR (e.g., framework) sequences of the amino acid sequence of SEQ ID NO: 65 (3625 scFv VH-VL). In some embodiments, the CDR sequences of the antigen-binding domain that binds BCMA have 100% identity with the CDR sequences of the amino acid sequence of SEQ ID NO: 65 (3625 scFv VH-VL), and the non-CDR (e.g., framework) sequences of the antigen-binding domain that binds BCMA have at least 99% sequence identity with the non-CDR (e.g., framework) sequences of the amino acid sequence of SEQ ID NO: 65 (3625 scFv VH-VL).

Amino acid and nucleotide sequences of exemplary antigen-binding domains that bind a protein associated with the TCR complex are provided in Table 1.

TABLE 1

Table of Sequences

| SEQ ID NO | Description | Nucleotide/Amino Acid |
|---|---|---|
| SEQ ID NO: 53 | 3625 VL - CDR1 | Amino Acid |
| SEQ ID NO: 54 | 3625 VL - CDR2 | Amino Acid |
| SEQ ID NO: 55 | 3625 VL - CDR3 | Amino Acid |
| SEQ ID NO: 56 | 3625 VL | Amino Acid |
| SEQ ID NO: 57 | 3625 VL | Nucleotide |
| SEQ ID NO: 58 | 3625 VH - CDR1 | Amino Acid |
| SEQ ID NO: 59 | 3625 VH - CDR2 | Amino Acid |

TABLE 1-continued

Table of Sequences

| SEQ ID NO | Description | Nucleotide/Amino Acid |
|---|---|---|
| SEQ ID NO: 60 | 3625 VH - CDR3 | Amino Acid |
| SEQ ID NO: 61 | 3625 VH | Amino Acid |
| SEQ ID NO: 62 | 3625 VH | Nucleotide |
| SEQ ID NO: 63 | 3625 scFv (VL-VH) | Amino Acid |
| SEQ ID NO: 64 | 3625 scFv (VL-VH) | Nucleotide |
| SEQ ID NO: 65 | 3625 scFv (VH-VL) | Amino Acid |
| SEQ ID NO: 66 | 3625 scFv (VH-VL) | Nucleotide |

TCR Complex Protein Antigen-Binding Domain

In certain embodiments, the BCMA TAC comprises an antigen-binding domain that binds a protein associated with the TCR complex. A "TCR complex protein antigen-binding domain," also referred to as a "TCR complex antigen-binding domain," "antigen-binding domain that binds the TCR complex," or "antigen-binding domain that binds a protein associated with the TCR complex," refers to any substance or molecule that binds, directly or indirectly, to a protein associated with a TCR complex. In some embodiments, the antigen-binding domain that binds a protein associated with a TCR complex selectively binds to a protein of the TCR. In some embodiments, the antigen-binding domain that binds a protein associated with a TCR complex comprises a substance that specifically binds to a protein of the TCR.

In some embodiments, the TCR complex protein antigen-binding domain is selected from antibodies or fragments thereof, for example, single chain antibodies (e.g., single-chain fragment variable antibodies (scFvs)), single domain antibodies (e.g., heavy-chain-only antibodies (VHH), shark heavy-chain-only antibodies (VNAR)), nanobodies, diabodies, minibodies, Fab fragments, Fab' fragments, F(ab')2 fragments, or Fv fragments that bind to a protein of the TCR. In some embodiments, the TCR complex protein antigen-binding domain is selected from ankyrin repeat proteins (DARPins), affibodies, adnectins, affilins, phylomers; fynomers, affimers, peptide aptamers, lectins, knottins, centyrins, anticalins, peptides, peptidomimetics, proteins, glycoproteins, or proteoglycans that bind to a protein of the TCR, or naturally occurring ligands for a protein of the TCR. In some embodiments, the TCR complex protein antigen-binding domain is a non-protein compound that binds to a protein of the TCR, including but not limited to carbohydrates, lipids, nucleic acids, or small molecules. In some embodiments, the TCR complex protein antigen-binding domain is a designed ankyrin repeat (DARPin) targeted to a protein of the TCR. In some embodiments, the TCR complex protein antigen-binding domain is a single-chain variable fragment (ScFv) targeted to a protein of the TCR. In some embodiments, the TCR complex protein antigen-binding domain is a nanobody targeted to a protein of the TCR.

Proteins associated with the TCR include, but are not limited, to the TCR alpha (α) chain, TCR beta (β) chain, TCR gamma (γ) chain, TCR delta (δ) chain, CD3γ chain, CD3δ chain and CD3ε chains. In some embodiments, an antigen-binding domain that binds a protein associated with the TCR complex is an antibody to the TCR alpha (α) chain, TCR beta (β) chain, TCR gamma (γ) chain, TCR delta (δ) chain, CD3γ chain, CD3δ chain and/or CD3ε chain. In some embodiments, the protein associated with a TCR complex is CD3. In some embodiments, the protein associated with a TCR complex is CD3ε. In some embodiments, the antigen-binding domain that binds CD3 is an antibody, for example, a single chain antibody, for example a single-chain variable fragment (scFv). Examples of CD3 antibodies, include, but are not limited to, UCHT1, OKT3, F6A, L2K, muromonab, otelixizumab, teplizumab, visilizumab, CD3-12, MEM-57, 4D10A6, CD3D, or TR66.

In some embodiments, the antigen-binding domain that binds the TCR complex is UCHT1, or a variant thereof. In some embodiments, the UCHT1 antigen-binding domain is encoded by SEQ ID NO: 31. In some embodiments, the UCHT1 antigen-binding domain comprises SEQ ID NO: 32. In some embodiments, the UCHT1 antigen-binding domain is mutated. In some embodiments, the UCHT1 antigen-binding domain comprises a Y to T mutation at a position corresponding to amino acid 182 of SEQ ID NO: 32 (Y182T). In some embodiments, the UCHT1 (Y182T) antigen-binding domain is encoded by SEQ ID NO: 43. In some embodiments, the UCHT1 (Y182T) antigen-binding domain comprises SEQ ID NO: 44. In some embodiments, the antigen-binding domain that binds the TCR complex is a humanized UCHT1 (huUCHT1). In some embodiments, the huUCHT1 antigen-binding domain is encoded by SEQ ID NO: 39. In some embodiments, the huUCHT1 antigen-binding domain comprises SEQ ID NO: 40. In some embodiments, the huUCHT1 has a Y to T mutation at a position corresponding to amino acid 177 of SEQ ID NO: 40 (Y177T). In some embodiments, the huUCHT1 (Y177T) antigen-binding domain is encoded by SEQ ID NO: 41. In some embodiments, the huUCHT1 antigen-binding domain comprises SEQ ID NO: 42.

In some embodiments, the polynucleotide encoding the antigen-binding domain that binds the protein associated with the TCR complex comprises a nucleotide sequence having at least 70% sequence identity with the nucleotide sequence of SEQ ID NO: 31 (UCHT1). In some embodiments, the polynucleotide encoding the antigen-binding domain that binds the protein associated with the TCR complex comprises a nucleotide sequence having at least 75% sequence identity with the nucleotide sequence of SEQ ID NO: 31 (UCHT1). In some embodiments, the polynucleotide encoding the antigen-binding domain that binds the protein associated with the TCR complex comprises a nucleotide sequence having at least 80% sequence identity with the nucleotide sequence of SEQ ID NO: 31 (UCHT1). In some embodiments, the polynucleotide encoding the antigen-binding domain that binds the protein associated with the TCR complex comprises a nucleotide sequence having at least 85% sequence identity with the nucleotide sequence of SEQ ID NO: 31 (UCHT1). In some embodiments, the polynucleotide encoding the antigen-binding domain that binds the protein associated with the TCR complex comprises a nucleotide sequence having at least 90% sequence identity with the nucleotide sequence of SEQ ID NO: 31 (UCHT1). In some embodiments, the polynucleotide encoding the antigen-binding domain that binds the protein associated with the TCR complex comprises a nucleotide sequence having at least 95% sequence identity with the nucleotide sequence of SEQ ID NO: 31 (UCHT1). In some embodiments, the polynucleotide encoding the antigen-binding domain that binds the protein associated with the TCR complex comprises a nucleotide sequence having at least 96% sequence identity with the nucleotide sequence of SEQ ID NO: 31 (UCHT1). In some embodiments, the polynucleotide encoding the antigen-binding domain that binds the protein associated with the TCR complex comprises a nucleotide sequence having at least 97% sequence identity with the nucleotide sequence of SEQ ID NO: 31 (UCHT1). In some embodiments, the polynucleotide encoding the antigen-binding domain that binds the protein associated with the TCR complex comprises a nucleotide sequence having at least 98% sequence identity with the nucleotide sequence of SEQ ID NO: 31 (UCHT1). In some embodiments, the polynucleotide encoding the antigen-binding domain that binds the protein associated with the TCR complex comprises a nucleotide sequence having at least 99% sequence identity with the nucleotide sequence of SEQ ID NO: 31 (UCHT1). In some embodiments, the polynucleotide encoding the antigen-binding domain that binds the protein associated with the TCR complex comprises the nucleotide sequence of SEQ ID NO: 31 (UCHT1).

In some embodiments, the antigen-binding domain that binds the protein associated with the TCR complex comprises an amino acid sequence having at least 70% sequence identity with the amino acid sequence of SEQ ID NO: 32 (UCHT1). In some embodiments, the antigen-binding domain that binds the protein associated with the TCR complex comprises an amino acid sequence having at least 75% sequence identity with the amino acid sequence of SEQ ID NO: 32 (UCHT1). In some embodiments, the antigen-binding domain that binds the protein associated with the TCR complex comprises an amino acid sequence having at least 80% sequence identity with the amino acid sequence of SEQ ID NO: 32 (UCHT1). In some embodiments, the antigen-binding domain that binds the protein associated with the TCR complex comprises an amino acid sequence having at least 85% sequence identity with the amino acid sequence of SEQ ID NO: 32 (UCHT1). In some embodiments, the antigen-binding domain that binds the protein associated with the TCR complex comprises an amino acid sequence having at least 90% sequence identity with the amino acid sequence of SEQ ID NO: 32 (UCHT1). In some embodiments, the antigen-binding domain that binds the protein associated with the TCR complex comprises an amino acid sequence having at least 95% sequence identity with the amino acid sequence of SEQ ID NO: 32 (UCHT1). In some embodiments, the antigen-binding domain that binds the protein associated with the TCR complex comprises an amino acid sequence having at least 96% sequence identity with the amino acid sequence of SEQ ID NO: 32 (UCHT1). In some embodiments, the antigen-binding domain that binds the protein associated with the TCR complex comprises an amino acid sequence having at least 97% sequence identity with the amino acid sequence of SEQ ID NO: 32 (UCHT1). In some embodiments, the antigen-binding domain that binds the protein associated with the TCR complex comprises an amino acid sequence having at least 98% sequence identity with the amino acid sequence of SEQ ID NO: 32 (UCHT1). In some embodiments, the antigen-binding domain that binds the protein associated with the TCR complex comprises an amino acid sequence having at least 99% sequence identity with the amino acid sequence of SEQ ID NO: 32 (UCHT1). In some embodiments, the antigen-binding domain that binds the protein associated with the TCR complex comprises the amino acid sequence of SEQ ID NO: 32 (UCHT1). In some embodiments, the CDR sequences of the antigen-binding domain that binds the protein associated with the TCR complex have 100% identity with the CDR sequences of the amino acid sequence of SEQ ID NO: 32 (UCHT1) (i.e., the antigen-binding domain that binds the protein associated with the TCR complex comprises an amino acid sequence comprising a CDRH1, CDRH2, CDRH3, CDRL1, CDRL2, and CDRL3, each having 100% identity to the corresponding CDR in the amino acid sequence of SEQ ID NO: 32 (UCHT1). In some embodiments, the CDR sequences of the antigen-binding domain that binds the protein associated with the TCR complex have 100% identity with the CDR sequences of the amino acid sequence of SEQ ID NO: 32 (UCHT1), and the non-CDR (e.g., framework) sequences of the antigen-binding domain that binds the protein associated with the TCR complex have at least 80% sequence identity with the non-CDR (e.g., framework) sequences of the amino acid sequence of SEQ ID NO: 32 (UCHT1). In some embodiments, the CDR sequences of the antigen-binding domain that binds the protein associated with the TCR complex have 100% identity with the CDR sequences of the amino acid sequence of SEQ ID NO: 32 (UCHT1), and the non-CDR (e.g., framework) sequences of the antigen-binding domain that binds the protein associated with the TCR complex have at least 85% sequence identity with the non-CDR (e.g., framework) sequences of the amino acid sequence of SEQ ID NO: 32 (UCHT1). In some embodiments, the CDR sequences of the antigen-binding domain that binds the protein associated with the TCR complex have 100% identity with the CDR sequences of the amino acid sequence of SEQ ID NO: 32 (UCHT1), and the non-CDR (e.g., framework) sequences of the antigen-binding domain that binds the protein associated with the TCR complex have at least 90% sequence identity with the non-CDR (e.g., framework) sequences of the amino acid sequence of SEQ ID NO: 32 (UCHT1). In some embodiments, the CDR sequences of the antigen-binding domain that binds the protein associated with the TCR complex have 100% identity with the CDR sequences of the amino acid sequence of SEQ ID NO: 32 (UCHT1), and the non-CDR (e.g., framework) sequences of the antigen-binding domain that binds the protein associated with the TCR complex have at least 95% sequence identity with the non-CDR (e.g., framework) sequences of the amino acid sequence of SEQ ID NO: 32 (UCHT1). In some embodiments, the CDR sequences of the antigen-binding domain that binds the protein associated with the TCR complex have 100% identity with the CDR sequences of the amino acid sequence of SEQ ID NO: 32 (UCHT1), and the non-CDR (e.g., framework) sequences of the antigen-binding domain that binds the protein associated with the TCR complex have at least 96% sequence identity with the non-CDR (e.g., framework) sequences of the amino acid sequence of SEQ ID NO: 32 (UCHT1). In some embodiments, the CDR sequences of the antigen-binding domain that binds the protein associated with the TCR complex have 100% identity with the CDR sequences of the amino acid sequence of SEQ ID NO: 32 (UCHT1), and the non-CDR (e.g., framework) sequences of the antigen-binding domain that binds the protein associated with the TCR complex have at least 97% sequence identity with the non-CDR (e.g., framework) sequences of the amino acid sequence of SEQ ID NO: 32 (UCHT1). In some embodiments, the CDR sequences of the antigen-binding domain that binds the protein associated with the TCR complex have 100% identity with the CDR sequences of the amino acid sequence of SEQ ID NO: 32 (UCHT1), and the non-CDR (e.g., framework) sequences of the antigen-binding domain that binds the protein associated with the TCR complex have at least 98% sequence identity with the non-CDR (e.g., framework) sequences of the amino acid sequence of SEQ ID NO: 32 (UCHT1). In some embodiments, the CDR sequences of the antigen-binding domain that binds the protein associated with the TCR complex have 100% identity with the CDR sequences of the amino acid sequence of SEQ ID NO: 32 (UCHT1), and the non-CDR (e.g., framework) sequences of the antigen-binding domain that binds the protein associated with the TCR complex have at least 99% sequence identity with the non-CDR (e.g., framework) sequences of the amino acid sequence of SEQ ID NO: 32 (UCHT1).

In some embodiments, the polynucleotide encoding the antigen-binding domain that binds the protein associated with the TCR complex comprises a nucleotide sequence having at least 70% sequence identity with the nucleotide sequence of SEQ ID NO: 43 (UCHT1 (Y182T)). In some embodiments, the polynucleotide encoding the antigen-binding domain that binds the protein associated with the TCR complex comprises a nucleotide sequence having at least 75% sequence identity with the nucleotide sequence of SEQ ID NO: 43 (UCHT1 (Y182T)). In some embodiments, the polynucleotide encoding the antigen-binding domain that binds the protein associated with the TCR complex comprises a nucleotide sequence having at least 80% sequence identity with the nucleotide sequence of SEQ ID NO: 43 (UCHT1 (Y182T)). In some embodiments, the polynucleotide encoding the antigen-binding domain that binds the protein associated with the TCR complex comprises a nucleotide sequence having at least 85% sequence identity with the nucleotide sequence of SEQ ID NO: 43 (UCHT1 (Y182T)). In some embodiments, the polynucleotide encoding the antigen-binding domain that binds the protein associated with the TCR complex comprises a nucleotide sequence having at least 90% sequence identity with the nucleotide sequence of SEQ ID NO: 43 (UCHT1 (Y182T)). In some embodiments, the polynucleotide encoding the antigen-binding domain that binds the protein associated with the TCR complex comprises a nucleotide sequence having at least 95% sequence identity with the nucleotide sequence of SEQ ID NO: 43 (UCHT1 (Y182T)). In some embodiments, the polynucleotide encoding the antigen-binding domain that binds the protein associated with the TCR complex comprises a nucleotide sequence having at least 96% sequence identity with the nucleotide sequence of SEQ ID NO: 43 (UCHT1 (Y182T)). In some embodiments, the polynucleotide encoding the antigen-binding domain that binds the protein associated with the TCR complex comprises a nucleotide sequence having at least 97% sequence identity with the nucleotide sequence of SEQ ID NO: 43 (UCHT1 (Y182T)). In some embodiments, the polynucleotide encoding the antigen-binding domain that binds the protein associated with the TCR complex comprises a nucleotide sequence having at least 98% sequence identity with the nucleotide sequence of SEQ ID NO: 43 (UCHT1 (Y182T)). In some embodiments, the polynucleotide encoding the antigen-binding domain that binds the protein associated with the TCR complex comprises a nucleotide sequence having at least 99% sequence identity with the nucleotide sequence of SEQ ID NO: 43 (UCHT1 (Y182T)). In some embodiments, the polynucleotide encoding the antigen-binding domain that binds the protein associated with the TCR complex comprises the nucleotide sequence of SEQ ID NO: 43 (UCHT1 (Y182T)).

In some embodiments, the antigen-binding domain that binds the protein associated with the TCR complex comprises an amino acid sequence having at least 70% sequence identity with the amino acid sequence of SEQ ID NO: 44 (UCHT1 (Y182T)). In some embodiments, the antigen-binding domain that binds the protein associated with the TCR complex comprises an amino acid sequence having at least 75% sequence identity with the amino acid sequence of SEQ ID NO: 44 (UCHT1 (Y182T)). In some embodiments, the antigen-binding domain that binds the protein associated with the TCR complex comprises an amino acid sequence having at least 80% sequence identity with the amino acid sequence of SEQ ID NO: 44 (UCHT1 (Y182T)). In some embodiments, the antigen-binding domain that binds the protein associated with the TCR complex comprises an amino acid sequence having at least 85% sequence identity with the amino acid sequence of SEQ ID NO: 44 (UCHT1 (Y182T)). In some embodiments, the antigen-binding domain that binds the protein associated with the TCR complex comprises an amino acid sequence having at least 90% sequence identity with the amino acid sequence of SEQ ID NO: 44 (UCHT1 (Y182T)). In some embodiments, the antigen-binding domain that binds the protein associated with the TCR complex comprises an amino acid sequence having at least 95% sequence identity with the amino acid sequence of SEQ ID NO: 44 (UCHT1 (Y182T)). In some embodiments, the antigen-binding domain that binds the protein associated with the TCR complex comprises an amino acid sequence having at least 96% sequence identity with the amino acid sequence of SEQ ID NO: 44 (UCHT1 (Y182T)). In some embodiments, the antigen-binding domain that binds the protein associated with the TCR complex comprises an amino acid sequence having at least 97% sequence identity with the amino acid sequence of SEQ ID NO: 44 (UCHT1 (Y182T)). In some embodiments, the antigen-binding domain that binds the protein associated with the TCR complex comprises an amino acid sequence having at least 98% sequence identity with the amino acid sequence of SEQ ID NO: 44 (UCHT1 (Y182T)). In some embodiments, the antigen-binding domain that binds the protein associated with the TCR complex comprises an amino acid sequence having at least 99% sequence identity with the amino acid sequence of SEQ ID NO: 44 (UCHT1 (Y182T)). In some embodiments, the antigen-binding domain that binds the protein associated with the TCR complex comprises the amino acid sequence of SEQ ID NO: 44 (UCHT1 (Y182T)). In some embodiments, the CDR sequences of the antigen-binding domain that binds the protein associated with the TCR complex have 100% identity with the CDR sequences of the amino acid sequence of SEQ ID NO: 44 (UCHT1 (Y182T)) (i.e., the antigen-binding domain that binds the protein associated with the TCR complex comprises an amino acid sequence comprising a CDRH1, CDRH2, CDRH3, CDRL1, CDRL2, and CDRL3, each having 100% identity to the corresponding CDR in the amino acid sequence of SEQ ID NO: 44 (UCHT1 (Y182T)). In some embodiments, the CDR sequences of the antigen-binding domain that binds the protein associated with the TCR complex have 100% identity with the CDR sequences of the amino acid sequence of SEQ ID NO: 44 (UCHT1 (Y182T)), and the non-CDR (e.g., framework) sequences of the antigen-binding domain that binds the protein associated with the TCR complex have at least 80% sequence identity with the non-CDR (e.g., framework) sequences of the amino acid sequence of SEQ ID NO: 44 (UCHT1 (Y182T)). In some embodiments, the CDR sequences of the antigen-binding domain that binds the protein associated with the TCR complex have 100% identity with the CDR sequences of the amino acid sequence of SEQ ID NO: 44 (UCHT1 (Y182T)), and the non-CDR (e.g., framework) sequences of the antigen-binding domain that binds the protein associated with the TCR complex have at least 85% sequence identity with the non-CDR (e.g., framework) sequences of the amino acid sequence of SEQ ID NO: 44 (UCHT1 (Y182T)). In some embodiments, the CDR sequences of the antigen-binding domain that binds the protein associated with the TCR complex have 100% identity with the CDR sequences of the amino acid sequence of SEQ ID NO: 44 (UCHT1 (Y182T)), and the non-CDR (e.g., framework) sequences of the antigen-binding domain that binds the protein associated with the TCR complex have at least 90% sequence identity with the non-CDR (e.g., framework) sequences of the amino acid sequence of SEQ ID NO: 44 (UCHT1 (Y182T)). In some embodiments, the CDR sequences of the antigen-binding domain that binds the protein associated with the TCR complex have 100% identity with the CDR sequences of the amino acid sequence of SEQ ID NO: 44 (UCHT1 (Y182T)), and the non-CDR (e.g., framework) sequences of the antigen-binding domain that binds the protein associated with the TCR complex have at least 95% sequence identity with the non-CDR (e.g., framework) sequences of the amino acid sequence of SEQ ID NO: 44 (UCHT1 (Y182T)). In some embodiments, the CDR sequences of the antigen-binding domain that binds the protein associated with the TCR complex have 100% identity with the CDR sequences of the amino acid sequence of SEQ ID NO: 44 (UCHT1 (Y182T)), and the non-CDR (e.g., framework) sequences of the antigen-binding domain that binds the protein associated with the TCR complex have at least 96% sequence identity with the non-CDR (e.g., framework) sequences of the amino acid sequence of SEQ ID NO: 44 (UCHT1 (Y182T)). In some embodiments, the CDR sequences of the antigen-binding domain that binds the protein associated with the TCR complex have 100% identity with the CDR sequences of the amino acid sequence of SEQ ID NO: 44 (UCHT1 (Y182T)), and the non-CDR (e.g., framework) sequences of the antigen-binding domain that binds the protein associated with the TCR complex have at least 97% sequence identity with the non-CDR (e.g., framework) sequences of the amino acid sequence of SEQ ID NO: 44 (UCHT1 (Y182T)). In some embodiments, the CDR sequences of the antigen-binding domain that binds the protein associated with the TCR complex have 100% identity with the CDR sequences of the amino acid sequence of SEQ ID NO: 44 (UCHT1 (Y182T)), and the non-CDR (e.g., framework) sequences of the antigen-binding domain that binds the protein associated with the TCR complex have at least 98% sequence identity with the non-CDR (e.g., framework) sequences of the amino acid sequence of SEQ ID NO: 44 (UCHT1 (Y182T)). In some embodiments, the CDR sequences of the antigen-binding domain that binds the protein associated with the TCR complex have 100% identity with the CDR sequences of the amino acid sequence of SEQ ID NO: 44 (UCHT1 (Y182T)), and the non-CDR (e.g., framework) sequences of the antigen-binding domain that binds the protein associated with the TCR complex have at least 99% sequence identity with the non-CDR (e.g., framework) sequences of the amino acid sequence of SEQ ID NO: 44 (UCHT1 (Y182T)).

In some embodiments, the polynucleotide encoding the antigen-binding domain that binds the protein associated with the TCR complex comprises a nucleotide sequence having at least 70% sequence identity with the nucleotide sequence of SEQ ID NO: 39 (huUCHT1). In some embodiments, the polynucleotide encoding the antigen-binding domain that binds the protein associated with the TCR complex comprises a nucleotide sequence having at least 75% sequence identity with the nucleotide sequence of SEQ ID NO: 39 (huUCHT1). In some embodiments, the polynucleotide encoding the antigen-binding domain that binds the protein associated with the TCR complex comprises a nucleotide sequence having at least 80% sequence identity with the nucleotide sequence of SEQ ID NO: 39 (huUCHT1). In some embodiments, the polynucleotide encoding the antigen-binding domain that binds the protein associated with the TCR complex comprises a nucleotide sequence having at least 85% sequence identity with the nucleotide sequence of SEQ ID NO: 39 (huUCHT1). In some embodiments, the polynucleotide encoding the antigen-binding domain that binds the protein associated with the TCR complex comprises a nucleotide sequence having at least 90% sequence identity with the nucleotide sequence of SEQ ID NO: 39 (huUCHT1). In some embodiments, the polynucleotide encoding the antigen-binding domain that binds the protein associated with the TCR complex comprises a nucleotide sequence having at least 95% sequence identity with the nucleotide sequence of SEQ ID NO: 39 (huUCHT1). In some embodiments, the polynucleotide encoding the antigen-binding domain that binds the protein associated with the TCR complex comprises a nucleotide sequence having at least 96% sequence identity with the nucleotide sequence of SEQ ID NO: 39 (huUCHT1). In some embodiments, the polynucleotide encoding the antigen-binding domain that binds the protein associated with the TCR complex comprises a nucleotide sequence having at least 97% sequence identity with the nucleotide sequence of SEQ ID NO: 39 (huUCHT1). In some embodiments, the polynucleotide encoding the antigen-binding domain that binds the protein associated with the TCR complex comprises a nucleotide sequence having at least 98% sequence identity with the nucleotide sequence of SEQ ID NO: 39 (huUCHT1). In some embodiments, the polynucleotide encoding the antigen-binding domain that binds the protein associated with the TCR complex comprises a nucleotide sequence having at least 99% sequence identity with the nucleotide sequence of SEQ ID NO: 39 (huUCHT1). In some embodiments, the polynucleotide encoding the antigen-binding domain that binds the protein associated with the TCR complex comprises the nucleotide sequence of SEQ ID NO: 39 (huUCHT1).

In some embodiments, the antigen-binding domain that binds the protein associated with the TCR complex comprises an amino acid sequence having at least 70% sequence identity with the amino acid sequence of SEQ ID NO: 40 (huUCHT1). In some embodiments, the antigen-binding domain that binds the protein associated with the TCR complex comprises an amino acid sequence having at least 75% sequence identity with the amino acid sequence of SEQ ID NO: 40 (huUCHT1). In some embodiments, the antigen-binding domain that binds the protein associated with the TCR complex comprises an amino acid sequence having at least 80% sequence identity with the amino acid sequence of SEQ ID NO: 40 (huUCHT1). In some embodiments, the antigen-binding domain that binds the protein associated with the TCR complex comprises an amino acid sequence having at least 85% sequence identity with the amino acid sequence of SEQ ID NO: 40 (huUCHT1). In some embodiments, the antigen-binding domain that binds the protein associated with the TCR complex comprises an amino acid sequence having at least 90% sequence identity with the amino acid sequence of SEQ ID NO: 40 (huUCHT1). In some embodiments, the antigen-binding domain that binds the protein associated with the TCR complex comprises an amino acid sequence having at least 95% sequence identity with the amino acid sequence of SEQ ID NO: 40 (huUCHT1). In some embodiments, the antigen-binding domain that binds the protein associated with the TCR complex comprises an amino acid sequence having at least 96% sequence identity with the amino acid sequence of SEQ ID NO: 40 (huUCHT1). In some embodiments, the antigen-binding domain that binds the protein associated with the TCR complex comprises an amino acid sequence having at least 97% sequence identity with the amino acid sequence of SEQ ID NO: 40 (huUCHT1). In some embodiments, the antigen-binding domain that binds the protein associated with the TCR complex comprises an amino acid sequence having at least 98% sequence identity with the amino acid sequence of SEQ ID NO: 40 (huUCHT1). In some embodiments, the antigen-binding domain that binds the protein associated with the TCR complex comprises an amino acid sequence having at least 99% sequence identity with the amino acid sequence of SEQ ID NO: 40 (huUCHT1). In some embodiments, the antigen-binding domain that binds the protein associated with the TCR complex comprises the amino acid sequence of SEQ ID NO: 40 (huUCHT1). In some embodiments, the CDR sequences of the antigen-binding domain that binds the protein associated with the TCR complex have 100% identity with the CDR sequences of the amino acid sequence of SEQ ID NO: 40 (huUCHT1) (i.e., the antigen-binding domain that binds the protein associated with the TCR complex comprises an amino acid sequence comprising a CDRH1, CDRH2, CDRH3, CDRL1, CDRL2, and CDRL3, each having 100% identity to the corresponding CDR in the amino acid sequence of SEQ ID NO: 40 (huUCHT1). In some embodiments, the CDR sequences of the antigen-binding domain that binds the protein associated with the TCR complex have 100% identity with the CDR sequences of the amino acid sequence of SEQ ID NO: 40 (huUCHT1), and the non-CDR (e.g., framework) sequences of the antigen-binding domain that binds the protein associated with the TCR complex have at least 80% sequence identity with the non-CDR (e.g., framework) sequences of the amino acid sequence of SEQ ID NO: 40 (huUCHT1). In some embodiments, the CDR sequences of the antigen-binding domain that binds the protein associated with the TCR complex have 100% identity with the CDR sequences of the amino acid sequence of SEQ ID NO: 40 (huUCHT1), and the non-CDR (e.g., framework) sequences of the antigen-binding domain that binds the protein associated with the TCR complex have at least 85% sequence identity with the non-CDR (e.g., framework) sequences of the amino acid sequence of SEQ ID NO: 40 (huUCHT1). In some embodiments, the CDR sequences of the antigen-binding domain that binds the protein associated with the TCR complex have 100% identity with the CDR sequences of the amino acid sequence of SEQ ID NO: 40 (huUCHT1), and the non-CDR (e.g., framework) sequences of the antigen-binding domain that binds the protein associated with the TCR complex have at least 90% sequence identity with the non-CDR (e.g., framework) sequences of the amino acid sequence of SEQ ID NO: 40 (huUCHT1). In some embodiments, the CDR sequences of the antigen-binding domain that binds the protein associated with the TCR complex have 100% identity with the CDR sequences of the amino acid sequence of SEQ ID NO: 40 (huUCHT1), and the non-CDR (e.g., framework) sequences of the antigen-binding domain that binds the protein associated with the TCR complex have at least 95% sequence identity with the non-CDR (e.g., framework) sequences of the amino acid sequence of SEQ ID NO: 40 (huUCHT1). In some embodiments, the CDR sequences of the antigen-binding domain that binds the protein associated with the TCR complex have 100% identity with the CDR sequences of the amino acid sequence of SEQ ID NO: 40 (huUCHT1), and the non-CDR (e.g., framework) sequences of the antigen-binding domain that binds the protein associated with the TCR complex have at least 96% sequence identity with the non-CDR (e.g., framework) sequences of the amino acid sequence of SEQ ID NO: 40 (huUCHT1). In some embodiments, the CDR sequences of the antigen-binding domain that binds the protein associated with the TCR complex have 100% identity with the CDR sequences of the amino acid sequence of SEQ ID NO: 40 (huUCHT1), and the non-CDR (e.g., framework) sequences of the antigen-binding domain that binds the protein associated with the TCR complex have at least 97% sequence identity with the non-CDR (e.g., framework) sequences of the amino acid sequence of SEQ ID NO: 40 (huUCHT1). In some embodiments, the CDR sequences of the antigen-binding domain that binds the protein associated with the TCR complex have 100% identity with the CDR sequences of the amino acid sequence of SEQ ID NO: 40 (huUCHT1), and the non-CDR (e.g., framework) sequences of the antigen-binding domain that binds the protein associated with the TCR complex have at least 98% sequence identity with the non-CDR (e.g., framework) sequences of the amino acid sequence of SEQ ID NO: 40 (huUCHT1). In some embodiments, the CDR sequences of the antigen-binding domain that binds the protein associated with the TCR complex have 100% identity with the CDR sequences of the amino acid sequence of SEQ ID NO: 40 (huUCHT1), and the non-CDR (e.g., framework) sequences of the antigen-binding domain that binds the protein associated with the TCR complex have at least 99% sequence identity with the non-CDR (e.g., framework) sequences of the amino acid sequence of SEQ ID NO: 40 (huUCHT1).

In some embodiments, the polynucleotide encoding the antigen-binding domain that binds the protein associated with the TCR complex comprises a nucleotide sequence having at least 70% sequence identity with the nucleotide sequence of SEQ ID NO: 41 (huUCHT1 (Y177T)). In some embodiments, the polynucleotide encoding the antigen-binding domain that binds the protein associated with the TCR complex comprises a nucleotide sequence having at least 75% sequence identity with the nucleotide sequence of SEQ ID NO: 41 (huUCHT1 (Y177T)). In some embodiments, the polynucleotide encoding the antigen-binding domain that binds the protein associated with the TCR complex comprises a nucleotide sequence having at least 80% sequence identity with the nucleotide sequence of SEQ ID NO: 41 (huUCHT1 (Y177T)). In some embodiments, the polynucleotide encoding the antigen-binding domain that binds the protein associated with the TCR complex comprises a nucleotide sequence having at least 85% sequence identity with the nucleotide sequence of SEQ ID NO: 41 (huUCHT1 (Y177T)). In some embodiments, the polynucleotide encoding the antigen-binding domain that binds the protein associated with the TCR complex comprises a nucleotide sequence having at least 90% sequence identity with the nucleotide sequence of SEQ ID NO: 41 (huUCHT1 (Y177T)). In some embodiments, the polynucleotide encoding the antigen-binding domain that binds the protein associated with the TCR complex comprises a nucleotide sequence having at least 95% sequence identity with the nucleotide sequence of SEQ ID NO: 41 (huUCHT1 (Y177T)). In some embodiments, the polynucleotide encoding the antigen-binding domain that binds the protein associated with the TCR complex comprises a nucleotide sequence having at least 96% sequence identity with the nucleotide sequence of SEQ ID NO: 41 (huUCHT1 (Y177T)). In some embodiments, the polynucleotide encoding the antigen-binding domain that binds the protein associated with the TCR complex comprises a nucleotide sequence having at least 97% sequence identity with the nucleotide sequence of SEQ ID NO: 41 (huUCHT1 (Y177T)). In some embodiments, the polynucleotide encoding the antigen-binding domain that binds the protein associated with the TCR complex comprises a nucleotide sequence having at least 98% sequence identity with the nucleotide sequence of SEQ ID NO: 41 (huUCHT1 (Y177T)). In some embodiments, the polynucleotide encoding the antigen-binding domain that binds the protein associated with the TCR complex comprises a nucleotide sequence having at least 99% sequence identity with the nucleotide sequence of SEQ ID NO: 41 (huUCHT1 (Y177T)). In some embodiments, the polynucleotide encoding the antigen-binding domain that binds the protein associated with the TCR complex comprises the nucleotide sequence of SEQ ID NO: 41 (huUCHT1 (Y177T)).

In some embodiments, the antigen-binding domain that binds the protein associated with the TCR complex comprises an amino acid sequence having at least 70% sequence identity with the amino acid sequence of SEQ ID NO: 42 (huUCHT1 (Y177T)). In some embodiments, the antigen-binding domain that binds the protein associated with the TCR complex comprises an amino acid sequence having at least 75% sequence identity with the amino acid sequence of SEQ ID NO: 42 (huUCHT1 (Y177T)). In some embodiments, the antigen-binding domain that binds the protein associated with the TCR complex comprises an amino acid sequence having at least 80% sequence identity with the amino acid sequence of SEQ ID NO: 42 (huUCHT1 (Y177T)). In some embodiments, the antigen-binding domain that binds the protein associated with the TCR complex comprises an amino acid sequence having at least 85% sequence identity with the amino acid sequence of SEQ ID NO: 42 (huUCHT1 (Y177T)). In some embodiments, the antigen-binding domain that binds the protein associated with the TCR complex comprises an amino acid sequence having at least 90% sequence identity with the amino acid sequence of SEQ ID NO: 42 (huUCHT1 (Y177T)). In some embodiments, the antigen-binding domain that binds the protein associated with the TCR complex comprises an amino acid sequence having at least 95% sequence identity with the amino acid sequence of SEQ ID NO: 42 (huUCHT1 (Y177T)). In some embodiments, the antigen-binding domain that binds the protein associated with the TCR complex comprises an amino acid sequence having at least 96% sequence identity with the amino acid sequence of SEQ ID NO: 42 (huUCHT1 (Y177T)). In some embodiments, the antigen-binding domain that binds the protein associated with the TCR complex comprises an amino acid sequence having at least 97% sequence identity with the amino acid sequence of SEQ ID NO: 42 (huUCHT1 (Y177T)). In some embodiments, the antigen-binding domain that binds the protein associated with the TCR complex comprises an amino acid sequence having at least 98% sequence identity with the amino acid sequence of SEQ ID NO: 42 (huUCHT1 (Y177T)). In some embodiments, the antigen-binding domain that binds the protein associated with the TCR complex comprises an amino acid sequence having at least 99% sequence identity with the amino acid sequence of SEQ ID NO: 42 (huUCHT1 (Y177T)). In some embodiments, the antigen-binding domain that binds the protein associated with the TCR complex comprises the amino acid sequence of SEQ ID NO: 42 (huUCHT1 (Y177T)). In some embodiments, the CDR sequences of the antigen-binding domain that binds the protein associated with the TCR complex have 100% identity with the CDR sequences of the amino acid sequence of SEQ ID NO: 42 (huUCHT1 (Y177T)) (i.e., the antigen-binding domain that binds the protein associated with the TCR complex comprises an amino acid sequence comprising a CDRH1, CDRH2, CDRH3, CDRL1, CDRL2, and CDRL3, each having 100% identity to the corresponding CDR in the amino acid sequence of SEQ ID NO: 42 (huUCHT1 (Y177T)). In some embodiments, the CDR sequences of the antigen-binding domain that binds the protein associated with the TCR complex have 100% identity with the CDR sequences of the amino acid sequence of SEQ ID NO: 42 (huUCHT1 (Y177T)), and the non-CDR (e.g., framework) sequences of the antigen-binding domain that binds the protein associated with the TCR complex have at least 80% sequence identity with the non-CDR (e.g., framework) sequences of the amino acid sequence of SEQ ID NO: 42 (huUCHT1 (Y177T)). In some embodiments, the CDR sequences of the antigen-binding domain that binds the protein associated with the TCR complex have 100% identity with the CDR sequences of the amino acid sequence of SEQ ID NO: 42 (huUCHT1 (Y177T)), and the non-CDR (e.g., framework) sequences of the antigen-binding domain that binds the protein associated with the TCR complex have at least 85% sequence identity with the non-CDR (e.g., framework) sequences of the amino acid sequence of SEQ ID NO: 42 (huUCHT1 (Y177T)). In some embodiments, the CDR sequences of the antigen-binding domain that binds the protein associated with the TCR complex have 100% identity with the CDR sequences of the amino acid sequence of SEQ ID NO: 42 (huUCHT1 (Y177T)), and the non-CDR (e.g., framework) sequences of the antigen-binding domain that binds the protein associated with the TCR complex have at least 90% sequence identity with the non-CDR (e.g., framework) sequences of the amino acid sequence of SEQ ID NO: 42 (huUCHT1 (Y177T)). In some embodiments, the CDR sequences of the antigen-binding domain that binds the protein associated with the TCR complex have 100% identity with the CDR sequences of the amino acid sequence of SEQ ID NO: 42 (huUCHT1 (Y177T)), and the non-CDR (e.g., framework) sequences of the antigen-binding domain that binds the protein associated with the TCR complex have at least 95% sequence identity with the non-CDR (e.g., framework) sequences of the amino acid sequence of SEQ ID NO: 42 (huUCHT1 (Y177T)). In some embodiments, the CDR sequences of the antigen-binding domain that binds the protein associated with the TCR complex have 100% identity with the CDR sequences of the amino acid sequence of SEQ ID NO: 42 (huUCHT1 (Y177T)), and the non-CDR (e.g., framework) sequences of the antigen-binding domain that binds the protein associated with the TCR complex have at least 96% sequence identity with the non-CDR (e.g., framework) sequences of the amino acid sequence of SEQ ID NO: 42 (huUCHT1 (Y177T)). In some embodiments, the CDR sequences of the antigen-binding domain that binds the protein associated with the TCR complex have 100% identity with the CDR sequences of the amino acid sequence of SEQ ID NO: 42 (huUCHT1 (Y177T)), and the non-CDR (e.g., framework) sequences of the antigen-binding domain that binds the protein associated with the TCR complex have at least 97% sequence identity with the non-CDR (e.g., framework) sequences of the amino acid sequence of SEQ ID NO: 42 (huUCHT1 (Y177T)). In some embodiments, the CDR sequences of the antigen-binding domain that binds the protein associated with the TCR complex have 100% identity with the CDR sequences of the amino acid sequence of SEQ ID NO: 42 (huUCHT1 (Y177T)), and the non-CDR (e.g., framework) sequences of the antigen-binding domain that binds the protein associated with the TCR complex have at least 98% sequence identity with the non-CDR (e.g., framework) sequences of the amino acid sequence of SEQ ID NO: 42 (huUCHT1 (Y177T)). In some embodiments, the CDR sequences of the antigen-binding domain that binds the protein associated with the TCR complex have 100% identity with the CDR sequences of the amino acid sequence of SEQ ID NO: 42 (huUCHT1 (Y177T)), and the non-CDR (e.g., framework) sequences of the antigen-binding domain that binds the protein associated with the TCR complex have at least 99% sequence identity with the non-CDR (e.g., framework) sequences of the amino acid sequence of SEQ ID NO: 42 (huUCHT1 (Y177T)).

In some embodiments, the antigen-binding domain that binds to the protein associated with the TCR complex is OKT3. In some embodiments, the murine OKT3 antigen-binding domain is encoded by SEQ ID NO: 33. In some embodiments, the OKT3 antigen-binding domain comprises SEQ ID NO: 34.

In some embodiments, the polynucleotide encoding the antigen-binding domain that binds the protein associated with the TCR complex comprises a nucleotide sequence having at least 70% sequence identity with the nucleotide sequence of SEQ ID NO: 33(OKT3). In some embodiments, the polynucleotide encoding the antigen-binding domain that binds the protein associated with the TCR complex comprises a nucleotide sequence having at least 75% sequence identity with the nucleotide sequence of SEQ ID NO: 33(OKT3). In some embodiments, the polynucleotide encoding the antigen-binding domain that binds the protein associated with the TCR complex comprises a nucleotide sequence having at least 80% sequence identity with the nucleotide sequence of SEQ ID NO: 33(OKT3). In some embodiments, the polynucleotide encoding the antigen-binding domain that binds the protein associated with the TCR complex comprises a nucleotide sequence having at least 85% sequence identity with the nucleotide sequence of SEQ ID NO: 33(OKT3). In some embodiments, the polynucleotide encoding the antigen-binding domain that binds the protein associated with the TCR complex comprises a nucleotide sequence having at least 90% sequence identity with the nucleotide sequence of SEQ ID NO: 33(OKT3). In some embodiments, the polynucleotide encoding the antigen-binding domain that binds the protein associated with the TCR complex comprises a nucleotide sequence having at least 95% sequence identity with the nucleotide sequence of SEQ ID NO: 33(OKT3). In some embodiments, the polynucleotide encoding the antigen-binding domain that binds the protein associated with the TCR complex comprises a nucleotide sequence having at least 96% sequence identity with the nucleotide sequence of SEQ ID NO: 33(OKT3). In some embodiments, the polynucleotide encoding the antigen-binding domain that binds the protein associated with the TCR complex comprises a nucleotide sequence having at least 97% sequence identity with the nucleotide sequence of SEQ ID NO: 33(OKT3). In some embodiments, the polynucleotide encoding the antigen-binding domain that binds the protein associated with the TCR complex comprises a nucleotide sequence having at least 98% sequence identity with the nucleotide sequence of SEQ ID NO: 33(OKT3). In some embodiments, the polynucleotide encoding the antigen-binding domain that binds the protein associated with the TCR complex comprises a nucleotide sequence having at least 99% sequence identity with the nucleotide sequence of SEQ ID NO: 33(OKT3). In some embodiments, the polynucleotide encoding the antigen-binding domain that binds the protein associated with the TCR complex comprises the nucleotide sequence of SEQ ID NO: 33 (OKT3).

In some embodiments, the antigen-binding domain that binds the protein associated with the TCR complex comprises an amino acid sequence having at least 70% sequence identity with the amino acid sequence of SEQ ID NO: 34 (OKT3). In some embodiments, the antigen-binding domain that binds the protein associated with the TCR complex comprises an amino acid sequence having at least 75% sequence identity with the amino acid sequence of SEQ ID NO: 34 (OKT3). In some embodiments, the antigen-binding domain that binds the protein associated with the TCR complex comprises an amino acid sequence having at least 80% sequence identity with the amino acid sequence of SEQ ID NO: 34 (OKT3). In some embodiments, the antigen-binding domain that binds the protein associated with the TCR complex comprises an amino acid sequence having at least 85% sequence identity with the amino acid sequence of SEQ ID NO: 34 (OKT3). In some embodiments, the antigen-binding domain that binds the protein associated with the TCR complex comprises an amino acid sequence having at least 90% sequence identity with the amino acid sequence of SEQ ID NO: 34 (OKT3). In some embodiments, the antigen-binding domain that binds the protein associated with the TCR complex comprises an amino acid sequence having at least 95% sequence identity with the amino acid sequence of SEQ ID NO: 34 (OKT3). In some embodiments, the antigen-binding domain that binds the protein associated with the TCR complex comprises an amino acid sequence having at least 96% sequence identity with the amino acid sequence of SEQ ID NO: 34 (OKT3). In some embodiments, the antigen-binding domain that binds the protein associated with the TCR complex comprises an amino acid sequence having at least 97% sequence identity with the amino acid sequence of SEQ ID NO: 34 (OKT3). In some embodiments, the antigen-binding domain that binds the protein associated with the TCR complex comprises an amino acid sequence having at least 98% sequence identity with the amino acid sequence of SEQ ID NO: 34 (OKT3). In some embodiments, the antigen-binding domain that binds the protein associated with the TCR complex comprises an amino acid sequence having at least 99% sequence identity with the amino acid sequence of SEQ ID NO: 34 (OKT3). In some embodiments, the antigen-binding domain that binds the protein associated with the TCR complex comprises the amino acid sequence of SEQ ID NO: 34 (OKT3). In some embodiments, the CDR sequences of the antigen-binding domain that binds the protein associated with the TCR complex have 100% identity with the CDR sequences of the amino acid sequence of SEQ ID NO: 34 (OKT3) (i.e., the antigen-binding domain that binds the protein associated with the TCR complex comprises an amino acid sequence comprising a CDRH1, CDRH2, CDRH3, CDRL1, CDRL2, and CDRL3, each having 100% identity to the corresponding CDR in the amino acid sequence of SEQ ID NO: 34 (OKT3). In some embodiments, the CDR sequences of the antigen-binding domain that binds the protein associated with the TCR complex have 100% identity with the CDR sequences of the amino acid sequence of SEQ ID NO: 34 (OKT3), and the non-CDR (e.g., framework) sequences of the antigen-binding domain that binds the protein associated with the TCR complex have at least 80% sequence identity with the non-CDR (e.g., framework) sequences of the amino acid sequence of SEQ ID NO: 34 (OKT3). In some embodiments, the CDR sequences of the antigen-binding domain that binds the protein associated with the TCR complex have 100% identity with the CDR sequences of the amino acid sequence of SEQ ID NO: 34 (OKT3), and the non-CDR (e.g., framework) sequences of the antigen-binding domain that binds the protein associated with the TCR complex have at least 85% sequence identity with the non-CDR (e.g., framework) sequences of the amino acid sequence of SEQ ID NO: 34 (OKT3). In some embodiments, the CDR sequences of the antigen-binding domain that binds the protein associated with the TCR complex have 100% identity with the CDR sequences of the amino acid sequence of SEQ ID NO: 34 (OKT3), and the non-CDR (e.g., framework) sequences of the antigen-binding domain that binds the protein associated with the TCR complex have at least 90% sequence identity with the non-CDR (e.g., framework) sequences of the amino acid sequence of SEQ ID NO: 34 (OKT3). In some embodiments, the CDR sequences of the antigen-binding domain that binds the protein associated with the TCR complex have 100% identity with the CDR sequences of the amino acid sequence of SEQ ID NO: 34 (OKT3), and the non-CDR (e.g., framework) sequences of the antigen-binding domain that binds the protein associated with the TCR complex have at least 95% sequence identity with the non-CDR (e.g., framework) sequences of the amino acid sequence of SEQ ID NO: 34 (OKT3). In some embodiments, the CDR sequences of the antigen-binding domain that binds the protein associated with the TCR complex have 100% identity with the CDR sequences of the amino acid sequence of SEQ ID NO: 34 (OKT3), and the non-CDR (e.g., framework) sequences of the antigen-binding domain that binds the protein associated with the TCR complex have at least 96% sequence identity with the non-CDR (e.g., framework) sequences of the amino acid sequence of SEQ ID NO: 34 (OKT3). In some embodiments, the CDR sequences of the antigen-binding domain that binds the protein associated with the TCR complex have 100% identity with the CDR sequences of the amino acid sequence of SEQ ID NO: 34 (OKT3), and the non-CDR (e.g., framework) sequences of the antigen-binding domain that binds the protein associated with the TCR complex have at least 97% sequence identity with the non-CDR (e.g., framework) sequences of the amino acid sequence of SEQ ID NO: 34 (OKT3). In some embodiments, the CDR sequences of the antigen-binding domain that binds the protein associated with the TCR complex have 100% identity with the CDR sequences of the amino acid sequence of SEQ ID NO: 34 (OKT3), and the non-CDR (e.g., framework) sequences of the antigen-binding domain that binds the protein associated with the TCR complex have at least 98% sequence identity with the non-CDR (e.g., framework) sequences of the amino acid sequence of SEQ ID NO: 34 (OKT3). In some embodiments, the CDR sequences of the antigen-binding domain that binds the protein associated with the TCR complex have 100% identity with the CDR sequences of the amino acid sequence of SEQ ID NO: 34 (OKT3), and the non-CDR (e.g., framework) sequences of the antigen-binding domain that binds the protein associated with the TCR complex have at least 99% sequence identity with the non-CDR (e.g., framework) sequences of the amino acid sequence of SEQ ID NO: 34 (OKT3).

In some embodiments, the antigen-binding domain that binds to the protein associated with the TCR complex is F6A. In some embodiments, the murine F6A antigen-binding domain is encoded by SEQ ID NO: 35. In some embodiments, the F6A antigen-binding domain comprises SEQ ID NO: 36.

In some embodiments, the polynucleotide encoding the antigen-binding domain that binds the protein associated with the TCR complex comprises a nucleotide sequence having at least 70% sequence identity with the nucleotide sequence of SEQ ID NO: 35(F6A). In some embodiments, the polynucleotide encoding the antigen-binding domain that binds the protein associated with the TCR complex comprises a nucleotide sequence having at least 75% sequence identity with the nucleotide sequence of SEQ ID NO: 35(F6A). In some embodiments, the polynucleotide encoding the antigen-binding domain that binds the protein associated with the TCR complex comprises a nucleotide sequence having at least 80% sequence identity with the nucleotide sequence of SEQ ID NO: 35(F6A). In some embodiments, the polynucleotide encoding the antigen-binding domain that binds the protein associated with the TCR complex comprises a nucleotide sequence having at least 85% sequence identity with the nucleotide sequence of SEQ ID NO: 35(F6A). In some embodiments, the polynucleotide encoding the antigen-binding domain that binds the protein associated with the TCR complex comprises a nucleotide sequence having at least 90% sequence identity with the nucleotide sequence of SEQ ID NO: 35(F6A). In some embodiments, the polynucleotide encoding the antigen-binding domain that binds the protein associated with the TCR complex comprises a nucleotide sequence having at least 95% sequence identity with the nucleotide sequence of SEQ ID NO: 35(F6A). In some embodiments, the polynucleotide encoding the antigen-binding domain that binds the protein associated with the TCR complex comprises a nucleotide sequence having at least 96% sequence identity with the nucleotide sequence of SEQ ID NO: 35(F6A). In some embodiments, the polynucleotide encoding the antigen-binding domain that binds the protein associated with the TCR complex comprises a nucleotide sequence having at least 97% sequence identity with the nucleotide sequence of SEQ ID NO: 35 (F6A). In some embodiments, the polynucleotide encoding the antigen-binding domain that binds the protein associated with the TCR complex comprises a nucleotide sequence having at least 98% sequence identity with the nucleotide sequence of SEQ ID NO: 35(F6A). In some embodiments, the polynucleotide encoding the antigen-binding domain that binds the protein associated with the TCR complex comprises a nucleotide sequence having at least 99% sequence identity with the nucleotide sequence of SEQ ID NO: 35(F6A). In some embodiments, the polynucleotide encoding the antigen-binding domain that binds the protein associated with the TCR complex comprises the nucleotide sequence of SEQ ID NO: 35(F6A).

In some embodiments, the antigen-binding domain that binds the protein associated with the TCR complex comprises an amino acid sequence having at least 70% sequence identity with the amino acid sequence of SEQ ID NO: 36 (F6A). In some embodiments, the antigen-binding domain that binds the protein associated with the TCR complex comprises an amino acid sequence having at least 75% sequence identity with the amino acid sequence of SEQ ID NO: 36 (F6A). In some embodiments, the antigen-binding domain that binds the protein associated with the TCR complex comprises an amino acid sequence having at least 80% sequence identity with the amino acid sequence of SEQ ID NO: 36 (F6A). In some embodiments, the antigen-binding domain that binds the protein associated with the TCR complex comprises an amino acid sequence having at least 85% sequence identity with the amino acid sequence of SEQ ID NO: 36 (F6A). In some embodiments, the antigen-binding domain that binds the protein associated with the TCR complex comprises an amino acid sequence having at least 90% sequence identity with the amino acid sequence of SEQ ID NO: 36 (F6A). In some embodiments, the antigen-binding domain that binds the protein associated with the TCR complex comprises an amino acid sequence having at least 95% sequence identity with the amino acid sequence of SEQ ID NO: 36 (F6A). In some embodiments, the antigen-binding domain that binds the protein associated with the TCR complex comprises an amino acid sequence having at least 96% sequence identity with the amino acid sequence of SEQ ID NO: 36 (F6A). In some embodiments, the antigen-binding domain that binds the protein associated with the TCR complex comprises an amino acid sequence having at least 97% sequence identity with the amino acid sequence of SEQ ID NO: 36 (F6A). In some embodiments, the antigen-binding domain that binds the protein associated with the TCR complex comprises an amino acid sequence having at least 98% sequence identity with the amino acid sequence of SEQ ID NO: 36 (F6A). In some embodiments, the antigen-binding domain that binds the protein associated with the TCR complex comprises an amino acid sequence having at least 99% sequence identity with the amino acid sequence of SEQ ID NO: 36 (F6A). In some embodiments, the antigen-binding domain that binds the protein associated with the TCR complex comprises the amino acid sequence of SEQ ID NO: 36 (F6A). In some embodiments, the CDR sequences of the antigen-binding domain that binds the protein associated with the TCR complex have 100% identity with the CDR sequences of the amino acid sequence of SEQ ID NO: 36 (F6A) (i.e., the antigen-binding domain that binds the protein associated with the TCR complex comprises an amino acid sequence comprising a CDRH1, CDRH2, CDRH3, CDRL1, CDRL2, and CDRL3, each having 100% identity to the corresponding CDR in the amino acid sequence of SEQ ID NO: 36 (F6A). In some embodiments, the CDR sequences of the antigen-binding domain that binds the protein associated with the TCR complex have 100% identity with the CDR sequences of the amino acid sequence of SEQ ID NO: 36 (F6A), and the non-CDR (e.g., framework) sequences of the antigen-binding domain that binds the protein associated with the TCR complex have at least 80% sequence identity with the non-CDR (e.g., framework) sequences of the amino acid sequence of SEQ ID NO: 36 (F6A). In some embodiments, the CDR sequences of the antigen-binding domain that binds the protein associated with the TCR complex have 100% identity with the CDR sequences of the amino acid sequence of SEQ ID NO: 36 (F6A), and the non-CDR (e.g., framework) sequences of the antigen-binding domain that binds the protein associated with the TCR complex have at least 85% sequence identity with the non-CDR (e.g., framework) sequences of the amino acid sequence of SEQ ID NO: 36 (F6A). In some embodiments, the CDR sequences of the antigen-binding domain that binds the protein associated with the TCR complex have 100% identity with the CDR sequences of the amino acid sequence of SEQ ID NO: 36 (F6A), and the non-CDR (e.g., framework) sequences of the antigen-binding domain that binds the protein associated with the TCR complex have at least 90% sequence identity with the non-CDR (e.g., framework) sequences of the amino acid sequence of SEQ ID NO: 36 (F6A). In some embodiments, the CDR sequences of the antigen-binding domain that binds the protein associated with the TCR complex have 100% identity with the CDR sequences of the amino acid sequence of SEQ ID NO: 36 (F6A), and the non-CDR (e.g., framework) sequences of the antigen-binding domain that binds the protein associated with the TCR complex have at least 95% sequence identity with the non-CDR (e.g., framework) sequences of the amino acid sequence of SEQ ID NO: 36 (F6A). In some embodiments, the CDR sequences of the antigen-binding domain that binds the protein associated with the TCR complex have 100% identity with the CDR sequences of the amino acid sequence of SEQ ID NO: 36 (F6A), and the non-CDR (e.g., framework) sequences of the antigen-binding domain that binds the protein associated with the TCR complex have at least 96% sequence identity with the non-CDR (e.g., framework) sequences of the amino acid sequence of SEQ ID NO: 36 (F6A). In some embodiments, the CDR sequences of the antigen-binding domain that binds the protein associated with the TCR complex have 100% identity with the CDR sequences of the amino acid sequence of SEQ ID NO: 36 (F6A), and the non-CDR (e.g., framework) sequences of the antigen-binding domain that binds the protein associated with the TCR complex have at least 97% sequence identity with the non-CDR (e.g., framework) sequences of the amino acid sequence of SEQ ID NO: 36 (F6A). In some embodiments, the CDR sequences of the antigen-binding domain that binds the protein associated with the TCR complex have 100% identity with the CDR sequences of the amino acid sequence of SEQ ID NO: 36 (F6A), and the non-CDR (e.g., framework) sequences of the antigen-binding domain that binds the protein associated with the TCR complex have at least 98% sequence identity with the non-CDR (e.g., framework) sequences of the amino acid sequence of SEQ ID NO: 36 (F6A). In some embodiments, the CDR sequences of the antigen-binding domain that binds the protein associated with the TCR complex have 100% identity with the CDR sequences of the amino acid sequence of SEQ ID NO: 36 (F6A), and the non-CDR (e.g., framework) sequences of the antigen-binding domain that binds the protein associated with the TCR complex have at least 99% sequence identity with the non-CDR (e.g., framework) sequences of the amino acid sequence of SEQ ID NO: 36 (F6A).

In some embodiments, the antigen-binding domain that binds to the protein associated with the TCR complex is L2K. In some embodiments, the murine L2K antigen-binding domain is encoded by SEQ ID NO: 37. In some embodiments, the L2K antigen-binding domain comprises SEQ ID NO: 38.

In some embodiments, the polynucleotide encoding the antigen-binding domain that binds the protein associated with the TCR complex comprises a nucleotide sequence having at least 70% sequence identity with the nucleotide sequence of SEQ ID NO: 37 (L2K). In some embodiments, the polynucleotide encoding the antigen-binding domain that binds the protein associated with the TCR complex comprises a nucleotide sequence having at least 75% sequence identity with the nucleotide sequence of SEQ ID NO: 37 (L2K). In some embodiments, the polynucleotide encoding the antigen-binding domain that binds the protein associated with the TCR complex comprises a nucleotide sequence having at least 80% sequence identity with the nucleotide sequence of SEQ ID NO: 37 (L2K). In some embodiments, the polynucleotide encoding the antigen-binding domain that binds the protein associated with the TCR complex comprises a nucleotide sequence having at least 85% sequence identity with the nucleotide sequence of SEQ ID NO: 37 (L2K). In some embodiments, the polynucleotide encoding the antigen-binding domain that binds the protein associated with the TCR complex comprises a nucleotide sequence having at least 90% sequence identity with the nucleotide sequence of SEQ ID NO: 37 (L2K). In some embodiments, the polynucleotide encoding the antigen-binding domain that binds the protein associated with the TCR complex comprises a nucleotide sequence having at least 95% sequence identity with the nucleotide sequence of SEQ ID NO: 37 (L2K). In some embodiments, the polynucleotide encoding the antigen-binding domain that binds the protein associated with the TCR complex comprises a nucleotide sequence having at least 96% sequence identity with the nucleotide sequence of SEQ ID NO: 37 (L2K). In some embodiments, the polynucleotide encoding the antigen-binding domain that binds the protein associated with the TCR complex comprises a nucleotide sequence having at least 97% sequence identity with the nucleotide sequence of SEQ ID NO: 37 (L2K). In some embodiments, the polynucleotide encoding the antigen-binding domain that binds the protein associated with the TCR complex comprises a nucleotide sequence having at least 98% sequence identity with the nucleotide sequence of SEQ ID NO: 37 (L2K). In some embodiments, the polynucleotide encoding the antigen-binding domain that binds the protein associated with the TCR complex comprises a nucleotide sequence having at least 99% sequence identity with the nucleotide sequence of SEQ ID NO: 37 (L2K). In some embodiments, the polynucleotide encoding the antigen-binding domain that binds the protein associated with the TCR complex comprises the nucleotide sequence of SEQ ID NO: 37 (L2K).

In some embodiments, the antigen-binding domain that binds the protein associated with the TCR complex comprises an amino acid sequence having at least 70% sequence identity with the amino acid sequence of SEQ ID NO: 38 (L2K). In some embodiments, the antigen-binding domain that binds the protein associated with the TCR complex comprises an amino acid sequence having at least 75% sequence identity with the amino acid sequence of SEQ ID NO: 38 (L2K). In some embodiments, the antigen-binding domain that binds the protein associated with the TCR complex comprises an amino acid sequence having at least 80% sequence identity with the amino acid sequence of SEQ ID NO: 38 (L2K). In some embodiments, the antigen-binding domain that binds the protein associated with the TCR complex comprises an amino acid sequence having at least 85% sequence identity with the amino acid sequence of SEQ ID NO: 38 (L2K). In some embodiments, the antigen-binding domain that binds the protein associated with the TCR complex comprises an amino acid sequence having at least 90% sequence identity with the amino acid sequence of SEQ ID NO: 38 (L2K). In some embodiments, the antigen-binding domain that binds the protein associated with the TCR complex comprises an amino acid sequence having at least 95% sequence identity with the amino acid sequence of SEQ ID NO: 38 (L2K). In some embodiments, the antigen-binding domain that binds the protein associated with the TCR complex comprises an amino acid sequence having at least 96% sequence identity with the amino acid sequence of SEQ ID NO: 38 (L2K). In some embodiments, the antigen-binding domain that binds the protein associated with the TCR complex comprises an amino acid sequence having at least 97% sequence identity with the amino acid sequence of SEQ ID NO: 38 (L2K). In some embodiments, the antigen-binding domain that binds the protein associated with the TCR complex comprises an amino acid sequence having at least 98% sequence identity with the amino acid sequence of SEQ ID NO: 38 (L2K). In some embodiments, the antigen-binding domain that binds the protein associated with the TCR complex comprises an amino acid sequence having at least 99% sequence identity with the amino acid sequence of SEQ ID NO: 38 (L2K). In some embodiments, the antigen-binding domain that binds the protein associated with the TCR complex comprises the amino acid sequence of SEQ ID NO: 38 (L2K). In some embodiments, the CDR sequences of the antigen-binding domain that binds the protein associated with the TCR complex have 100% identity with the CDR sequences of the amino acid sequence of SEQ ID NO: 38 (L2K) (i.e., the antigen-binding domain that binds the protein associated with the TCR complex comprises an amino acid sequence comprising a CDRH1, CDRH2, CDRH3, CDRL1, CDRL2, and CDRL3, each having 100% identity to the corresponding CDR in the amino acid sequence of SEQ ID NO: 38 (L2K). In some embodiments, the CDR sequences of the antigen-binding domain that binds the protein associated with the TCR complex have 100% identity with the CDR sequences of the amino acid sequence of SEQ ID NO: 38 (L2K), and the non-CDR (e.g., framework) sequences of the antigen-binding domain that binds the protein associated with the TCR complex have at least 80% sequence identity with the non-CDR (e.g., framework) sequences of the amino acid sequence of SEQ ID NO: 38 (L2K). In some embodiments, the CDR sequences of the antigen-binding domain that binds the protein associated with the TCR complex have 100% identity with the CDR sequences of the amino acid sequence of SEQ ID NO: 38 (L2K), and the non-CDR (e.g., framework) sequences of the antigen-binding domain that binds the protein associated with the TCR complex have at least 85% sequence identity with the non-CDR (e.g., framework) sequences of the amino acid sequence of SEQ ID NO: 38 (L2K). In some embodiments, the CDR sequences of the antigen-binding domain that binds the protein associated with the TCR complex have 100% identity with the CDR sequences of the amino acid sequence of SEQ ID NO: 38 (L2K), and the non-CDR (e.g., framework) sequences of the antigen-binding domain that binds the protein associated with the TCR complex have at least 90% sequence identity with the non-CDR (e.g., framework) sequences of the amino acid sequence of SEQ ID NO: 38 (L2K). In some embodiments, the CDR sequences of the antigen-binding domain that binds the protein associated with the TCR complex have 100% identity with the CDR sequences of the amino acid sequence of SEQ ID NO: 38 (L2K), and the non-CDR (e.g., framework) sequences of the antigen-binding domain that binds the protein associated with the TCR complex have at least 95% sequence identity with the non-CDR (e.g., framework) sequences of the amino acid sequence of SEQ ID NO: 38 (L2K). In some embodiments, the CDR sequences of the antigen-binding domain that binds the protein associated with the TCR complex have 100% identity with the CDR sequences of the amino acid sequence of SEQ ID NO: 38 (L2K), and the non-CDR (e.g., framework) sequences of the antigen-binding domain that binds the protein associated with the TCR complex have at least 96% sequence identity with the non-CDR (e.g., framework) sequences of the amino acid sequence of SEQ ID NO: 38 (L2K). In some embodiments, the CDR sequences of the antigen-binding domain that binds the protein associated with the TCR complex have 100% identity with the CDR sequences of the amino acid sequence of SEQ ID NO: 38 (L2K), and the non-CDR (e.g., framework) sequences of the antigen-binding domain that binds the protein associated with the TCR complex have at least 97% sequence identity with the non-CDR (e.g., framework) sequences of the amino acid sequence of SEQ ID NO: 38 (L2K). In some embodiments, the CDR sequences of the antigen-binding domain that binds the protein associated with the TCR complex have 100% identity with the CDR sequences of the amino acid sequence of SEQ ID NO: 38 (L2K), and the non-CDR (e.g., framework) sequences of the antigen-binding domain that binds the protein associated with the TCR complex have at least 98% sequence identity with the non-CDR (e.g., framework) sequences of the amino acid sequence of SEQ ID NO: 38 (L2K). In some embodiments, the CDR sequences of the antigen-binding domain that binds the protein associated with the TCR complex have 100% identity with the CDR sequences of the amino acid sequence of SEQ ID NO: 38 (L2K), and the non-CDR (e.g., framework) sequences of the antigen-binding domain that binds the protein associated with the TCR complex have at least 99% sequence identity with the non-CDR (e.g., framework) sequences of the amino acid sequence of SEQ ID NO: 38 (L2K).

Amino acid and nucleotide sequences of exemplary antigen-binding domains that bind a protein associated with the TCR complex are provided in Table 2.

TABLE 2

Table of Sequences

| SEQ ID NO | Description | Nucleotide/Amino Acid |
|---|---|---|
| SEQ ID NO: 31 | UCHT1[1] | Nucleotide |
| SEQ ID NO: 32 | UCHT1[2] | Amino Acid |
| SEQ ID NO: 33 | OKT3 | Nucleotide |
| SEQ ID NO: 34 | OKT3 | Amino Acid |
| SEQ ID NO: 35 | F6A | Nucleotide |
| SEQ ID NO: 36 | F6A | Amino Acid |
| SEQ ID NO: 37 | L2K | Nucleotide |
| SEQ ID NO: 38 | L2K | Amino Acid |
| SEQ ID NO: 39 | huUCHT1 | Nucleotide |
| SEQ ID NO: 40 | huUCHT1 | Amino Acid |
| SEQ ID NO: 41 | huUCHT1 (Y177T) | Nucleotide |
| SEQ ID NO: 42 | huUCHT1 (Y177T) | Amino Acid |
| SEQ ID NO: 43 | UCHT1 (Y182T) | Nucleotide |
| SEQ ID NO: 44 | UCHT1 (Y182T) | Amino Acid |

[1]Light chain, nucleotides 1-324; Linker, nucleotides 325-387; Heavy chain, nucleotides 388-750
[2]Light chain, amino acids 1-108; Linker, amino acids 109-128; Heavy chain, amino acids 129-250

Transmembrane Domain and Cytosolic Domain

In some embodiments, a BCMA T cell antigen coupler polypeptide comprises a T cell receptor signaling domain polypeptide. In some embodiments, a BCMA T cell antigen coupler polypeptide comprises a transmembrane domain of a TCR signaling domain. In some embodiments, a BCMA T cell antigen coupler polypeptide comprises a cytosolic domain of a TCR signaling domain polypeptide. In some embodiments, a BCMA T cell antigen coupler polypeptide comprises a transmembrane domain and a cytosolic domain of a TCR signaling domain polypeptide.

In some embodiments, the T cell receptor signaling domain polypeptide comprises a TCR co-receptor domain. In some embodiments, the TCR signaling domain polypeptide comprises a transmembrane domain and/or a cytosolic domain of a TCR co-receptor. In some embodiments, the TCR co-receptor is CD4, CD8, LAG3, or a chimeric variation thereof.

In some embodiments, the TCR co-receptor is CD4. In some embodiments, the BCMA TAC comprises a transmembrane domain and a cytosolic domain of a CD4 co-receptor. In some embodiments, the polynucleotide encoding the cytosolic and transmembrane domain comprises a nucleotide sequence having at least 70% sequence identity with the nucleotide sequence of SEQ ID NO: 45 (CD4 transmembrane and cytosolic domain). In some embodiments, the polynucleotide encoding the cytosolic and transmembrane domain comprises a nucleotide sequence having at least 75% sequence identity with the nucleotide sequence of SEQ ID NO: 45 (CD4 transmembrane and cytosolic domain). In some embodiments, the polynucleotide encoding the cytosolic and transmembrane domain comprises a nucleotide sequence having at least 80% sequence identity with the nucleotide sequence of SEQ ID NO: 45 (CD4 transmembrane and cytosolic domain). In some embodiments, the polynucleotide encoding the cytosolic and transmembrane domain comprises a nucleotide sequence having at least 85% sequence identity with the nucleotide sequence of SEQ ID NO: 45 (CD4 transmembrane and cytosolic domain). In some embodiments, the polynucleotide encoding the cytosolic and transmembrane domain comprises a nucleotide sequence having at least 90% sequence identity with the nucleotide sequence of SEQ ID NO: 45 (CD4 transmembrane and cytosolic domain). In some embodiments, the polynucleotide encoding the cytosolic and transmembrane domain comprises a nucleotide sequence having at least 95% sequence identity with the nucleotide sequence of SEQ ID NO: 45 (CD4 transmembrane and cytosolic domain). In some embodiments, the polynucleotide encoding the cytosolic and transmembrane domain comprises a nucleotide sequence having at least 96% sequence identity with the nucleotide sequence of SEQ ID NO: 45 (CD4 transmembrane and cytosolic domain). In some embodiments, the polynucleotide encoding the cytosolic and transmembrane domain comprises a nucleotide sequence having at least 97% sequence identity with the nucleotide sequence of SEQ ID NO: 45 (CD4 transmembrane and cytosolic domain). In some embodiments, the polynucleotide encoding the cytosolic and transmembrane domain comprises a nucleotide sequence having at least 98% sequence identity with the nucleotide sequence of SEQ ID NO: 45 (CD4 transmembrane and cytosolic domain). In some embodiments, the polynucleotide encoding the cytosolic and transmembrane domain comprises a nucleotide sequence having at least 99% sequence identity with the nucleotide sequence of SEQ ID NO: 45 (CD4 transmembrane and cytosolic domain). In some embodiments, the polynucleotide encoding the cytosolic and transmembrane domain comprises the nucleotide sequence of SEQ ID NO: 45 (CD4 transmembrane and cytosolic domain). In some embodiments, the cytosolic and transmembrane domain comprise an amino acid sequence having at least 70% sequence identity with the amino acid sequence of SEQ ID NO: 46 (CD4 transmembrane and cytosolic domain). In some embodiments, the cytosolic and transmembrane domain comprise an amino acid sequence having at least 75% sequence identity with the amino acid sequence of SEQ ID NO: 46 (CD4 transmembrane and cytosolic domain). In some embodiments, the cytosolic and transmembrane domain comprise an amino acid sequence having at least 80% sequence identity with the amino acid sequence of SEQ ID NO: 46 (CD4 transmembrane and cytosolic domain). In some embodiments, the cytosolic and transmembrane domain comprise an amino acid sequence having at least 85% sequence identity with the amino acid sequence of SEQ ID NO: 46 (CD4 transmembrane and cytosolic domain). In some embodiments, the cytosolic and transmembrane domain comprise an amino acid sequence having at least 90% sequence identity with the amino acid sequence of SEQ ID NO: 46 (CD4 transmembrane and cytosolic domain). In some embodiments, the cytosolic and transmembrane domain comprise an amino acid sequence having at least 95% sequence identity with the amino acid sequence of SEQ ID NO: 46 (CD4 transmembrane and cytosolic domain). In some embodiments, the cytosolic and transmembrane domain comprise an amino acid sequence having at least 96% sequence identity with the amino acid sequence of SEQ ID NO: 46 (CD4 transmembrane and cytosolic domain). In some embodiments, the cytosolic and transmembrane domain comprise an amino acid sequence having at least 97% sequence identity with the amino acid sequence of SEQ ID NO: 46 (CD4 transmembrane and cytosolic domain). In some embodiments, the cytosolic and transmembrane domain comprise an amino acid sequence having at least 98% sequence identity with the amino acid sequence of SEQ ID NO: 46 (CD4 transmembrane and cytosolic domain). In some embodiments, the cytosolic and transmembrane domain comprise an amino acid sequence having at least 99% sequence identity with the amino acid sequence of SEQ ID NO: 46 (CD4 transmembrane and cytosolic domain). In some embodiments, the cytosolic and transmembrane domain comprise the amino acid sequence of SEQ ID NO: 46 (CD4 transmembrane and cytosolic domain).

In some embodiments, the TCR co-receptor is CD8. In some embodiments, the TCR co-receptor is CD8α. In some embodiments, the polynucleotide encoding the cytosolic and transmembrane domain comprises a nucleotide sequence having at least 70% sequence identity with the nucleotide sequence of SEQ ID NO: 47 (CD8 transmembrane and cytosolic domain). In some embodiments, the polynucleotide encoding the cytosolic and transmembrane domain comprises a nucleotide sequence having at least 75% sequence identity with the nucleotide sequence of SEQ ID NO: 47 (CD8 transmembrane and cytosolic domain). In some embodiments, the polynucleotide encoding the cytosolic and transmembrane domain comprises a nucleotide sequence having at least 80% sequence identity with the nucleotide sequence of SEQ ID NO: 47 (CD8 transmembrane and cytosolic domain). In some embodiments, the polynucleotide encoding the cytosolic and transmembrane domain comprises a nucleotide sequence having at least 85% sequence identity with the nucleotide sequence of SEQ ID NO: 47 (CD8 transmembrane and cytosolic domain). In some embodiments, the polynucleotide encoding the cytosolic and transmembrane domain comprises a nucleotide sequence having at least 90% sequence identity with the nucleotide sequence of SEQ ID NO: 47 (CD8 transmembrane and cytosolic domain). In some embodiments, the polynucleotide encoding the cytosolic and transmembrane domain comprises a nucleotide sequence having at least 95% sequence identity with the nucleotide sequence of SEQ ID NO: 47 (CD8 transmembrane and cytosolic domain). In some embodiments, the polynucleotide encoding the cytosolic and transmembrane domain comprises a nucleotide sequence having at least 96% sequence identity with the nucleotide sequence of SEQ ID NO: 47 (CD8 transmembrane and cytosolic domain). In some embodiments, the polynucleotide encoding the cytosolic and transmembrane domain comprises a nucleotide sequence having at least 97% sequence identity with the nucleotide sequence of SEQ ID NO: 47 (CD8 transmembrane and cytosolic domain). In some embodiments, the polynucleotide encoding the cytosolic and transmembrane domain comprises a nucleotide sequence having at least 98% sequence identity with the nucleotide sequence of SEQ ID NO: 47 (CD8 transmembrane and cytosolic domain). In some embodiments, the polynucleotide encoding the cytosolic and transmembrane domain comprises a nucleotide sequence having at least 99% sequence identity with the nucleotide sequence of SEQ ID NO: 47 (CD8 transmembrane and cytosolic domain). In some embodiments, the polynucleotide encoding the cytosolic and transmembrane domain comprises the nucleotide sequence of SEQ ID NO: 47 (CD8 transmembrane and cytosolic domain). In some embodiments, the cytosolic and transmembrane domain comprise an amino acid sequence having at least 70% sequence identity with the amino acid sequence of SEQ ID NO: 48 (CD8 transmembrane and cytosolic domain). In some embodiments, the cytosolic and transmembrane domain comprise an amino acid sequence having at least 75% sequence identity with the amino acid sequence of SEQ ID NO: 48 (CD8 transmembrane and cytosolic domain). In some embodiments, the cytosolic and transmembrane domain comprise an amino acid sequence having at least 80% sequence identity with the amino acid sequence of SEQ ID NO: 48 (CD8 transmembrane and cytosolic domain). In some embodiments, the cytosolic and transmembrane domain comprise an amino acid sequence having at least 85% sequence identity with the amino acid sequence of SEQ ID NO: 48 (CD8 transmembrane and cytosolic domain). In some embodiments, the cytosolic and transmembrane domain comprise an amino acid sequence having at least 90% sequence identity with the amino acid sequence of SEQ ID NO: 48 (CD8 transmembrane and cytosolic domain). In some embodiments, the cytosolic and transmembrane domain comprise an amino acid sequence having at least 95% sequence identity with the amino acid sequence of SEQ ID NO: 48 (CD8 transmembrane and cytosolic domain). In some embodiments, the cytosolic and transmembrane domain comprise an amino acid sequence having at least 96% sequence identity with the amino acid sequence of SEQ ID NO: 48 (CD8 transmembrane and cytosolic domain). In some embodiments, the cytosolic and transmembrane domain comprise an amino acid sequence having at least 97% sequence identity with the amino acid sequence of SEQ ID NO: 48 (CD8 transmembrane and cytosolic domain). In some embodiments, the cytosolic and transmembrane domain comprise an amino acid sequence having at least 98% sequence identity with the amino acid sequence of SEQ ID NO: 48 (CD8 transmembrane and cytosolic domain). In some embodiments, the cytosolic and transmembrane domain comprise an amino acid sequence having at least 99% sequence identity with the amino acid sequence of SEQ ID NO: 48 (CD8 transmembrane and cytosolic domain). In some embodiments, the cytosolic and transmembrane domain comprise the amino acid sequence of SEQ ID NO: 48 (CD8 transmembrane and cytosolic domain).

In some embodiments, the TCR signaling domain polypeptide comprises a chimera of sequences or domains from co-receptors. In some embodiments, the TCR signaling domain polypeptide comprises a chimera of CD8a and CD8β, wherein the CD8a arginine rich region is replaced with the CD8β arginine rich region (CD8α+R(β) chimera). In some embodiments, the polynucleotide encoding the cytosolic and transmembrane domain comprises a nucleotide sequence having at least 70% sequence identity with the nucleotide sequence of SEQ ID NO: 49 (CD8α+R(β) chimera). In some embodiments, the polynucleotide encoding the cytosolic and transmembrane domain comprises a nucleotide sequence having at least 75% sequence identity with the nucleotide sequence of SEQ ID NO: 49 (CD8α+R(β) chimera). In some embodiments, the polynucleotide encoding the cytosolic and transmembrane domain comprises a nucleotide sequence having at least 80% sequence identity with the nucleotide sequence of SEQ ID NO: 49 (CD8α+R(β) chimera). In some embodiments, the polynucleotide encoding the cytosolic and transmembrane domain comprises a nucleotide sequence having at least 85% sequence identity with the nucleotide sequence of SEQ ID NO: 49 (CD8α+R(β) chimera). In some embodiments, the polynucleotide encoding the cytosolic and transmembrane domain comprises a nucleotide sequence having at least 90% sequence identity with the nucleotide sequence of SEQ ID NO: 49 (CD8α+R(β) chimera). In some embodiments, the polynucleotide encoding the cytosolic and transmembrane domain comprises a nucleotide sequence having at least 95% sequence identity with the nucleotide sequence of SEQ ID NO: 49 (CD8α+R(β) chimera). In some embodiments, the polynucleotide encoding the cytosolic and transmembrane domain comprises a nucleotide sequence having at least 96% sequence identity with the nucleotide sequence of SEQ ID NO: 49 (CD8α+R(β) chimera). In some embodiments, the polynucleotide encoding the cytosolic and transmembrane domain comprises a nucleotide sequence having at least 97% sequence identity with the nucleotide sequence of SEQ ID NO: 49 (CD8α+R(β) chimera). In some embodiments, the polynucleotide encoding the cytosolic and transmembrane domain comprises a nucleotide sequence having at least 98% sequence identity with the nucleotide sequence of SEQ ID NO: 49 (CD8α+R(β) chimera). In some embodiments, the polynucleotide encoding the cytosolic and transmembrane domain comprises a nucleotide sequence having at least 99% sequence identity with the nucleotide sequence of SEQ ID NO: 49 (CD8α+R(β) chimera). In some embodiments, the polynucleotide encoding the cytosolic and transmembrane domain comprises the nucleotide sequence of SEQ ID NO: 49 (CD8α+R(β) chimera). In some embodiments, the cytosolic and transmembrane domain comprise an amino acid sequence having at least 70% sequence identity with the amino acid sequence of SEQ ID NO: 50 (CD8α+R(β) chimera). In some embodiments, the cytosolic and transmembrane domain comprise an amino acid sequence having at least 75% sequence identity with the amino acid sequence of SEQ ID NO: 50 (CD8α+R(β) chimera). In some embodiments, the cytosolic and transmembrane domain comprise an amino acid sequence having at least 80% sequence identity with the amino acid sequence of SEQ ID NO: 50 (CD8α+R(β) chimera). In some embodiments, the cytosolic and transmembrane domain comprise an amino acid sequence having at least 85% sequence identity with the amino acid sequence of SEQ ID NO: 50 (CD8α+R(β) chimera). In some embodiments, the cytosolic and transmembrane domain comprise an amino acid sequence having at least 90% sequence identity with the amino acid sequence of SEQ ID NO: 50 (CD8α+R(β) chimera). In some embodiments, the cytosolic and transmembrane domain comprise an amino acid sequence having at least 95% sequence identity with the amino acid sequence of SEQ ID NO: 50 (CD8α+R(β) chimera). In some embodiments, the cytosolic and transmembrane domain comprise an amino acid sequence having at least 96% sequence identity with the amino acid sequence of SEQ ID NO: 50 (CD8α+R(β) chimera). In some embodiments, the cytosolic and transmembrane domain comprise an amino acid sequence having at least 97% sequence identity with the amino acid sequence of SEQ ID NO: 50 (CD8α+R(β) chimera). In some embodiments, the cytosolic and transmembrane domain comprise an amino acid sequence having at least 98% sequence identity with the amino acid sequence of SEQ ID NO: 50 (CD8α+R(β) chimera). In some embodiments, the cytosolic and transmembrane domain comprise an amino acid sequence having at least 99% sequence identity with the amino acid sequence of SEQ ID NO: 50 (CD8α+R(β) chimera). In some embodiments, the cytosolic and transmembrane domain comprise the amino acid sequence of SEQ ID NO: 50 (CD8α+R(β) chimera).

In some embodiments, the TCR signaling domain polypeptide comprises a chimera of CD8a and CD8β, where the CD8a CXCP domain, which contains an Lck binding motif, is appended to the C-terminus of the CD8β cytosolic domain (CD8β+Lck chimera). In some embodiments, the polynucleotide encoding the cytosolic and transmembrane domain comprises a nucleotide sequence having at least 70% sequence identity with the nucleotide sequence of SEQ ID NO: 51 (CD8β+Lck chimera). In some embodiments, the polynucleotide encoding the cytosolic and transmembrane domain comprises a nucleotide sequence having at least 75% sequence identity with the nucleotide sequence of SEQ ID NO: 51 (CD8β+Lck chimera). In some embodiments, the polynucleotide encoding the cytosolic and transmembrane domain comprises a nucleotide sequence having at least 80% sequence identity with the nucleotide sequence of SEQ ID NO: 51 (CD8β+Lck chimera). In some embodiments, the polynucleotide encoding the cytosolic and transmembrane domain comprises a nucleotide sequence having at least 85% sequence identity with the nucleotide sequence of SEQ ID NO: 51 (CD8β+Lck chimera). In some embodiments, the polynucleotide encoding the cytosolic and transmembrane domain comprises a nucleotide sequence having at least 90% sequence identity with the nucleotide sequence of SEQ ID NO: 51 (CD8β+Lck chimera). In some embodiments, the polynucleotide encoding the cytosolic and transmembrane domain comprises a nucleotide sequence having at least 95% sequence identity with the nucleotide sequence of SEQ ID NO: 51 (CD8β+Lck chimera). In some embodiments, the polynucleotide encoding the cytosolic and transmembrane domain comprises a nucleotide sequence having at least 96% sequence identity with the nucleotide sequence of SEQ ID NO: 51 (CD8β+Lck chimera). In some embodiments, the polynucleotide encoding the cytosolic and transmembrane domain comprises a nucleotide sequence having at least 97% sequence identity with the nucleotide sequence of SEQ ID NO: 51 (CD8β+Lck chimera). In some embodiments, the polynucleotide encoding the cytosolic and transmembrane domain comprises a nucleotide sequence having at least 98% sequence identity with the nucleotide sequence of SEQ ID NO: 51 (CD8β+Lck chimera). In some embodiments, the polynucleotide encoding the cytosolic and transmembrane domain comprises a nucleotide sequence having at least 99% sequence identity with the nucleotide sequence of SEQ ID NO: 51 (CD8β+Lck chimera). In some embodiments, the polynucleotide encoding the cytosolic and transmembrane domain comprises the nucleotide sequence of SEQ ID NO: 51 (CD8β+Lck chimera). In some embodiments, the cytosolic and transmembrane domain comprise an amino acid sequence having at least 70% sequence identity with the amino acid sequence of SEQ ID NO: 52 (CD8β+Lck chimera). In some embodiments, the cytosolic and transmembrane domain comprise an amino acid sequence having at least 75% sequence identity with the amino acid sequence of SEQ ID NO: 52 (CD8β+Lck chimera). In some embodiments, the cytosolic and transmembrane domain comprise an amino acid sequence having at least 80% sequence identity with the amino acid sequence of SEQ ID NO: 52 (CD8β+Lck chimera). In some embodiments, the cytosolic and transmembrane domain comprise an amino acid sequence having at least 85% sequence identity with the amino acid sequence of SEQ ID NO: 52 (CD8β+Lck chimera). In some embodiments, the cytosolic and transmembrane domain comprise an amino acid sequence having at least 90% sequence identity with the amino acid sequence of SEQ ID NO: 52 (CD8β+Lck chimera). In some embodiments, the cytosolic and transmembrane domain comprise an amino acid sequence having at least 95% sequence identity with the amino acid sequence of SEQ ID NO: 52 (CD8β+Lck chimera). In some embodiments, the cytosolic and transmembrane domain comprise an amino acid sequence having at least 96% sequence identity with the amino acid sequence of SEQ ID NO: 52 (CD8β+Lck chimera). In some embodiments, the cytosolic and transmembrane domain comprise an amino acid sequence having at least 97% sequence identity with the amino acid sequence of SEQ ID NO: 52 (CD8β+Lck chimera). In some embodiments, the cytosolic and transmembrane domain comprise an amino acid sequence having at least 98% sequence identity with the amino acid sequence of SEQ ID NO: 52 (CD8β+Lck chimera). In some embodiments, the cytosolic and transmembrane domain comprise an amino acid sequence having at least 99% sequence identity with the amino acid sequence of SEQ ID NO: 52 (CD8β+Lck chimera). In some embodiments, the cytosolic and transmembrane domain comprise the amino acid sequence of SEQ ID NO: 52 (CD8β+Lck chimera).

In some embodiments, the TCR signaling domain polypeptide includes both a cytosolic domain and a transmembrane domain of a TCR co-receptor protein. In some embodiments, the cytosolic domain and transmembrane domain are from the same co-receptor or from different co-receptors.

Amino acid and nucleotide sequences of exemplary transmembrane and cytosolic domains are provided in Table 3.

TABLE 3

Table of Sequences

| SEQ ID NO | Description | Nucleotide/Amino Acid |
| --- | --- | --- |
| SEQ ID NO: 45 | CD4 Domain[1] | Nucleotide |
| SEQ ID NO: 46 | CD4 Domain[2] | Amino Acid |
| SEQ ID NO: 47 | CD8α Domain | Nucleotide |
| SEQ ID NO: 48 | CD8α Domain | Amino Acid |
| SEQ ID NO: 49 | CD8α + R(β) Domain | Nucleotide |
| SEQ ID NO: 50 | CD8α + R(β) Domain | Amino Acid |
| SEQ ID NO: 51 | CD8α + Lck Domain | Nucleotide |
| SEQ ID NO: 52 | CD8α + Lck Domain | Amino Acid |

[1]Extracellular linker, nucleotides 1-66; Transmembrane domain, nucleotides 67-132; Cytosolic domain, nucleotides 133-254
[2]Extracellular linker, amino acids 1-22; Transmembrane domain, amino acids 23-44; Cytosolic domain, amino acids 45-84

Configurations, Linkers, and Connectors

In some embodiments, a nucleic acid disclosed herein is in an order of (1) a first polynucleotide encoding an antigen-binding domain that binds BCMA; (2) a second polynucleotide encoding an antigen-binding domain that binds a TCR complex; (3) a third polynucleotide encoding a transmembrane domain and a cytosolic domain. In some embodiments, a nucleic acid disclosed herein is in an order of (1) a first polynucleotide encoding an antigen-binding domain that binds BCMA; (2) a second polynucleotide encoding an antigen-binding domain that binds a TCR complex; (3) a third polynucleotide encoding a transmembrane domain and a cytosolic domain, wherein the order is 5' end to 3' end. In some embodiments, a nucleic acid disclosed herein is in an order of (1) a first polynucleotide encoding an antigen-binding domain that binds BCMA; (2) a second polynucleotide encoding an antigen-binding domain that binds a TCR complex; (3) a third polynucleotide encoding a transmembrane domain and a cytosolic domain, wherein the order is 3' end to 5' end. In some embodiments, a nucleic acid described herein is in an order of (1) a first polynucleotide encoding an antigen-binding domain that binds a TCR complex; (2) a second polynucleotide encoding an antigen-binding domain that binds BCMA; (3) a third polynucleotide encoding a transmembrane domain and a cytosolic domain. In some embodiments, a nucleic acid described herein is in an order of (1) a first polynucleotide encoding an antigen-binding domain that binds a TCR complex; (2) a second polynucleotide encoding an antigen-binding domain that binds BCMA; (3) a third polynucleotide encoding a transmembrane domain and a cytosolic domain, wherein the order is 5' end to 3' end. In some embodiments, a nucleic acid described herein is in an order of (1) a first polynucleotide encoding an antigen-binding domain that binds a TCR complex; (2) a second polynucleotide encoding an antigen-binding domain that binds BCMA; (3) a third polynucleotide encoding a transmembrane domain and a cytosolic domain, wherein the order is 3' end to 5' end.

In some embodiments, a BCMA TAC polypeptide disclosed herein is in an order of (1) an antigen-binding domain that binds BCMA; (2) an antigen-binding domain that binds a TCR complex; (3) a transmembrane domain and a cytosolic domain, wherein the order is N-terminus to C-terminus. In some embodiments, a BCMA TAC polypeptide disclosed herein is in an order of (1) an antigen-binding domain that binds BCMA; (2) an antigen-binding domain that binds a TCR complex; (3) a transmembrane domain and a cytosolic domain, wherein the order is C-terminus to N-terminus. In some embodiments, a BCMA TAC polypeptide described herein is in an order of (1) an antigen-binding domain that binds a TCR complex; (2) an antigen-binding domain that binds BCMA; (3) a transmembrane domain and a cytosolic domain, wherein the order is N-terminus to C-terminus. In some embodiments, a BCMA TAC polypeptide described herein is in an order of (1) an antigen-binding domain that binds a TCR complex; (2) an antigen-binding domain that binds BCMA; (3) a transmembrane domain and a cytosolic domain, wherein the order is C-terminus to N-terminus.

In some embodiments, the antigen-binding domain that binds BCMA, the antigen-binding domain that binds the TCR complex, and/or the transmembrane domain and cytosolic domain are directly fused. For example, the antigen-binding domain that binds BCMA and the transmembrane domain and cytosolic domain are both fused to the antigen-binding domain that binds the TCR complex. In some embodiments, the antigen-binding domain that binds BCMA, the antigen-binding domain that binds the TCR complex, and/or the transmembrane domain and cytosolic domain are joined by at least one linker. In some embodiments, the antigen-binding domain that binds BCMA and the antigen-binding domain that binds the TCR complex are directly fused, and joined to the transmembrane domain and cytosolic domain by a linker. In some embodiments, the antigen-binding domain that binds the TCR complex and the transmembrane domain and cytosolic domain are directly fused, and joined to the antigen-binding domain that binds BCMA by a linker.

In some embodiments, the linker is a peptide linker. In some embodiments, the peptide linker comprises 1 to 40 amino acids. In some embodiments, the peptide linker comprises 1 to 30 amino acids. In some embodiments, the peptide linker comprises 1 to 15 amino acids. In some embodiments, the peptide linker comprises 1 to 10 amino acids. In some embodiments, the peptide linker comprises 1 to 6 amino acids. In some embodiments, the peptide linker comprises 30 to 40 amino acids. In some embodiments, the peptide linker comprises 32 to 36 amino acids. In some embodiments, the peptide linker comprises 5 to 30 amino acids. In some embodiments, the peptide linker comprises 5 amino acids. In some embodiments, the peptide linker comprises 10 amino acids. In some embodiments, the peptide linker comprises 15 amino acids. In some embodiments, the peptide linker comprises 20 amino acids. In some embodiments, the peptide linker comprises 25 amino acids. In some embodiments, the peptide linker comprises 30 amino acids. In some embodiments, the peptide linker comprises a glycine and/or serine-rich linker.

In some embodiments, the at least one linker comprises an amino acid sequence having at least 80% identity with the amino acid sequence of SEQ ID NO: 26 ((G4S)4-based linker), SEQ ID NO: 28 (G4S-based linker), SEQ ID NO: 6 (linker 1), SEQ ID NO: 8 (linker 2), SEQ ID NO: 10 (CD4 based linker), SEQ ID NO: 12 (short helix connector), SEQ ID NO: 14 (long helix connector), SEQ ID NO: 16 (large domain connector), or SEQ ID NO: 24 (G453 linker). In some embodiments, the at least one linker comprises an amino acid sequence having at least 85% identity with the amino acid sequence of SEQ ID NO: 26 ((G4S)4-based linker), SEQ ID NO: 28 (G4S-based linker), SEQ ID NO: 6 (linker 1), SEQ ID NO: 8 (linker 2), SEQ ID NO: 10 (CD4 based linker), SEQ ID NO: 12 (short helix connector), SEQ ID NO: 14 (long helix connector), SEQ ID NO: 16 (large domain connector), or SEQ ID NO: 24 (G453 linker). In some embodiments, the at least one linker comprises an amino acid sequence having at least 90% identity with the amino acid sequence of SEQ ID NO: 26 ((G4S)4-based linker), SEQ ID NO: 28 (G4S-based linker), SEQ ID NO: 6 (linker 1), SEQ ID NO: 8 (linker 2), SEQ ID NO: 10 (CD4 based linker), SEQ ID NO: 12 (short helix connector), SEQ ID NO: 14 (long helix connector), SEQ ID NO: 16 (large domain connector), or SEQ ID NO: 24 (G453 linker). In some embodiments, the at least one linker comprises an amino acid sequence having at least 95% identity with the amino acid sequence of SEQ ID NO: 26 ((G4S)$_4$-based linker), SEQ ID NO: 28 (G4S-based linker), SEQ ID NO: 6 (linker 1), SEQ ID NO: 8 (linker 2), SEQ ID NO: 10 (CD4 based linker), SEQ ID NO: 12 (short helix connector), SEQ ID NO: 14 (long helix connector), SEQ ID NO: 16 (large domain connector), or SEQ ID NO: 24 (G453 linker). In some embodiments, the at least one linker comprises an amino acid sequence having at least 96% identity with the amino acid sequence of SEQ ID NO: 26 ((G4S)$_4$-based linker), SEQ ID NO: 28 (G4S-based linker), SEQ ID NO: 6 (linker 1), SEQ ID NO: 8 (linker 2), SEQ ID NO: 10 (CD4 based linker), SEQ ID NO: 12 (short helix connector), SEQ ID NO: 14 (long helix connector), SEQ ID NO: 16 (large domain connector), or SEQ ID NO: 24 (G4S3 linker). In some embodiments, the at least one linker comprises an amino acid sequence having at least 97% identity with the amino acid sequence of SEQ ID NO: 26 ((G4S)$_4$-based linker), SEQ ID NO: 28 (G4S-based linker), SEQ ID NO: 6 (linker 1), SEQ ID NO: 8 (linker 2), SEQ ID NO: 10 (CD4 based linker), SEQ ID NO: 12 (short helix connector), SEQ ID NO: 14 (long helix connector), SEQ ID NO: 16 (large domain connector), or SEQ ID NO: 24 (G453 linker). In some embodiments, the at least one linker comprises an amino acid sequence having at least 98% identity with the amino acid sequence of SEQ ID NO: 26 ((G4S)$_4$-based linker), SEQ ID NO: 28 (G4S-based linker), SEQ ID NO: 6 (linker 1), SEQ ID NO: 8 (linker 2), SEQ ID NO: 10 (CD4 based linker), SEQ ID NO: 12 (short helix connector), SEQ ID NO: 14 (long helix connector), SEQ ID NO: 16 (large domain connector), or SEQ ID NO: 24 (G453 linker). In some embodiments, the at least one linker comprises an amino acid sequence having at least 99% identity with the amino acid sequence of SEQ ID NO: 26 ((G4S)$_4$-based linker), SEQ ID NO: 28 (G4S-based linker), SEQ ID NO: 6 (linker 1), SEQ ID NO: 8 (linker 2), SEQ ID NO: 10 (CD4 based linker), SEQ ID NO: 12 (short helix connector), SEQ ID NO: 14 (long helix connector), SEQ ID NO: 16 (large domain connector), or SEQ ID NO: 24 (G453 linker). In some embodiments, the at least one linker comprises the amino acid sequence of SEQ ID NO: 26 ((G4S)4-based linker), SEQ ID NO: 28 (G4S-based linker), SEQ ID NO: 6 (linker 1), SEQ ID NO: 8 (linker 2), SEQ ID NO: 10 (CD4 based linker), SEQ ID NO: 12 (short helix connector), SEQ ID NO: 14 (long helix connector), SEQ ID NO: 16 (large domain connector), or SEQ ID NO: 24 (G453 linker).

In some embodiments, the peptide linker that joins the antigen-binding domain that binds BCMA to the antigen-binding domain that binds a TCR complex (e.g., UCHT1) is known as the connector to distinguish this protein domain from other linkers in the TAC. The connector may be of any size. In some embodiments, the connector between the antigen-binding domain that binds a TCR complex and the antigen-binding domain that binds BCMA is a short helix comprising SEQ ID NO: 12. In some embodiments, the connector between the antigen-binding domain that binds a TCR complex and the antigen-binding domain that binds BCMA is a short helix encoded by SEQ ID NO: 11. In some embodiments, the connector between the antigen-binding domain that binds a TCR complex and the antigen-binding domain that binds BCMA is a long helix comprising SEQ ID NO: 14. In some embodiments, the connector between the antigen-binding domain that binds a TCR complex and the antigen-binding domain that binds BCMA is a long helix encoded by SEQ ID NO: 13. In some embodiments, the connector between the antigen-binding domain that binds a TCR complex and the antigen-binding domain that binds BCMA is a large domain comprising SEQ ID NO: 16. In some embodiments, the connector between the antigen-binding domain that binds a TCR complex and the antigen-binding domain that binds BCMA is a large domain encoded by SEQ ID NO: 15.

In some embodiments, a nucleic acid or TAC disclosed herein comprises a leader sequence. In some embodiments, the leader sequence is encoded by a nucleotide sequence having at least 80% sequence identity with the nucleotide sequence of SEQ ID NO: 1 (muIgG leader), SEQ ID NO: 17 (huIgG leader), SEQ ID NO: 19 (huCD8a leader), or SEQ ID NO: 29 (huCD8a leader). In some embodiments, the leader sequence is encoded by a nucleotide sequence having at least 85% sequence identity with the nucleotide sequence of SEQ ID NO: 1 (muIgG leader), SEQ ID NO: 17 (huIgG leader), SEQ ID NO: 19 (huCD8a leader), or SEQ ID NO: 29 (huCD8a leader). In some embodiments, the leader sequence is encoded by a nucleotide sequence having at least 90% sequence identity with the nucleotide sequence of SEQ ID NO: 1 (muIgG leader), SEQ ID NO: 17 (huIgG leader), SEQ ID NO: 19 (huCD8a leader), or SEQ ID NO: 29 (huCD8a leader). In some embodiments, the leader sequence is encoded by a nucleotide sequence having at least 95% sequence identity with the nucleotide sequence of SEQ ID NO: 1 (muIgG leader), SEQ ID NO: 17 (huIgG leader), SEQ ID NO: 19 (huCD8a leader), or SEQ ID NO: 29 (huCD8a leader). In some embodiments, the leader sequence is encoded by a nucleotide sequence having at least 96% sequence identity with the nucleotide sequence of SEQ ID NO: 1 (muIgG leader), SEQ ID NO: 17 (huIgG leader), SEQ ID NO: 19 (huCD8a leader), or SEQ ID NO: 29 (huCD8a leader). In some embodiments, the leader sequence is encoded by a nucleotide sequence having at least 97% sequence identity with the nucleotide sequence of SEQ ID NO: 1 (muIgG leader), SEQ ID NO: 17 (huIgG leader), SEQ ID NO: 19 (huCD8a leader), or SEQ ID NO: 29 (huCD8a leader). In some embodiments, the leader sequence is encoded by a nucleotide sequence having at least 98% sequence identity with the nucleotide sequence of SEQ ID NO: 1 (muIgG leader), SEQ ID NO: 17 (huIgG leader), SEQ ID NO: 19 (huCD8a leader), or SEQ ID NO: 29 (huCD8a leader). In some embodiments, the leader sequence is encoded by a nucleotide sequence having at least 99% sequence identity with the nucleotide sequence of SEQ ID NO: 1 (muIgG leader), SEQ ID NO: 17 (huIgG leader), SEQ ID NO: 19 (huCD8a leader), or SEQ ID NO: 29 (huCD8a leader). In some embodiments, the leader sequence comprises the nucleotide sequence of SEQ ID NO: 1 (muIgG leader), SEQ ID NO: 17 (huIgG leader), SEQ ID NO: 19 (huCD8a leader), or SEQ ID NO: 29 (huCD8a leader).

In some embodiments, a nucleic acid or TAC disclosed herein comprises a leader sequence. In some embodiments, the leader sequence comprises an amino acid sequence having at least 80% sequence identity with the amino acid sequence of SEQ ID NO: 2 (muIgG leader), SEQ ID NO: 18 (huIgG leader), or SEQ ID NO: 20 (huCD8a leader). In some embodiments, the leader sequence comprises an amino acid sequence having at least 85% sequence identity with the amino acid sequence of SEQ ID NO: 2 (muIgG leader), SEQ ID NO: 18 (huIgG leader), or SEQ ID NO: 20 (huCD8a leader). In some embodiments, the leader sequence comprises an amino acid sequence having at least 90% sequence identity with the amino acid sequence of SEQ ID NO: 2 (muIgG leader), SEQ ID NO: 18 (huIgG leader), or SEQ ID NO: 20 (huCD8a leader). In some embodiments, the leader sequence comprises an amino acid sequence having at least 95% sequence identity with the amino acid sequence of SEQ ID NO: 2 (muIgG leader), SEQ ID NO: 18 (huIgG leader), or SEQ ID NO: 20 (huCD8a leader). In some embodiments, the leader sequence comprises an amino acid sequence having at least 96% sequence identity with the amino acid sequence of SEQ ID NO: 2 (muIgG leader), SEQ ID NO: 18 (huIgG leader), or SEQ ID NO: 20 (huCD8a leader). In some embodiments, the leader sequence comprises an amino acid sequence having at least 97% sequence identity with the amino acid sequence of SEQ ID NO: 2 (muIgG leader), SEQ ID NO: 18 (huIgG leader), or SEQ ID NO: 20 (huCD8a leader). In some embodiments, the leader sequence comprises an amino acid sequence having at least 98% sequence identity with the amino acid sequence of SEQ ID NO: 2 (muIgG leader), SEQ ID NO: 18 (huIgG leader), or SEQ ID NO: 20 (huCD8a leader). In some embodiments, the leader sequence comprises an amino acid sequence having at least 99% sequence identity with the amino acid sequence of SEQ ID NO: 2 (muIgG leader), SEQ ID NO: 18 (huIgG leader), or SEQ ID NO: 20 (huCD8a leader). In some embodiments, the leader sequence comprises the amino acid sequence of SEQ ID NO: 2 (muIgG leader), SEQ ID NO: 18 (huIgG leader), or SEQ ID NO: 20 (huCD8a leader).

In some embodiments, a BCMA T cell antigen coupler polypeptide comprises a tag, e.g., a Myc tag. In some embodiments, the tag comprises an amino acid sequence having at least 80% identity with the amino acid sequence of SEQ ID NO: 4 (Myc Tag). In some embodiments, the tag comprises an amino acid sequence having at least 85% identity with the amino acid sequence of SEQ ID NO: 4 (Myc Tag). In some embodiments, the tag comprises an amino acid sequence having at least 90% identity with the amino acid sequence of SEQ ID NO: 4 (Myc Tag). In some embodiments, the tag comprises an amino acid sequence having at least 95% identity with the amino acid sequence of SEQ ID NO: 4 (Myc Tag). In some embodiments, the tag comprises an amino acid sequence having at least 96% identity with the amino acid sequence of SEQ ID NO: 4 (Myc Tag). In some embodiments, the tag comprises an amino acid sequence having at least 97% identity with the amino acid sequence of SEQ ID NO: 4 (Myc Tag). In some embodiments, the tag comprises an amino acid sequence having at least 98% identity with the amino acid sequence of SEQ ID NO: 4 (Myc Tag). In some embodiments, the tag comprises an amino acid sequence having at least 99% identity with the amino acid sequence of SEQ ID NO: 4 (Myc Tag). In some embodiments, the tag comprises the amino acid sequence of SEQ ID NO: 4 (Myc Tag).

Amino acid and nucleotide sequences of exemplary linkers, connectors, tags, and leader sequences are provided in Table 4.

TABLE 4

Table of Sequences

| SEQ ID NO | Description | Nucleotide/Amino Acid |
| --- | --- | --- |
| SEQ ID NO: 1 | muIgG leader (secretion signal) | Nucleotide |
| SEQ ID NO: 2 | muIgG leader (secretion signal) | Amino Acid |
| SEQ ID NO: 3 | Myc Tag | Nucleotide |
| SEQ ID NO: 4 | Myc Tag | Amino Acid |
| SEQ ID NO: 5 | Linker 1 | Nucleotide |
| SEQ ID NO: 6 | Linker 1 | AminoAcid |
| SEQ ID NO: 7 | Linker 2 | Nucleotide |
| SEQ ID NO: 8 | Linker 2 | Amino Acid |
| SEQ ID NO: 9 | CD4 linker | Nucleotide |
| SEQ ID NO: 10 | CD4 linker | Amino Acid |
| SEQ ID NO: 11 | Short Helix connector | Nucleotide |
| SEQ ID NO: 12 | Short Helix connector | Amino Acid |
| SEQ ID NO: 13 | Long Helix connector | Nucleotide |
| SEQ ID NO: 14 | Long Helix connector | Amino Acid |
| SEQ ID NO: 15 | Large domain connector | Nucleotide |
| SEQ ID NO: 16 | Large domain connector | Amino Acid |
| SEQ ID NO: 17 | huIgG | Nucleotide |
| SEQ ID NO: 18 | huIgG | Amino Acid |
| SEQ ID NO: 19 | huCD8a (1162) | Nucleotide |
| SEQ ID NO: 20 | huCD8a (1162) | Amino Acid |
| SEQ ID NO: 21 | Whitlow Linker | Nucleotide |
| SEQ ID NO: 22 | Whitlow Linker | Amino Acid |
| SEQ ID NO: 23 | (G4S)3 linker | Nucleotide |
| SEQ ID NO: 24 | (G4S)3 linker | Amino Acid |
| SEQ ID NO: 25 | (G4S)4 linker | Nucleotide |
| SEQ ID NO: 26 | (G4S)4 linker | Amino Acid |
| SEQ ID NO: 27 | G4S linker | Nucleotide |
| SEQ ID NO: 28 | G4S linker | Amino Acid |
| SEQ ID NO: 29 | huCD8a (1165) | Nucleotide |
| SEQ ID NO: 30 | huCD8a (1165) | Amino Acid |

Specific TACs

Disclosed herein, in certain embodiments, are BCMA TAC polypeptides comprising (a) an antigen-binding domain that binds BCMA, (b) a single-chain antibody (scFv) that binds CD3ε, and (c) a transmembrane and cytosolic domain of the CD4 co-receptor. In some embodiments, the BCMA TAC polypeptides comprise (a) an antigen-binding domain that binds BCMA, (b) UCHT1, and (c) a transmembrane and cytosolic domain of the CD4 co-receptor. In some embodiments, the BCMA TAC polypeptides comprise (a) an antigen-binding domain that binds BCMA, (b) UCHT1 (Y182T), and (c) a transmembrane and cytosolic domain of the CD4 co-receptor. In some embodiments, the BCMA TAC polypeptides comprise (a) an antigen-binding domain that binds BCMA, (b) huUCHT1, and (c) a transmembrane and cytosolic domain of the CD4 co-receptor. In some embodiments, the BCMA TAC polypeptides comprise (a) an antigen-binding domain that binds BCMA, (b) huUCHT1 (Y177T), and (c) a transmembrane and cytosolic domain of the CD4 co-receptor. In some embodiments, the BCMA TAC polypeptides comprise (a) an antigen-binding domain that binds BCMA, (b) OKT3, and (c) a transmembrane and cytosolic domain of the CD4 co-receptor. In some embodiments, the BCMA TAC polypeptides comprise (a) an antigen-binding domain that binds BCMA, (b) F6A, and (c) a transmembrane and cytosolic domain of the CD4 co-receptor. In some embodiments, the BCMA TAC polypeptides comprise (a) an antigen-binding domain that binds BCMA, (b) L2K, and (c) a transmembrane and cytosolic domain of the CD4 co-receptor.

Disclosed herein, in certain embodiments, are BCMA TAC polypeptides comprising (a) a DARPin that binds BCMA, (b) UCHT1, and (c) a transmembrane and cytosolic domain of the CD4 co-receptor. In some embodiments, the BCMA TAC polypeptides comprise (a) a DARPin that binds BCMA, (b) UCHT1 (Y182T), and (c) a transmembrane and cytosolic domain of the CD4 co-receptor. In some embodiments, the BCMA TAC polypeptides comprise (a) a DARPin that binds BCMA, (b) huUCHT1, and (c) a transmembrane and cytosolic domain of the CD4 co-receptor. In some embodiments, the BCMA TAC polypeptides comprise (a) a DARPin that binds BCMA, (b) huUCHT1 (Y177T), and (c) a transmembrane and cytosolic domain of the CD4 co-receptor. In some embodiments, the BCMA TAC polypeptides comprise (a) a DARPin that binds BCMA, (b) OKT3, and (c) a transmembrane and cytosolic domain of the CD4 co-receptor. In some embodiments, the BCMA TAC polypeptides comprise (a) a DARPin that binds BCMA, (b) F6A, and (c) a transmembrane and cytosolic domain of the CD4 co-receptor. In some embodiments, the BCMA TAC polypeptides comprise (a) a DARPin that binds BCMA, (b) L2K, and (c) a transmembrane and cytosolic domain of the CD4 co-receptor.

Disclosed herein, in certain embodiments, are BCMA TACs comprising (a) a scFv that binds BCMA, (b) UCHT1, and (c) a transmembrane and cytosolic domain of the CD4 co-receptor. In some embodiments, the BCMA TAC polypeptides comprise (a) a scFv that binds BCMA, (b) UCHT1 (Y182T), and (c) a transmembrane and cytosolic domain of the CD4 co-receptor. In some embodiments, the BCMA TAC polypeptides comprise (a) a scFv that binds BCMA, (b) huUCHT1, and (c) a transmembrane and cytosolic domain of the CD4 co-receptor. In some embodiments, the BCMA TAC polypeptides comprise (a) a scFv that binds BCMA, (b) huUCHT1 (Y177T), and (c) a transmembrane and cytosolic domain of the CD4 co-receptor. In some embodiments, the BCMA TAC polypeptides comprise (a) a scFv that binds BCMA, (b) OKT3, and (c) a transmembrane and cytosolic domain of the CD4 co-receptor. In some embodiments, the BCMA TAC polypeptides comprise (a) a scFv that binds BCMA, (b) F6A, and (c) a transmembrane and cytosolic domain of the CD4 co-receptor. In some embodiments, the BCMA TAC polypeptides comprise (a) a scFv that binds BCMA, (b) L2K, and (c) a transmembrane and cytosolic domain of the CD4 co-receptor.

Disclosed herein, in certain embodiments, are BCMA TACs comprising (a) a nanobody that binds BCMA, (b) UCHT1, and (c) a transmembrane and cytosolic domain of the CD4 co-receptor. In some embodiments, the BCMA TAC polypeptides comprise (a) a nanobody that binds BCMA, (b) UCHT1 (Y182T), and (c) a transmembrane and cytosolic domain of the CD4 co-receptor. In some embodiments, the BCMA TAC polypeptides comprise (a) a nanobody that binds BCMA, (b) huUCHT1, and (c) a transmembrane and cytosolic domain of the CD4 co-receptor. In some embodiments, the BCMA TAC polypeptides comprise (a) a nanobody that binds BCMA, (b) huUCHT1 (Y177T), and (c) a transmembrane and cytosolic domain of the CD4 co-receptor. In some embodiments, the BCMA TAC polypeptides comprise (a) a nanobody that binds BCMA, (b) OKT3, and (c) a transmembrane and cytosolic domain of the CD4 co-receptor. In some embodiments, the BCMA TAC polypeptides comprise (a) a nanobody that binds BCMA, (b) F6A, and (c) a transmembrane and cytosolic domain of the CD4 co-receptor. In some embodiments, the BCMA TAC polypeptides comprise (a) a nanobody that binds BCMA, (b) L2K, and (c) a transmembrane and cytosolic domain of the CD4 co-receptor.

Disclosed herein, in certain embodiments, are BCMA TACs comprising (a) an antigen-binding domain that binds BCMA, (b) a single-chain antibody (scFv) that binds CD3ε, and (c) a transmembrane and cytosolic domain of the CD8 co-receptor. In some embodiments, the BCMA TAC polypeptides comprise (a) an antigen-binding domain that binds BCMA, (b) UCHT1, and (c) a transmembrane and cytosolic domain of the CD8 co-receptor. In some embodiments, the BCMA TAC polypeptides comprise (a) an antigen-binding domain that binds BCMA, (b) UCHT1 (Y182T), and (c) a transmembrane and cytosolic domain of the CD8 co-receptor. In some embodiments, the BCMA TAC polypeptides comprise (a) an antigen-binding domain that binds BCMA, (b) huUCHT1, and (c) a transmembrane and cytosolic domain of the CD8 co-receptor. In some embodiments, the BCMA TAC polypeptides comprise (a) an antigen-binding domain that binds BCMA, (b) huUCHT1 (Y177T), and (c) a transmembrane and cytosolic domain of the CD8 co-receptor. In some embodiments, the BCMA TAC polypeptides comprise (a) an antigen-binding domain that binds BCMA, (b) OKT3, and (c) a transmembrane and cytosolic domain of the CD8 co-receptor. In some embodiments, the BCMA TAC polypeptides comprise (a) an antigen-binding domain that binds BCMA, (b) F6A, and (c) a transmembrane and cytosolic domain of the CD8 co-receptor. In some embodiments, the BCMA TAC polypeptides comprise (a) an antigen-binding domain that binds BCMA, (b) L2K, and (c) a transmembrane and cytosolic domain of the CD8 co-receptor.

Disclosed herein, in certain embodiments, are BCMA TACs comprising (a) a DARPin that binds BCMA, (b) UCHT1, and (c) a transmembrane and cytosolic domain of the CD4 co-receptor. In some embodiments, the BCMA TAC polypeptides comprise (a) a DARPin that binds BCMA, (b) UCHT1 (Y182T), and (c) a transmembrane and cytosolic domain of the CD8 co-receptor. In some embodiments, the BCMA TAC polypeptides comprise (a) a DARPin that binds BCMA, (b) huUCHT1, and (c) a transmembrane and cytosolic domain of the CD8 co-receptor. In some embodiments, the BCMA TAC polypeptides comprise (a) a DARPin that binds BCMA, (b) huUCHT1 (Y177T), and (c) a transmembrane and cytosolic domain of the CD8 co-receptor. In some embodiments, the BCMA TAC polypeptides comprise (a) a DARPin that binds BCMA, (b) OKT3, and (c) a transmembrane and cytosolic domain of the CD8 co-receptor. In some embodiments, the BCMA TAC polypeptides comprise (a) a DARPin that binds BCMA, (b) F6A, and (c) a transmembrane and cytosolic domain of the CD8 co-receptor. In some embodiments, the BCMA TAC polypeptides comprise (a) a DARPin that binds BCMA, (b) L2K, and (c) a transmembrane and cytosolic domain of the CD8 co-receptor.

Disclosed herein, in certain embodiments, are BCMA TACs comprising (a) a scFv that binds BCMA, (b) UCHT1, and (c) a transmembrane and cytosolic domain of the CD8 co-receptor. In some embodiments, the BCMA TAC polypeptides comprise (a) a scFv that binds BCMA, (b) UCHT1 (Y182T), and (c) a transmembrane and cytosolic domain of the CD8 co-receptor. In some embodiments, the BCMA TAC polypeptides comprise (a) a scFv that binds BCMA, (b) huUCHT1, and (c) a transmembrane and cytosolic domain of the CD8 co-receptor. In some embodiments, the BCMA TAC polypeptides comprise (a) a scFv that binds BCMA, (b)

huUCHT1 (Y177T), and (c) a transmembrane and cytosolic domain of the CD8 co-receptor. In some embodiments, the BCMA TAC polypeptides comprise (a) a scFv that binds BCMA, (b) OKT3, and (c) a transmembrane and cytosolic domain of the CD8 co-receptor. In some embodiments, the TAC polypeptides comprise (a) a scFv that binds BCMA, (b) F6A, and (c) a transmembrane and cytosolic domain of the CD8 co-receptor. In some embodiments, the BCMA TAC polypeptides comprise (a) a scFv that binds BCMA, (b) L2K, and (c) a transmembrane and cytosolic domain of the CD8 co-receptor.

Disclosed herein, in certain embodiments, are BCMA TACs comprising (a) a nanobody that binds BCMA, (b) UCHT1, and (c) a transmembrane and cytosolic domain of the CD8 co-receptor. In some embodiments, the BCMA TAC polypeptides comprise (a) a nanobody that binds BCMA, (b) UCHT1 (Y182T), and (c) a transmembrane and cytosolic domain of the CD8 co-receptor. In some embodiments, the BCMA TAC polypeptides comprise (a) a nanobody that binds BCMA, (b) huUCHT1, and (c) a transmembrane and cytosolic domain of the CD8 co-receptor. In some embodiments, the BCMA TAC polypeptides comprise (a) a nanobody that binds BCMA, (b) huUCHT1 (Y177T), and (c) a transmembrane and cytosolic domain of the CD8 co-receptor. In some embodiments, the BCMA TAC polypeptides comprise (a) a nanobody that binds BCMA, (b) OKT3, and (c) a transmembrane and cytosolic domain of the CD8 co-receptor. In some embodiments, the TAC polypeptides comprise (a) a nanobody that binds BCMA, (b) F6A, and (c) a transmembrane and cytosolic domain of the CD8 co-receptor. In some embodiments, the BCMA TAC polypeptides comprise (a) a nanobody that binds BCMA, (b) L2K, and (c) a transmembrane and cytosolic domain of the CD8 co-receptor.

Disclosed herein, in certain embodiments, are BCMA TAC polypeptides comprising (a) an antigen-binding domain that binds BCMA comprising the amino acid sequence of SEQ ID NO: 63 (3625 scFv VL-VH), (b) an antigen binding domain that binds CD3ε comprising the amino acid sequence of SEQ ID NO: 42 (huUCHT1 (Y177T)), and (c) a transmembrane and cytosolic domain comprising the amino acid sequence of SEQ ID NO: 46 (CD4 transmembrane and cytosolic domain).

Disclosed herein, in certain embodiments, are BCMA TAC polypeptides comprising (a) a leader sequence comprising the amino acid sequence of SEQ ID NO: 20 (huCD8a leader), (b) an antigen-binding domain that binds BCMA comprising the amino acid sequence of SEQ ID NO: 63 (3625 scFv VL-VH), (c) a tag comprising the amino acid sequence of SEQ ID NO: 4 (Myc Tag), (d) a linker comprising the amino acid sequence of SEQ ID NO: 26 ((G4S)$_4$-based linker), (e) an antigen binding domain that binds CD3ε comprising the amino acid sequence of SEQ ID NO: 42 (huUCHT1 (Y177T)), (f) a linker comprising the amino acid sequence of SEQ ID NO: 28 (G4S-based linker), and (g) a transmembrane and cytosolic domain comprising the amino acid sequence of SEQ ID NO: 46 (CD4 transmembrane and cytosolic domain).

Disclosed herein, in certain embodiments, are BCMA TAC polypeptides comprising (a) an antigen-binding domain that binds BCMA comprising the amino acid sequence of SEQ ID NO: 65 (3625 scFv VH-VL), (b) an antigen binding domain that binds CD3ε comprising the amino acid sequence of SEQ ID NO: 42 (huUCHT1 (Y177T)), and (c) a transmembrane and cytosolic domain comprising the amino acid sequence of SEQ ID NO: 46 (CD4 transmembrane and cytosolic domain).

Disclosed herein, in certain embodiments, are BCMA TAC polypeptides comprising (a) a leader sequence comprising the amino acid sequence of SEQ ID NO: 20 (huCD8a leader), (b) an antigen-binding domain that binds BCMA comprising the amino acid sequence of SEQ ID NO: 65 (3625 scFv VH-VL), (c) a tag comprising the amino acid sequence of SEQ ID NO: 4 (Myc Tag), (d) a linker comprising the amino acid sequence of SEQ ID NO: 26 ((G4S)$_4$-based linker), (e) an antigen binding domain that binds CD3ε comprising the amino acid sequence of SEQ ID NO: 42 (huUCHT1 (Y177T)), (f) a linker comprising the amino acid sequence of SEQ ID NO: 28 (G4S-based linker), and (g) a transmembrane and cytosolic domain comprising the amino acid sequence of SEQ ID NO: 46 (CD4 transmembrane and cytosolic domain).

In some embodiments, a disclosed TAC polypeptide comprises an amino acid sequence having at least 80% sequence identity with the amino acid sequence of SEQ ID NO: 67 (1165 TAC w/o leader sequence). In some embodiments, a disclosed TAC polypeptide comprises an amino acid sequence having at least 85% sequence identity with the amino acid sequence of SEQ ID NO: 67 (1165 TAC w/o leader sequence). In some embodiments, a disclosed TAC polypeptide comprises an amino acid sequence having at least 90% sequence identity with the amino acid sequence of SEQ ID NO: 67 (1165 TAC w/o leader sequence). In some embodiments, a disclosed TAC polypeptide comprises an amino acid sequence having at least 95% sequence identity with the amino acid sequence of SEQ ID NO: 67 (1165 TAC w/o leader sequence). In some embodiments, a disclosed TAC polypeptide comprises an amino acid sequence having at least 96% sequence identity with the amino acid sequence of SEQ ID NO: 67 (1165 TAC w/o leader sequence). In some embodiments, a disclosed TAC polypeptide comprises an amino acid sequence having at least 97% sequence identity with the amino acid sequence of SEQ ID NO: 67 (1165 TAC w/o leader sequence). In some embodiments, a disclosed TAC polypeptide comprises an amino acid sequence having at least 98% sequence identity with the amino acid sequence of SEQ ID NO: 67 (1165 TAC w/o leader sequence). In some embodiments, a disclosed TAC polypeptide comprises an amino acid sequence having at least 99% sequence identity with the amino acid sequence of SEQ ID NO: 67 (1165 TAC w/o leader sequence). In some embodiments, a disclosed TAC polypeptide comprises the amino acid sequence of SEQ ID NO: 67 (1165 TAC w/o leader sequence).

In some embodiments, a disclosed TAC polypeptide comprises an amino acid sequence having at least 80% sequence identity with the amino acid sequence of SEQ ID NO: 69 (1165 TAC w/ leader sequence). In some embodiments, a disclosed TAC polypeptide comprises an amino acid sequence having at least 85% sequence identity with the amino acid sequence of SEQ ID NO: 69 (1165 TAC w/ leader sequence). In some embodiments, a disclosed TAC polypeptide comprises an amino acid sequence having at least 90% sequence identity with the amino acid sequence of SEQ ID NO: 69 (1165 TAC w/ leader sequence). In some embodiments, a disclosed TAC polypeptide comprises an amino acid sequence having at least 95% sequence identity with the amino acid sequence of SEQ ID NO: 69 (1165 TAC w/ leader sequence). In some embodiments, a disclosed TAC polypeptide comprises an amino acid sequence having at least 96% sequence identity with the amino acid sequence of SEQ ID NO: 69 (1165 TAC w/ leader sequence). In some embodiments, a disclosed TAC polypeptide comprises an amino acid sequence having at least 97% sequence identity with the amino acid sequence of SEQ ID NO: 69 (1165 TAC w/ leader sequence). In some embodiments, a disclosed TAC polypeptide comprises an amino acid sequence having at least 98% sequence identity with the amino acid sequence of SEQ ID NO: 69 (1165 TAC w/ leader sequence). In some embodiments, a disclosed TAC polypeptide comprises an amino acid sequence having at least 99% sequence identity with the amino acid sequence of SEQ ID NO: 69 (1165 TAC w/ leader sequence). In some embodiments, a disclosed TAC polypeptide comprises the amino acid sequence of SEQ ID NO: 69 (1165 TAC w/ leader sequence).

In some embodiments, a disclosed TAC polypeptide comprises an amino acid sequence having at least 80% sequence identity with the amino acid sequence of SEQ ID NO: 71 (1162 TAC w/o leader sequence). In some embodiments, a disclosed TAC polypeptide comprises an amino acid sequence having at least 85% sequence identity with the amino acid sequence of SEQ ID NO: 71 (1162 TAC w/o leader sequence). In some embodiments, a disclosed TAC polypeptide comprises an amino acid sequence having at least 90% sequence identity with the amino acid sequence of SEQ ID NO: 71 (1162 TAC w/o leader sequence). In some embodiments, a disclosed TAC polypeptide comprises an amino acid sequence having at least 95% sequence identity with the amino acid sequence of SEQ ID NO: 71 (1162 TAC w/o leader sequence). In some embodiments, a disclosed TAC polypeptide comprises an amino acid sequence having at least 96% sequence identity with the amino acid sequence of SEQ ID NO: 71 (1162 TAC w/o leader sequence). In some embodiments, a disclosed TAC polypeptide comprises an amino acid sequence having at least 97% sequence identity with the amino acid sequence of SEQ ID NO: 71 (1162 TAC w/o leader sequence). In some embodiments, a disclosed TAC polypeptide comprises an amino acid sequence having at least 98% sequence identity with the amino acid sequence of SEQ ID NO: 71 (1162 TAC w/o leader sequence). In some embodiments, a disclosed TAC polypeptide comprises an amino acid sequence having at least 99% sequence identity with the amino acid sequence of SEQ ID NO: 71 (1162 TAC w/o leader sequence). In some embodiments, a disclosed TAC polypeptide comprises the amino acid sequence of SEQ ID NO: 71 (1162 TAC w/o leader sequence).

In some embodiments, a disclosed TAC polypeptide comprises an amino acid sequence having at least 80% sequence identity with the amino acid sequence of SEQ ID NO: 73 (1162 TAC w/ leader sequence). In some embodiments, a disclosed TAC polypeptide comprises an amino acid sequence having at least 85% sequence identity with the amino acid sequence of SEQ ID NO: 73 (1162 TAC w/ leader sequence). In some embodiments, a disclosed TAC polypeptide comprises an amino acid sequence having at least 90% sequence identity with the amino acid sequence of SEQ ID NO: 73 (1162 TAC w/ leader sequence). In some embodiments, a disclosed TAC polypeptide comprises an amino acid sequence having at least 95% sequence identity with the amino acid sequence of SEQ ID NO: 73 (1162 TAC w/ leader sequence). In some embodiments, a disclosed TAC polypeptide comprises an amino acid sequence having at least 96% sequence identity with the amino acid sequence of SEQ ID NO: 73 (1162 TAC w/ leader sequence). In some embodiments, a disclosed TAC polypeptide comprises an amino acid sequence having at least 97% sequence identity with the amino acid sequence of SEQ ID NO: 73 (1162 TAC w/ leader sequence). In some embodiments, a disclosed TAC polypeptide comprises an amino acid sequence having at least 98% sequence identity with the amino acid sequence of SEQ ID NO: 73 (1162 TAC w/ leader sequence). In some embodiments, a disclosed TAC polypeptide comprises an amino acid sequence having at least 99% sequence identity with the amino acid sequence of SEQ ID NO: 73 (1162 TAC w/ leader sequence). In some embodiments, a disclosed TAC polypeptide comprises the amino acid sequence of SEQ ID NO: 73 (1162 TAC w/ leader sequence).

In some embodiments, a disclosed nucleic acid comprises a nucleotide sequence having at least 80% sequence identity with the nucleotide sequence of SEQ ID NO: 68 (1165 TAC w/o leader sequence). In some embodiments, a disclosed nucleic acid comprises a nucleotide sequence having at least 85% sequence identity with the nucleotide sequence of SEQ ID NO: 68 (1165 TAC w/o leader sequence). In some embodiments, a disclosed nucleic acid comprises a nucleotide sequence having at least 90% sequence identity with the nucleotide sequence of SEQ ID NO: 68 (1165 TAC w/o leader sequence). In some embodiments, a disclosed nucleic acid comprises a nucleotide sequence having at least 95% sequence identity with the nucleotide sequence of SEQ ID NO: 68 (1165 TAC w/o leader sequence). In some embodiments, a disclosed nucleic acid comprises a nucleotide sequence having at least 96% sequence identity with the nucleotide sequence of SEQ ID NO: 68 (1165 TAC w/o leader sequence). In some embodiments, a disclosed nucleic acid comprises a nucleotide sequence having at least 97% sequence identity with the nucleotide sequence of SEQ ID NO: 68 (1165 TAC w/o leader sequence). In some embodiments, a disclosed nucleic acid comprises a nucleotide sequence having at least 98% sequence identity with the nucleotide sequence of SEQ ID NO: 68 (1165 TAC w/o leader sequence). In some embodiments, a disclosed nucleic acid comprises a nucleotide sequence having at least 99% sequence identity with the nucleotide sequence of SEQ ID NO: 68 (1165 TAC w/o leader sequence). In some embodiments, a disclosed nucleic acid comprises a nucleotide sequence having at least 100% sequence identity with the nucleotide sequence of SEQ ID NO: 68 (1165 TAC w/o leader sequence).

In some embodiments, a disclosed nucleic acid comprises a nucleotide sequence having at least 80% sequence identity with the nucleotide sequence of SEQ ID NO: 70 (1165 TAC w/ leader sequence). In some embodiments, a disclosed nucleic acid comprises a nucleotide sequence having at least 85% sequence identity with the nucleotide sequence of SEQ ID NO: 70 (1165 TAC w/ leader sequence). In some embodiments, a disclosed nucleic acid comprises a nucleotide sequence having at least 90% sequence identity with the nucleotide sequence of SEQ ID NO: 70 (1165 TAC w/ leader sequence). In some embodiments, a disclosed nucleic acid comprises a nucleotide sequence having at least 95% sequence identity with the nucleotide sequence of SEQ ID NO: 70 (1165 TAC w/ leader sequence). In some embodiments, a disclosed nucleic acid comprises a nucleotide sequence having at least 96% sequence identity with the nucleotide sequence of SEQ ID NO: 70 (1165 TAC w/ leader sequence). In some embodiments, a disclosed nucleic acid comprises a nucleotide sequence having at least 97% sequence identity with the nucleotide sequence of SEQ ID NO: 70 (1165 TAC w/ leader sequence). In some embodiments, a disclosed nucleic acid comprises a nucleotide sequence having at least 98% sequence identity with the nucleotide sequence of SEQ ID NO: 70 (1165 TAC w/ leader sequence). In some embodiments, a disclosed nucleic acid comprises a nucleotide sequence having at least 99% sequence identity with the nucleotide sequence of SEQ ID NO: 70 (1165 TAC w/ leader sequence). In some embodiments, a disclosed nucleic acid comprises a nucleotide sequence having at least 100% sequence identity with the nucleotide sequence of SEQ ID NO: 70 (1165 TAC w/ leader sequence).

In some embodiments, a disclosed nucleic acid comprises a nucleotide sequence having at least 80% sequence identity with the nucleotide sequence of SEQ ID NO: 72 (1162 TAC w/o leader sequence). In some embodiments, a disclosed nucleic acid comprises a nucleotide sequence having at least 85% sequence identity with the nucleotide sequence of SEQ ID NO: 72 (1162 TAC w/o leader sequence). In some embodiments, a disclosed nucleic acid comprises a nucleotide sequence having at least 90% sequence identity with the nucleotide sequence of SEQ ID NO: 72 (1162 TAC w/o leader sequence). In some embodiments, a disclosed nucleic acid comprises a nucleotide sequence having at least 95% sequence identity with the nucleotide sequence of SEQ ID NO: 72 (1162 TAC w/o leader sequence). In some embodiments, a disclosed nucleic acid comprises a nucleotide sequence having at least 96% sequence identity with the nucleotide sequence of SEQ ID NO: 72 (1162 TAC w/o leader sequence). In some embodiments, a disclosed nucleic acid comprises a nucleotide sequence having at least 97% sequence identity with the nucleotide sequence of SEQ ID NO: 72 (1162 TAC w/o leader sequence). In some embodiments, a disclosed nucleic acid comprises a nucleotide sequence having at least 98% sequence identity with the nucleotide sequence of SEQ ID NO: 72 (1162 TAC w/o leader sequence). In some embodiments, a disclosed nucleic acid comprises a nucleotide sequence having at least 99% sequence identity with the nucleotide sequence of SEQ ID NO: 72 (1162 TAC w/o leader sequence). In some embodiments, a disclosed nucleic acid comprises a nucleotide sequence having at least 100% sequence identity with the nucleotide sequence of SEQ ID NO: 72 (1162 TAC w/o leader sequence).

In some embodiments, a disclosed nucleic acid comprises a nucleotide sequence having at least 80% sequence identity with the nucleotide sequence of SEQ ID NO: 74 (1162 TAC w/ leader sequence). In some embodiments, a disclosed nucleic acid comprises a nucleotide sequence having at least 85% sequence identity with the nucleotide sequence of SEQ ID NO: 74 (1162 TAC w/ leader sequence). In some embodiments, a disclosed nucleic acid comprises a nucleotide sequence having at least 90% sequence identity with the nucleotide sequence of SEQ ID NO: 74 (1162 TAC w/ leader sequence). In some embodiments, a disclosed nucleic acid comprises a nucleotide sequence having at least 95% sequence identity with the nucleotide sequence of SEQ ID NO: 74 (1162 TAC w/ leader sequence). In some embodiments, a disclosed nucleic acid comprises a nucleotide sequence having at least 96% sequence identity with the nucleotide sequence of SEQ ID NO: 74 (1162 TAC w/ leader sequence). In some embodiments, a disclosed nucleic acid comprises a nucleotide sequence having at least 97% sequence identity with the nucleotide sequence of SEQ ID NO: 74 (1162 TAC w/ leader sequence). In some embodiments, a disclosed nucleic acid comprises a nucleotide sequence having at least 98% sequence identity with the nucleotide sequence of SEQ ID NO: 74 (1162 TAC w/ leader sequence). In some embodiments, a disclosed nucleic acid comprises a nucleotide sequence having at least 99% sequence identity with the nucleotide sequence of SEQ ID NO: 74 (1162 TAC w/ leader sequence). In some embodiments, a disclosed nucleic acid comprises a nucleotide sequence having at least 100% sequence identity with the nucleotide sequence of SEQ ID NO: 74 (1162 TAC w/ leader sequence).

In certain instances, the BCMA TAC polypeptides draw CD3 and TCR into lipid raft regions of the membrane, and brings Lck into the proximity of the TCR, similar to natural MHC binding.

In some embodiments, the BCMA TAC comprises 3625 ($V_H$-$V_L$) scFv-($G_4S$)$_4$ linker-huUCHT1$^{Y177T}$. In some embodiments, the BCMA TAC comprises 3625($V_L$-$V_H$) scFv-($G_4S$)$_4$ linker-huUCHT1$^{Y177T}$.

Amino acid and nucleotide sequences of specific BCMA TACs are provided in Table 5.

TABLE 5

Table of Sequences

| SEQ ID NO | Description | Nucleotide/ Amino Acid |
|---|---|---|
| SEQ ID NO: 67 | 1165 TAC (w/o leader sequence) | Amino Acid |
| SEQ ID NO: 68 | 1165 TAC (w/o leader sequence) | Nucleotide |
| SEQ ID NO: 69 | 1165 TAC (w/ leader sequence) | Amino Acid |
| SEQ ID NO: 70 | 1165 TAC (w/ leader sequence) | Nucleotide |
| SEQ ID NO: 71 | 1162 TAC (w/o leader sequence) | Amino Acid |
| SEQ ID NO: 72 | 1162 TAC (w/o leader sequence) | Nucleotide |
| SEQ ID NO: 73 | 1162 TAC (w/ leader sequence) | Amino Acid |
| SEQ ID NO: 74 | 1162 TAC (w/ leader sequence) | Nucleotide |
| SEQ ID NO: 75 | 1002 TAC (w/ leader sequence) | Amino Acid |
| SEQ ID NO: 76 | 1042 TAC (w/ leader sequence) | Amino Acid |

Vector Constructs

Disclosed herein, in certain embodiments, are vectors comprising a BCMA TAC nucleic acid sequence as disclosed herein. In some embodiments, the vectors further comprise a promoter. In some embodiments, the promoter is functional in a mammalian cell. Promoters, regions of DNA that initiate transcription of a particular nucleic acid sequence, are well known in the art. A "promoter functional in a mammalian cell" refers to a promoter that drives expression of the associated nucleic acid sequence in a mammalian cell. A promoter that drives expression of a nucleic acid sequence is referred to as being "operably connected" to the nucleic acid sequence.

A variety of delivery vectors and expression vehicles are employed to introduce nucleic acids described herein into a cell.

Disclosed herein, in certain embodiments, are vectors comprising:
  a. a first polynucleotide encoding an antigen-binding domain that binds BCMA;
  b. a second polynucleotide encoding an antigen-binding domain that binds a protein associated with a TCR complex;
  c. a third polynucleotide encoding a T cell receptor signaling domain polypeptide; and
  d. a promoter that is functional in a mammalian cell.

In some embodiments, the first polynucleotide and third polynucleotide are fused to the second polynucleotide and the coding sequence is operably connected to the promoter. In some embodiments, the second polynucleotide and third polynucleotide are fused to the first polynucleotide and the coding sequence is operably connected to the promoter. In some embodiments, the vector is designed for expression in mammalian cells. In some embodiments, the vector is a viral vector. In some embodiments, the viral vector is a retroviral vector.

In some embodiments, vectors that are useful comprise vectors derived from retroviruses, lentiviruses, Murine Stem Cell Viruses (MSCV), pox viruses, adenoviruses, and adeno-associated viruses. Other delivery vectors that are useful comprise vectors derived from herpes simplex viruses, transposons, vaccinia viruses, human papilloma virus, Simian immunodeficiency viruses, HTLV, human foamy virus and variants thereof. Further vectors that are useful comprise vectors derived from spumaviruses, mammalian type B retroviruses, mammalian type C retroviruses, avian type C retroviruses, mammalian type D retroviruses and HTLV/BLV type retroviruses. One example of a lentiviral vector useful in the disclosed compositions and methods is the pCCL4 vector.

Pharmaceutical Compositions

Disclosed herein, in certain embodiments, are pharmaceutical compositions comprising an engineered T cell disclosed herein (transduced with and/or expressing a BCMA TAC polypeptide), and a pharmaceutically acceptable carrier. Pharmaceutically acceptable carriers include, but are not limited to, buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); or preservatives. In some embodiments, the engineered T cells are formulated for intravenous administration.

Pharmaceutical compositions are administered in a manner appropriate to the disease to be treated (or prevented). The quantity and frequency of administration is determined by such factors as the condition of the patient, and the type and severity of the patient's disease, although appropriate dosages are determined by clinical trials. When "an immunologically effective amount," "an anti-tumor effective amount," "a tumor-inhibiting effective amount," or "therapeutic amount" is indicated, the precise amount of the compositions of the present invention to be administered is determined by a physician with consideration of individual differences in age, weight, tumor size, extent of infection or metastasis, and condition of the patient (subject).

In some embodiments, the engineered T cells and/or pharmaceutical compositions described herein are administered at a dosage of $10^1$ to $10^{15}$ cells per kg body weight, $10^4$ to $10^9$ cells per kg body weight, optionally $10^5$ to $10^8$ cells per kg body weight, $10^6$ to $10^7$ cells per kg body weight or $10^5$ to $10^6$ cells per kg body weight, including all integer values within those ranges. In some embodiments, the modified T cells and/or pharmaceutical compositions described herein are administered at a dosage of greater than $10^1$ cells per kg body weight. In some embodiments, the modified T cells and/or pharmaceutical compositions described herein are administered at a dosage of less than $10^{15}$ cells per kg body weight.

In some embodiments, the engineered T cells and/or pharmaceutical compositions described herein are administered at a dosage of $0.5\times10^6$ cells, $2\times10^6$ cells, $4\times10^6$ cells, $5\times10^6$ cells, $1.2\times10^7$ cells, $2\times10^7$ cells, $5\times10^7$ cells, $2\times10^8$ cells, $5\times10^8$ cells, $2\times10^9$ cells, $0.5\text{-}2000\times10^6$ cells, $0.5\text{-}2\times10^6$ cells, $0.5\text{-}2\times10^7$ cells, $0.5\text{-}2\times10^8$ cells, or $0.5\text{-}2\times10^9$ cells, including all integer values within those ranges.

Also disclosed herein are pharmaceutical compositions comprising engineered/modified and unmodified T cells, or comprising different populations of engineered/modified T cells with or without unmodified T cells. One of ordinary skill in the art would understand that a therapeutic quantity of engineered/modified T cells need not be homogenous in nature.

In some embodiments, T cell compositions are administered multiple times at these dosages. In some embodiments, the dosage is administered a single time or multiple times, for example daily, weekly, biweekly, or monthly, hourly, or is administered upon recurrence, relapse or progression of the cancer being treated. The cells, in some embodiments, are administered by using infusion techniques that are commonly known in immunotherapy (see, e.g., Rosenberg et al., New Eng. J. of Med. 319:1676, 1988).

In some embodiments, the pharmaceutical composition is substantially free of, e.g., there are no detectable levels of a contaminant, e.g., selected from the group consisting of endotoxin, *Mycoplasma*, replication competent lentivirus (RCL), p24, VSV-G nucleic acid, HIV gag, residual anti-CD3/anti-CD28 coated beads, mouse antibodies, pooled human serum, bovine serum albumin, bovine serum, culture media components, vector packaging cell or plasmid components, a bacterium a fungus, *Mycoplasma*, IL-2, and IL-7.

In some embodiments, the modified/engineered T cells and/or pharmaceutical compositions are administered by methods including, but not limited to, aerosol inhalation, injection, infusion, ingestion, transfusion, implantation or transplantation. The modified T cells and/or pharmaceutical compositions may be administered to a subject transarterially, subcutaneously, intradermally, intratumorally, intranodally, intramedullary, intramuscularly, by intravenous (i.v.) injection, by intravenous (i.v.) infusion, or intraperitoneally. The modified/engineered T cells and/or pharmaceutical compositions thereof may be administered to a patient by intradermal or subcutaneous injection. The modified/engineered T cells and/or pharmaceutical compositions thereof may be administered by i.v. injection. The modified/engineered T cells and/or pharmaceutical compositions thereof may be injected directly into a tumor, lymph node, or site of infection.

A pharmaceutical composition may be prepared by known methods for the preparation of pharmaceutically acceptable compositions that are administered to subjects, such that an effective quantity of the T cells is combined in a mixture with a pharmaceutically acceptable carrier. Suitable carriers are described, for example, in Remington's Pharmaceutical Sciences (Remington's Pharmaceutical Sciences, 20$^{th}$ ed., Mack Publishing Company, Easton, Pa., USA, 2000). On this basis, the compositions may include, albeit not exclusively, solutions of the substances in association with one or more pharmaceutically acceptable carriers or diluents, and contained in buffered solutions with a suitable pH and iso-osmotic with the physiological fluids.

Suitable pharmaceutically acceptable carriers include essentially chemically inert and nontoxic compositions that do not interfere with the effectiveness of the biological activity of the pharmaceutical composition. Examples of suitable pharmaceutical carriers include, but are not limited to, water, saline solutions, glycerol solutions, N-(1(2,3-dioleyloxy)propyl)N,N,N-trimethylammonium chloride (DOTMA), diolesylphosphotidyl-ethanolamine (DOPE), and liposomes. In some embodiments, such compositions contain a therapeutically effective amount of the compound, together with a suitable amount of carrier so as to provide the form for direct administration to the patient.

Pharmaceutical compositions include, without limitation, lyophilized powders or aqueous or non-aqueous sterile injectable solutions or suspensions, which may further contain antioxidants, buffers, bacteriostats and solutes that render the compositions substantially compatible with the tissues or the blood of an intended recipient. Other components that may be present in such compositions include water, surfactants (such as Tween), alcohols, polyols, glycerin and vegetable oils, for example. Extemporaneous injection solutions and suspensions may be prepared from sterile powders, granules, tablets, or concentrated solutions or suspensions.

A pharmaceutical composition disclosed herein may be formulated into a variety of forms and administered by a number of different means. A pharmaceutical formulation may be administered orally, rectally, or parenterally, in formulations containing conventionally acceptable carriers, adjuvants, and vehicles as desired. The term "parenteral" as used herein includes subcutaneous, intravenous, intramuscular, or intrasternal injection and infusion techniques. Administration includes injection or infusion, including intra-arterial, intracardiac, intracerebroventricular, intradermal, intraduodenal, intramedullary, intramuscular, intraosseous, intraperitoneal, intrathecal, intravascular, intravenous, intravitreal, epidural and subcutaneous), inhalational, transdermal, transmucosal, sublingual, buccal and topical (including epicutaneous, dermal, enema, eye drops, ear drops, intranasal, vaginal) administration. In some exemplary embodiments, a route of administration is via an injection such as an intramuscular, intravenous, subcutaneous, or intraperitoneal injection.

Liquid formulations include an oral formulation, an intravenous formulation, an intranasal formulation, an ocular formulation, an otic formulation, an aerosol, and the like. In certain embodiments, a combination of various formulations is administered. In certain embodiments a composition is formulated for an extended release profile.

Methods of Treatment and Use

Disclosed herein, in certain embodiments, are methods of using engineered T cells disclosed herein in the treatment of a BCMA-expressing cancer in an individual in need thereof.

In some embodiments, an antigen-binding domain that binds BCMA of a TAC polypeptide disclosed herein binds to BCMA on a tumor cell. In some embodiments, an antigen-binding domain that binds BCMA of a TAC polypeptide disclosed herein selectively binds to BCMA on a tumor cell.

Disclosed herein, in certain embodiments, are methods of treating a cancer expressing BCMA in an individual in need thereof, comprising administering to the individual an engineered T cell disclosed herein or a pharmaceutical composition comprising an engineered T cell disclosed herein.

Further disclosed herein is use of an engineered T cell disclosed herein in the preparation of a medicament to treat cancer expressing BCMA in an individual in need thereof. Additionally disclosed herein in certain embodiments is the use of an engineered T cell disclosed herein or a pharmaceutical composition disclosed herein to treat a cancer expressing BCMA in an individual in need thereof.

In some embodiments, the engineered T cells disclosed herein are part of a combination therapy. In some embodiments, effectiveness of a therapy disclosed herein is assessed multiple times. In some embodiments, patients are stratified based on a response to a treatment disclosed herein. In some embodiments, an effectiveness of treatment determines entrance into a trial.

In some embodiments, the engineered T cells disclosed herein are administered in combination with a lymphodepleting therapy, or are administered to a subject who has received a lymphodepleting therapy. Examples of lymphodepleting therapies include nonmyeloablative lymphodepleting chemotherapy, myeloablative lymphodepleting chemotherapy, fludarabine, cyclophosphamide, corticosteroids, alemtuzumab, total body irradiation (TBI), and any combination thereof.

Cancers that may be treated with engineered T cells disclosed herein include any form of neoplastic disease. In some embodiments, cancers that are treated include, but are not limited to, multiple myeloma, B cell lymphoma, acute lymphoblastic leukemia (ALL), chronic lymphocytic leukemia (CLL), or Non-Hodgkins Lymphoma.

EXAMPLES

The following examples are given for the purpose of illustrating various embodiments of the invention and are not meant to limit the present invention in any fashion. The present examples, along with the methods described herein are presently representative of preferred embodiments, are exemplary, and are not intended as limitations on the scope of the invention. Changes therein and other uses which are encompassed within the spirit of the invention as defined by the scope of the claims will occur to those skilled in the art.

Example 1—Expression and Characterization of BCMA-TAC T Cells

T cells were engineered to express a BCMA T cell-antigen coupler (TACs) including (i) an antigen-binding domain that binds BCMA, (ii) a UCHT1-based antigen-binding domain that binds CD3, and (iii) a CD4 cytosolic and transmembrane domain. Details of the TAC constructs that were made and tested are shown in Table 6.

TABLE 6

| TAC Construct | BCMA Antigen-Binding Domain | Linker | CD3 Antigen-Binding Domain | Transmembrane/ Cytoplasmic Domain | Amino Acid Sequence |
| --- | --- | --- | --- | --- | --- |
| 1002 | 3625 scFv (VL-VH) | Short Helix Connector | huUCHT1 | CD4 | SEQ ID NO: 75 |
| 1042 | 3625 scFv (VH-VL) | Short Helix Connector | huUCHT1 | CD4 | SEQ ID NO: 76 |
| 1162 | 3625 scFv (VH-VL) | (G4S)4 | huUCHT1 (Y177T) (SEQ ID NO: 26) | CD4 | SEQ ID NO: 73 |
| 1165 | 3625 scFv (VL-VH) | (G4S)4 | huUCHT1 (Y177T) (SEQ ID NO: 26) | CD4 | SEQ ID NO: 69 |

Figure 2:
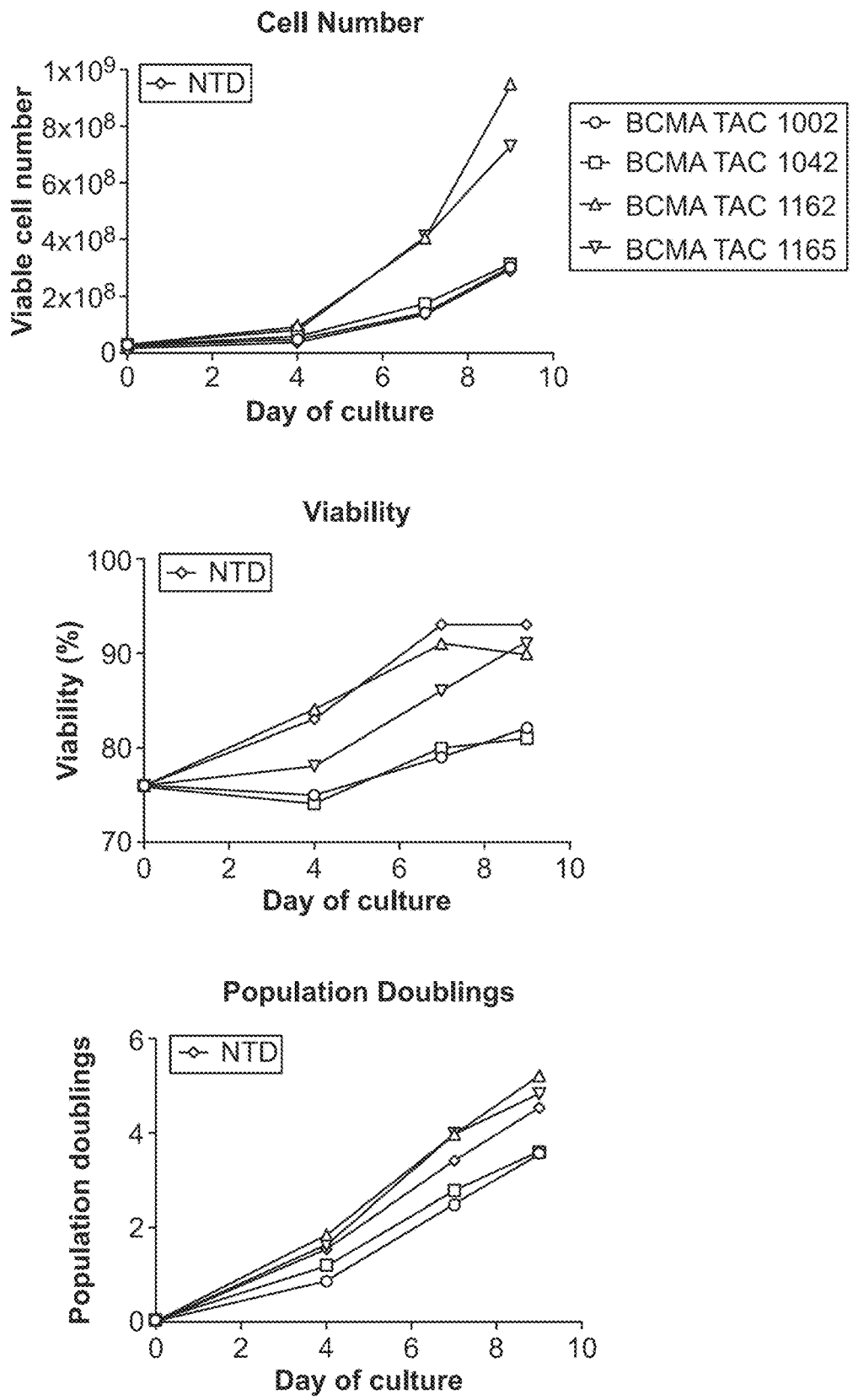
FIG. 2 depicts cell number, viability, and population doubling for T cells engineered to express the indicated TACs

Transduction efficiency was determined by flow cytometry. Surface expression of the BCMA TAC by the T cells was determined by staining T cells with an anti Myc antibody specifically binding to the Myc-Tag incorporated into the TAC receptor. Cell number and viability were determined using automated cell counters, population doubling was calculated based on the final, relative to the initial cell number. Results are shown in FIGS. 1-2 and Table 7. In Table 7, with regard to surface expression, ++ indicates medium and +++ indicates high receptor surface expression as determined via relative MFI values, and with regard to growth, + indicates low +++ indicates medium and ++++ indicates high cell growth rates. Together, the results show that all constructs were successfully transduced and expanded, however levels of expansion varied between the different constructs. In particular, 1162 and 1165 exhibited greater surface expression and growth than 1042 and 1002.

TABLE 7

| Construct | 1042 | 1002 | 1162 | 1165 |
|---|---|---|---|---|
| Transduction Efficiency | 24% | 35% | 30% | 43% |
| Surface Expression | ++ | ++ | +++ | +++ |
| Growth | + | + | ++++ | +++ |

Example 2—In Vivo Activity of BCMA TAC T Cells

BCMA T cell-antigen coupler (TAC) T cells were engineered as described in Example 1 and assayed for in vivo anti-tumor activity.

Mice were intravenously inoculated with $1 \times 10^6$ MM.1S or KMS-11 cells (multiple myeloma cell-lines that express the BCMA antigen) and engineered to express luminescence. Cancer growth was allowed to occur for 12 days. Mice were then treated with 1042, 1002, 1162, or 1165 TAC T cells injected intravenously, each at both a high dose ($4 \times 10^6$ TAC T cells) and a low dose ($1 \times 10^6$ TAC T cells). Each treatment group had 5-8 mice. After treatment, mice were monitored for 30-60 days. Tumor burden was monitored weekly by measuring the bioluminescent signal, expressed as the average radiance. The in vivo cytokine response was measured by collecting blood from animals and isolating the serum which was analyzed for the following cytokines: GM-CSF, IFNγ, IL-1β, IL-1ra, IL-2, IL-4, IL-5, IL-6, IL-8, IL-10, IL-12(p40), IL-12(p70), IL-13, MCP-1, TNFα. Figures show only the relevant T cell cytokines: GM-CSF, IL-2, IFNγ, TNFα, IL-10, IL-4, IL-5, IL-13.

Figure 3:
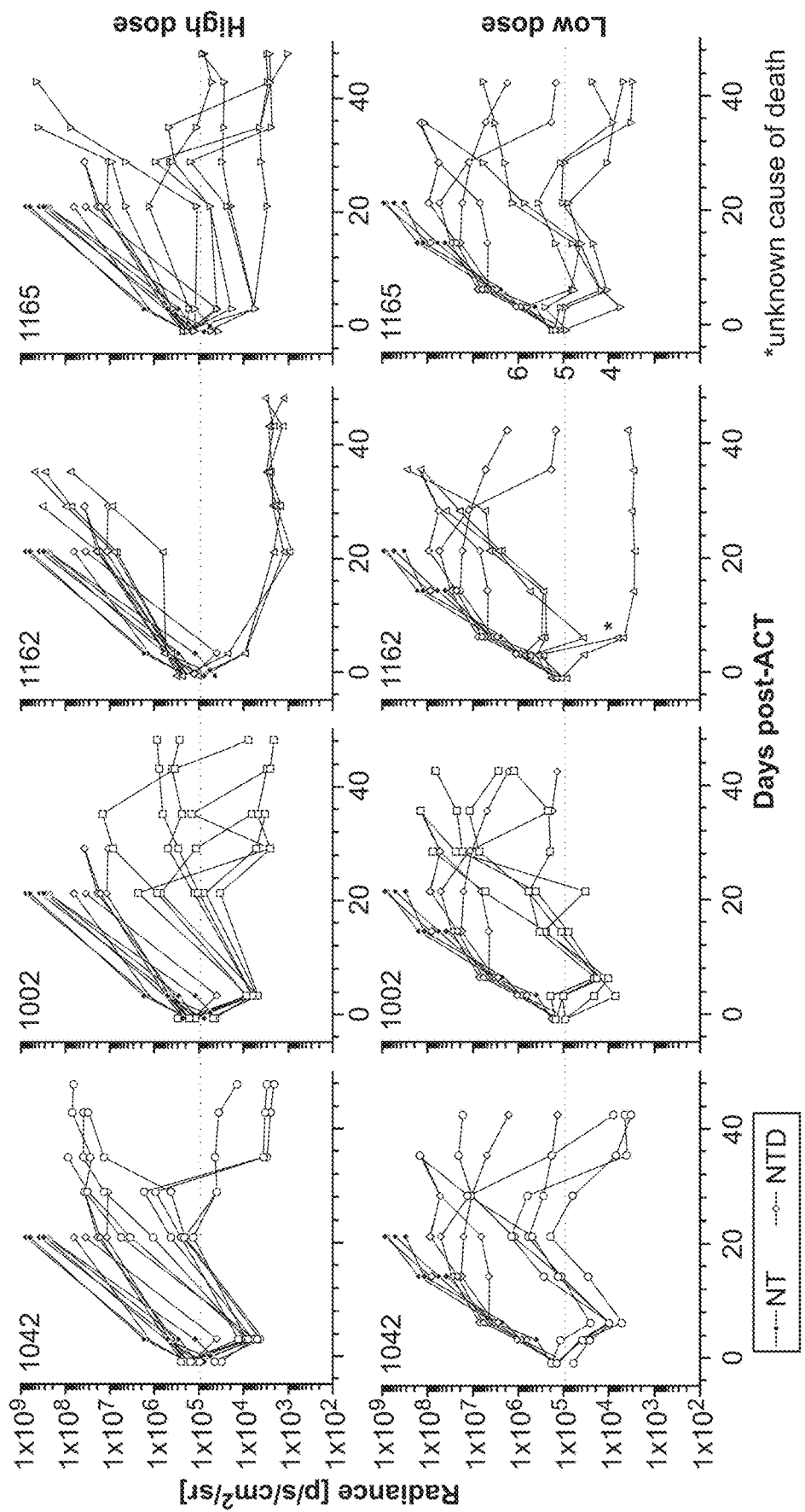
FIG. 3 depicts tumor burden for mice inoculated with MM.1S cancer cells and treated with the indicated TAC T cell at the indicated dose. Each line represents an individual mouse.
Figure 4:
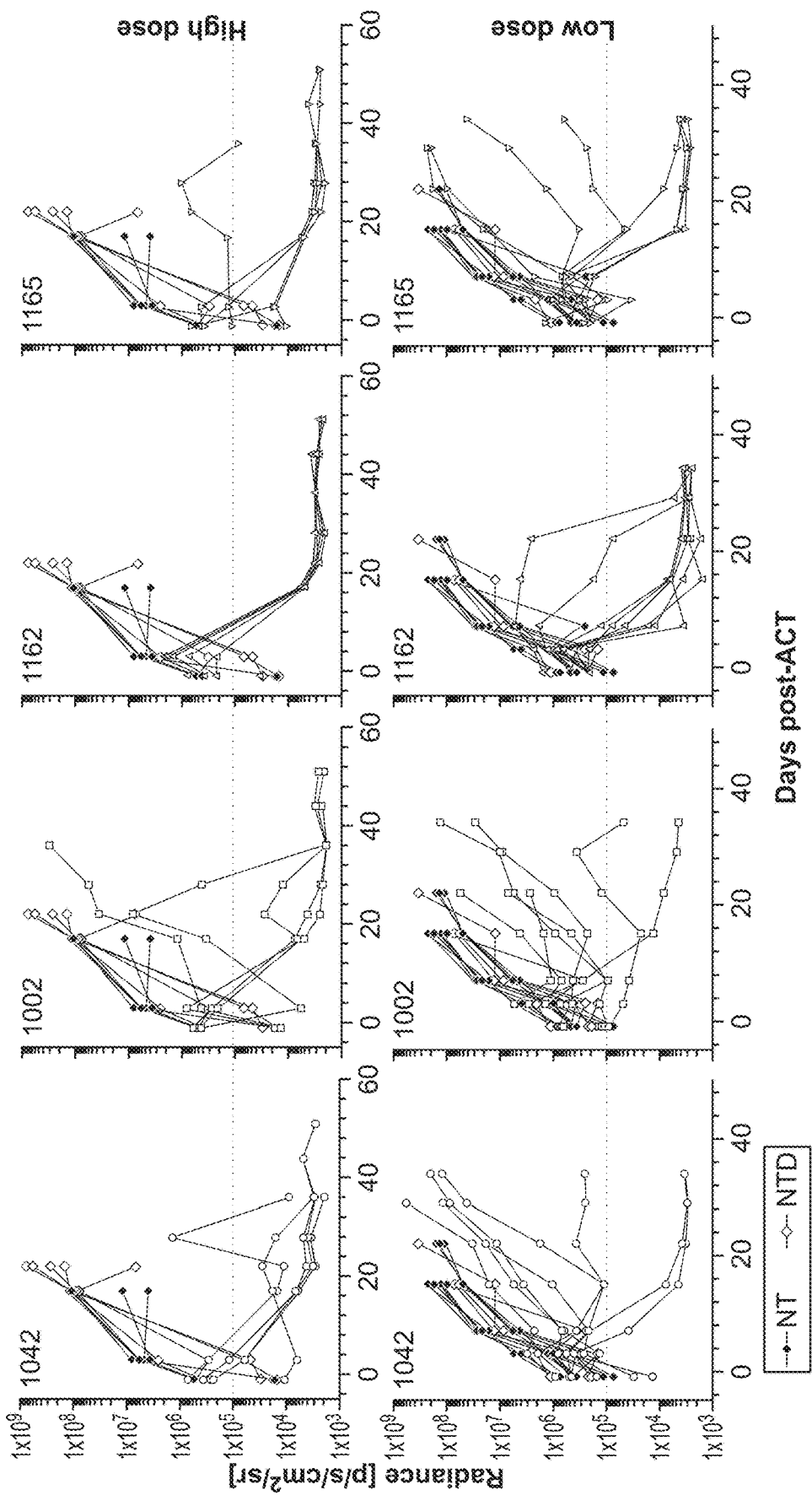
FIG. 4 depicts tumor burden for mice inoculated with KMS-11 cancer cells and treated with the indicated TAC T cell at the indicated dose. Each line represents an individual mouse.
Figure 5:
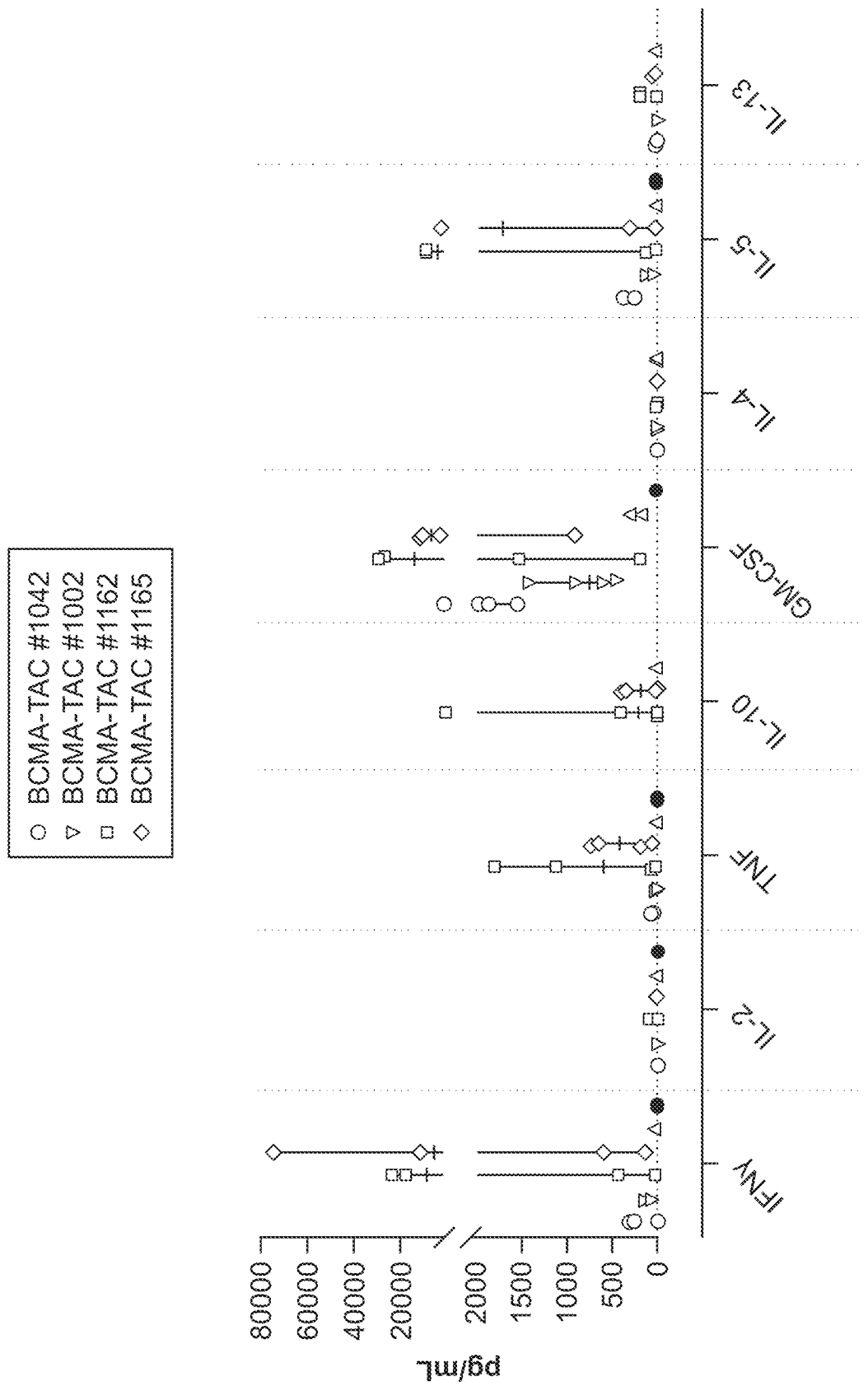
FIG. 5 depicts in vivo cytokine response for mice inoculated with MM.1S cancer cells and treated with a high dose ($4 \times 10^6$ cells) of the indicated TAC T cell. Results are shown for day 3 following treatment.
Figure 6:
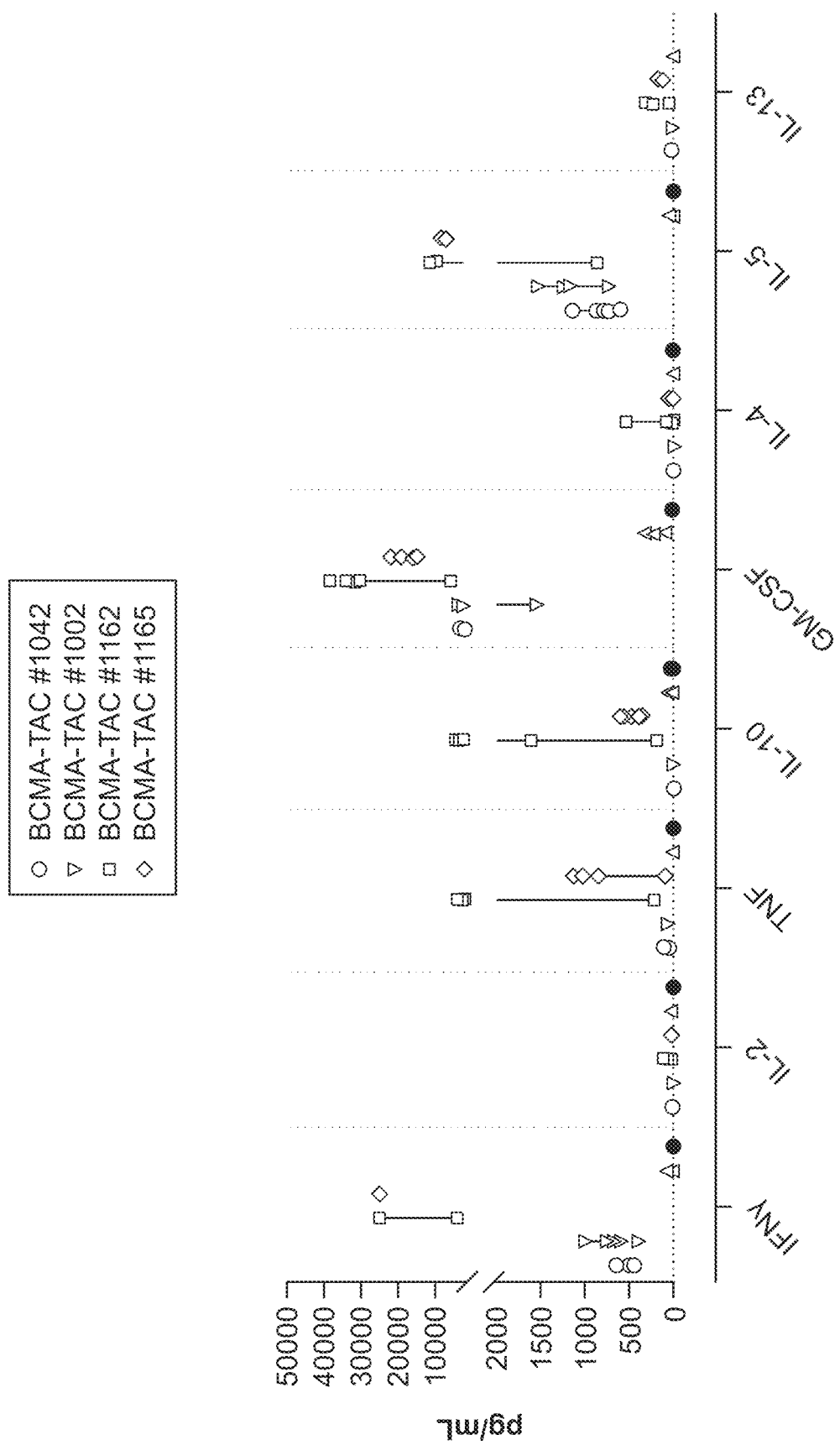
FIG. 6 depicts in vivo cytokine response for mice inoculated with MM.1S cancer cells and treated with a high dose ($4 \times 10^6$ cells) of the indicated TAC T cell. Results are shown for day 6 following treatment.
Figure 7:
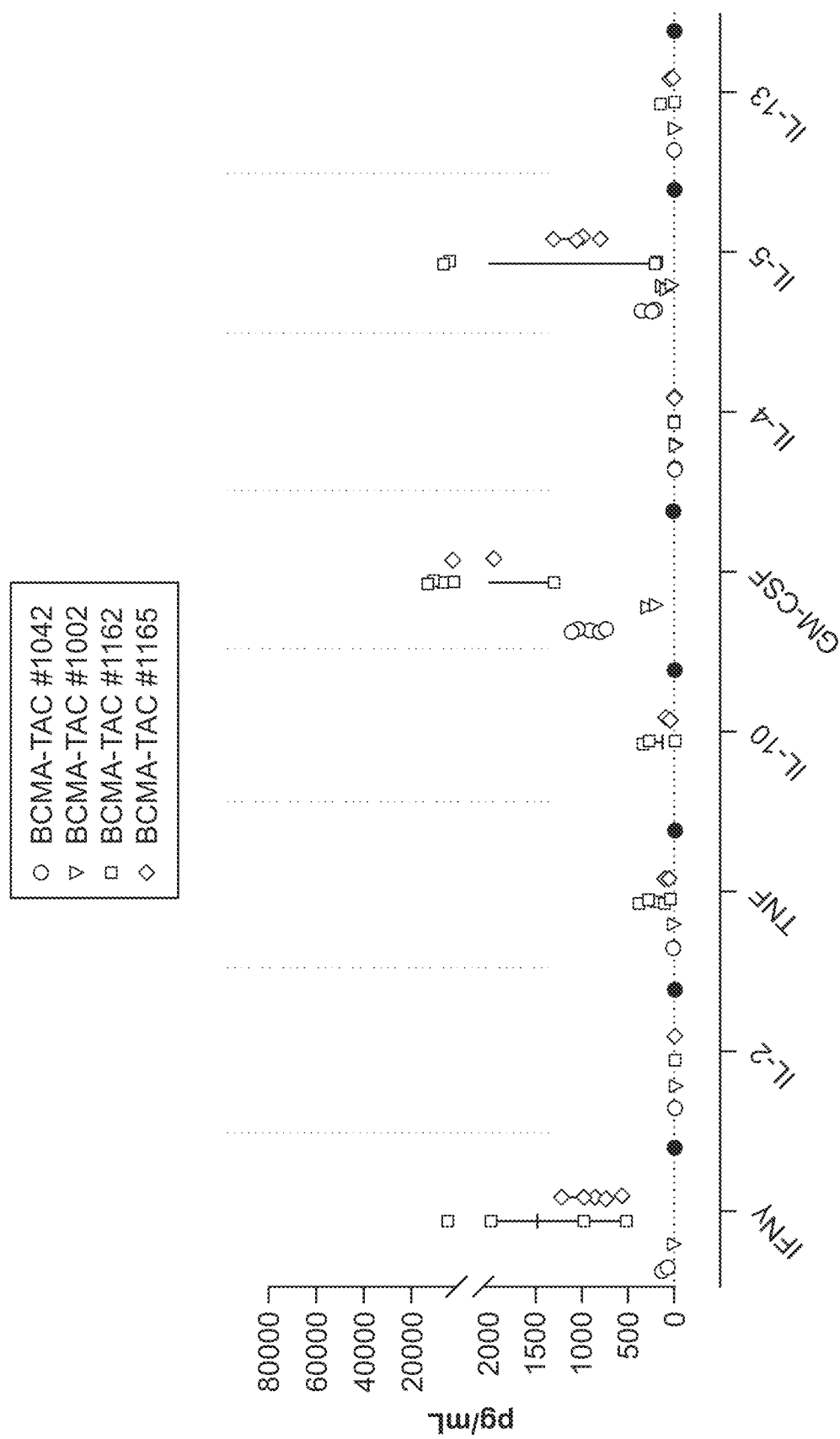
FIG. 7 depicts in vivo cytokine response for mice inoculated with KMS-11 cancer cells and treated with a high dose ($4 \times 10^6$ cells) of the indicated TAC T cell. Results are shown for day 3 following treatment.
Figure 8:
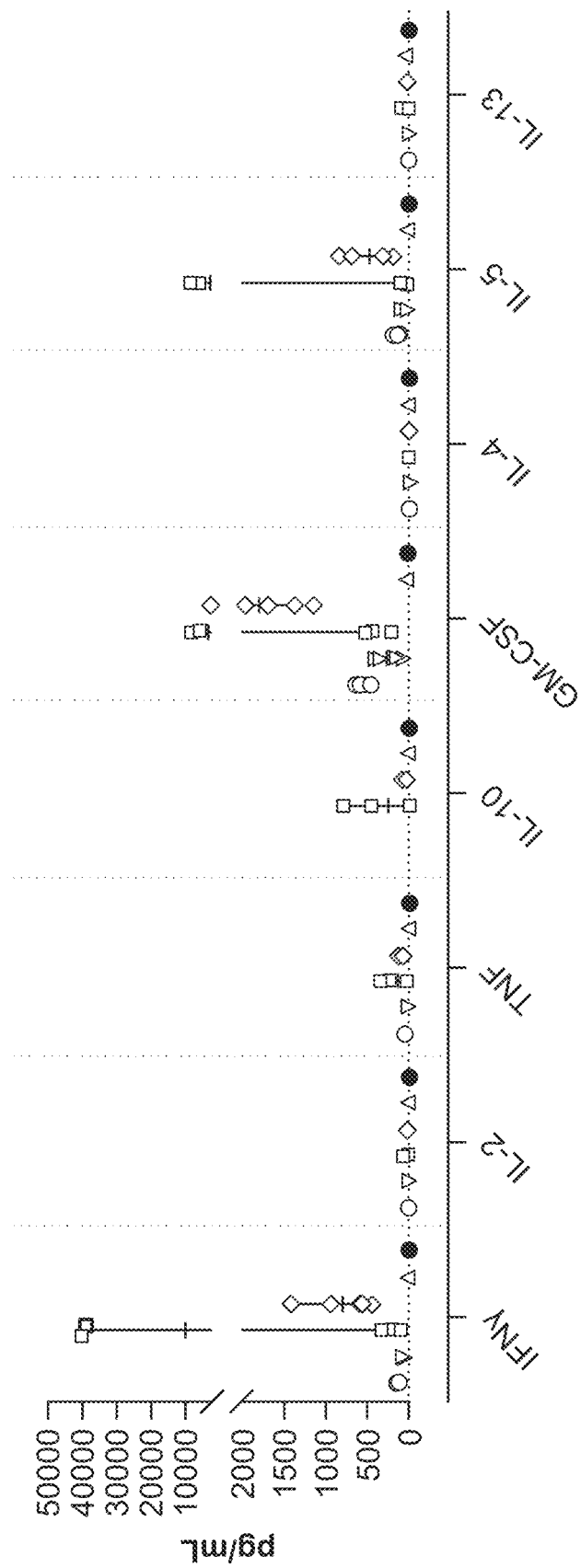
FIG. 8 depicts in vivo cytokine response for mice inoculated with MM.1 S cancer cells and treated with a low dose ($1 \times 10^6$ cells) of the indicated TAC T cell. Results are shown for day 3 following treatment.
Figure 9:
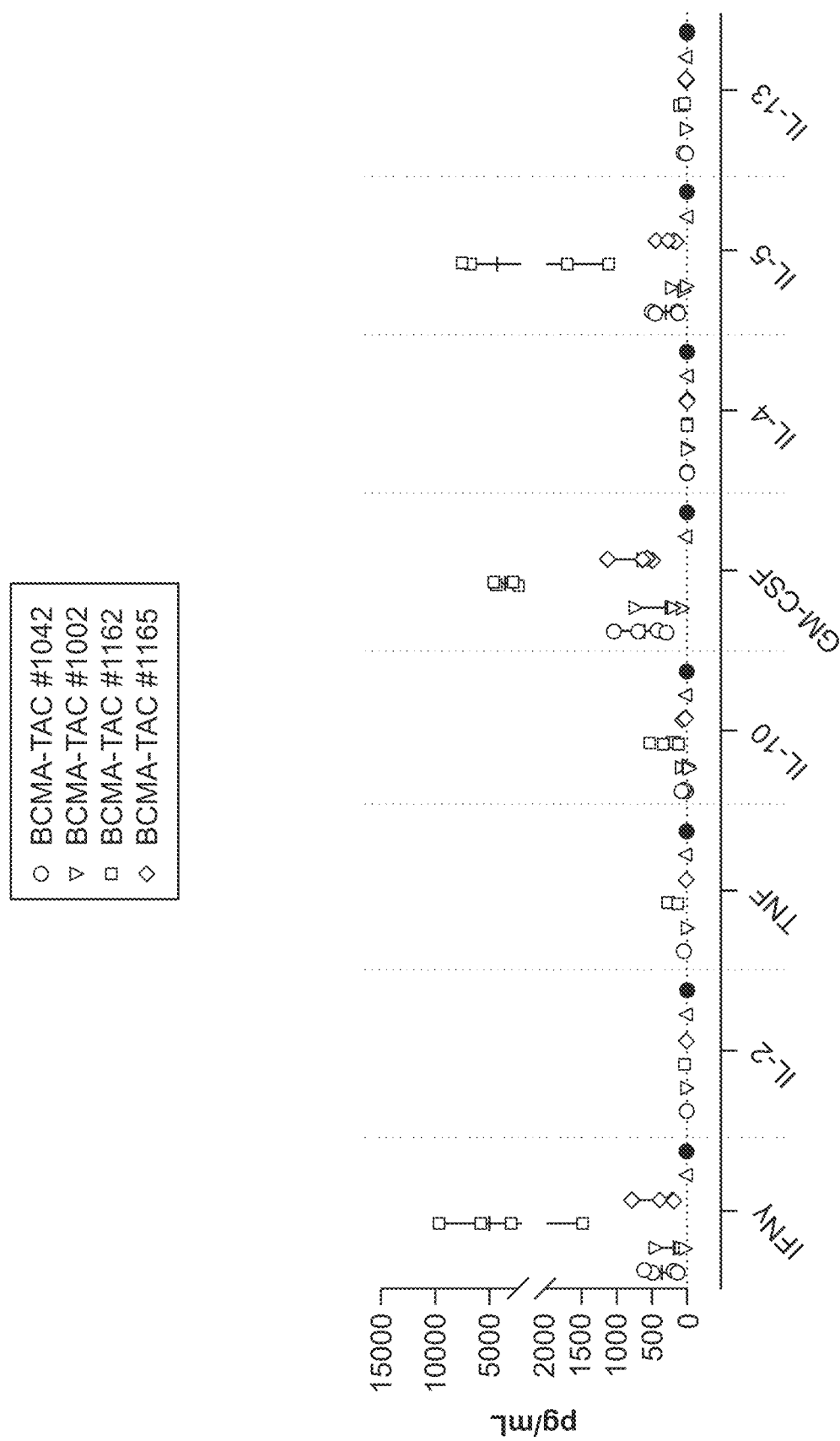
FIG. 9 depicts in vivo cytokine response for mice inoculated with KMS-11 cancer cells and treated with a low dose ($1 \times 10^6$ cells) of the indicated TAC T cell. Results are shown for day 3 following treatment.
Figure 10:
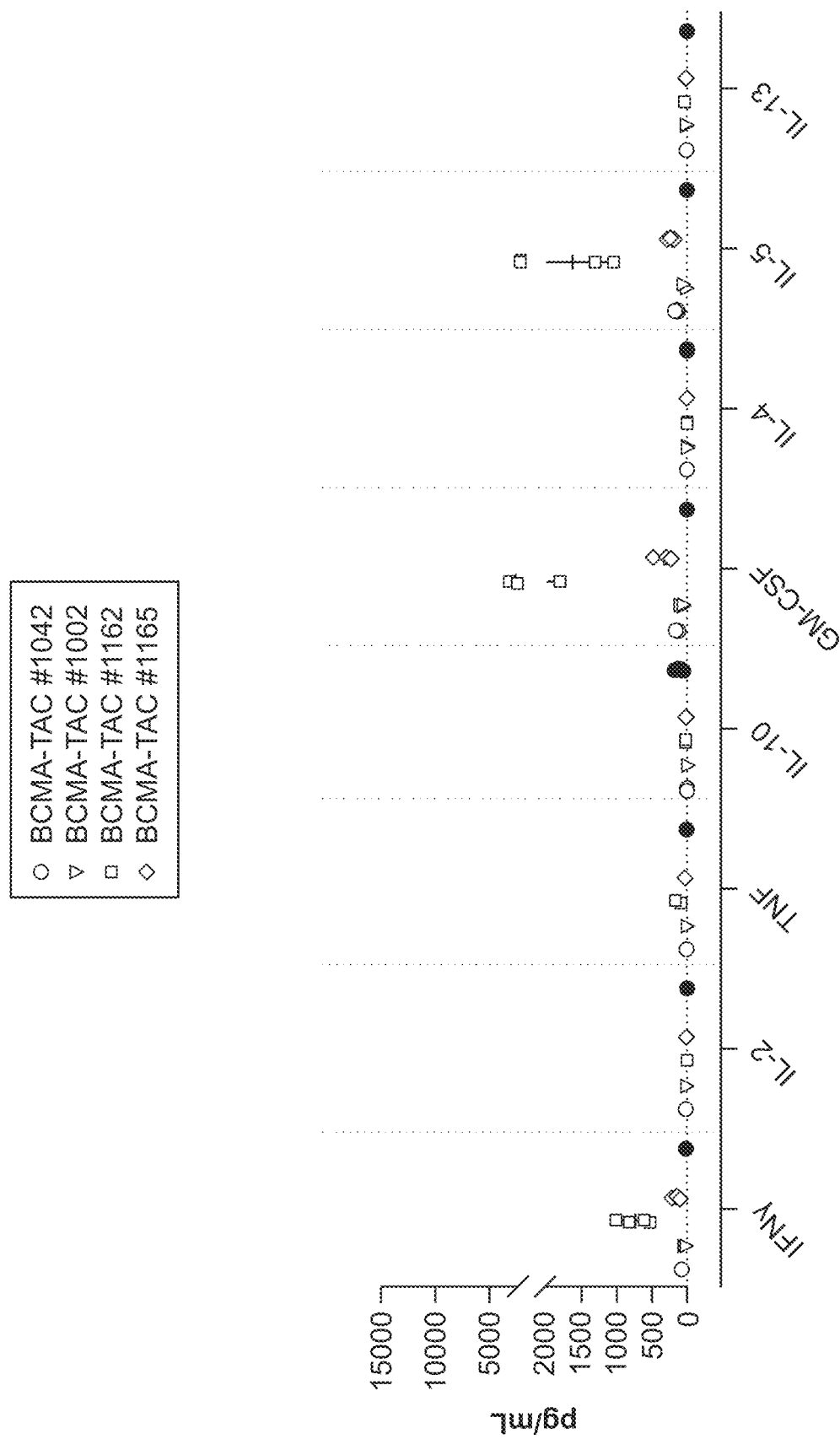
FIG. 10 depicts in vivo cytokine response for mice inoculated with KMS-11 cancer cells and treated with a low dose ($1 \times 10^6$ cells) of the indicated TAC T cell. Results are shown for day 7 following treatment.

Tumor growth curves are depicted in FIGS. 3-4. Tumor growth inhibition is summarized in Table 8. Together, the results show that that while all constructs show anti-tumor efficacy, the 1165 variant overall shows the most consistent anti-tumor response in both tumor models.

TABLE 8

Depicts the amount of ORR (overall response rate) per treatment degroup (ORR is fined as proportion of mice within a group that show a tumor size reduction below the initial tumor burden)

| High Dose | 1042 | 1002 | 1162 | 1165 |
|---|---|---|---|---|
| MM.1S ORR (d3 vs d30) | 100% → 25% | 100% → 43% | 50% → 50% | 63% → 25% |
| KMS-11 ORR (d3 vs d30) | 100% → 60% | 60% → 60% | 0% → 100% | 40% → 80% |

| Low Dose | 1042 | 1002 | 1162 | 1165 |
|---|---|---|---|---|
| MM.1S ORR (d3 vs d30) | 100% → 20% | 60% → 0% | 20% → 25% | 20% → 40% |
| KMS-11 ORR (d3 vs d30) | 13% → 43% | 29% → 25% | 0% → 100% | 25% → 63% |

The in vivo cytokine response is depicted in FIGS. 5-10. Together, the results show that cytokine levels vary greatly between the constructs tested, however TAC treated animals showed, in general, an increase in cytokine levels compared to control animals. In particular, 1162 and 1165 exhibited greater cytokine responses than 1042 and 1002. Further, 1162 shows consistently high levels of cytokine production, whereas 1165 shows an initial increase in cytokine production on day 3 followed by a reduction in cytokine levels on Day 7.

TABLE 9

Final construct summary

| | 1042 | 1002 | 1162 | 1165 |
|---|---|---|---|---|
| Surface expression | ++ | ++ | +++ | +++ |
| Growth | + | + | ++++ | +++ |
| Cytokines | Low | Low | High | High |
| High dose in vivo efficacy | | | | |
| MM.1S ORR (d30) | 25% | 43% | 50% | 25% |
| KMS-11 ORR (d30) | 60% | 60% | 100% | 80% |
| Low dose in vivo efficacy | | | | |
| MM.1S ORR (d30) | 20% | 0% | 25% | 40% |
| KMS-11 ORR (d30) | 43% | 25% | 100% | 63% |

What is claimed is:

1. A polynucleotide encoding a BCMA (B Cell Maturation Antigen) T cell-antigen coupler (BCMA-TAC) polypeptide, comprising the sequence set forth in SEQ ID NO: 68, SEQ ID NO: 70, SEQ ID NO: 72, or SEQ ID NO: 74.

2. The polynucleotide of claim 1, consisting of the sequence set forth in SEQ ID NO: 68, SEQ ID NO: 70, SEQ ID NO: 72, or SEQ ID NO: 74.

3. A recombinant expression vector, comprising the polynucleotide of claim 1.

4. The recombinant expression vector of claim 3, further comprising a promoter functional in a mammalian cell.

5. The recombinant expression vector of claim 3, wherein the expression vector is a lentiviral vector.

6. The recombinant expression vector of claim 5, wherein the lentiviral vector is a VSV-G pseudotyped lentivirus.

7. The recombinant expression vector of claim 3, wherein the expression vector is a γ retroviral vector.

8. The recombinant expression vector of claim 7, wherein the γ retroviral vector is a GALV pseudotyped γ-retrovirus.

9. A BCMA (B Cell Maturation Antigen) T cell-antigen coupler (BCMA-TAC) polypeptide, comprising the sequence set forth in SEQ ID NO: 67, SEQ ID NO: 69, SEQ ID NO: 71, or SEQ ID NO: 73.

10. The BCMA-TAC polypeptide of claim 9, consisting of the sequence set forth in SEQ ID NO: 67, SEQ ID NO: 69, SEQ ID NO: 71, or SEQ ID NO: 73.

11. An engineered T cell expressing the polynucleotide of claim 1.

12. An engineered T cell, comprising the recombinant expression vector of claim 3.

13. An engineered T cell, comprising a polynucleotide encoding the BCMA-TAC polypeptide of claim 9.

14. An engineered T cell, comprising the BCMA-TAC polypeptide of claim 9, wherein the BCMA-TAC polypeptide is expressed on the surface of the engineered T cell.

15. A pharmaceutical composition, comprising the engineered T cell of claim 14, and a pharmaceutically acceptable excipient.

* * * * *

SEQUENCE LISTING

<160> NUMBER OF SEQ ID NOS: 76

<210> SEQ ID NO 1
<211> LENGTH: 54
<212> TYPE: DNA
<213> ORGANISM: Mus sp.
<220> FEATURE:
<223> OTHER INFORMATION: muIgG leader (secretion signal)

<400> SEQUENCE: 1
atggatttcc aggtccagat tttctccttc ctgctgattt ccgcaagcgt catt        54

<210> SEQ ID NO 2
<211> LENGTH: 18
<212> TYPE: PRT
<213> ORGANISM: Mus sp.
<220> FEATURE:
<223> OTHER INFORMATION: muIgG leader (secretion signal)

<400> SEQUENCE: 2

Met Asp Phe Gln Val Gln Ile Phe Ser Phe Leu Leu Ile Ser Ala Ser
1               5                   10                  15

Val Ile

<210> SEQ ID NO 3
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Myc Tag

<400> SEQUENCE: 3
gaacagaaac tgattagcga agaagacctg                                   30

<210> SEQ ID NO 4
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Myc Tag

<400> SEQUENCE: 4

Glu Gln Lys Leu Ile Ser Glu Glu Asp Leu
1               5                   10

<210> SEQ ID NO 5
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Linker 1

<400> SEQUENCE: 5
actagtggcg gaggaggatc actcgag                                      27

<210> SEQ ID NO 6
<211> LENGTH: 9
<212> TYPE: PRT

<213> ORGANISM: Artificial Sequence
<220> FEATURE:
<223> OTHER INFORMATION: Description of Artificial Sequence: Synthetic
       peptide
<220> FEATURE:
<223> OTHER INFORMATION: Linker 1

<400> SEQUENCE: 6

Thr Ser Gly Gly Gly Gly Ser Leu Glu
1               5

<210> SEQ ID NO 7
<211> LENGTH: 75
<212> TYPE: DNA
<213> ORGANISM: Artificial Sequence
<220> FEATURE:
<223> OTHER INFORMATION: Description of Artificial Sequence: Synthetic
       oligonucleotide
<220> FEATURE:
<223> OTHER INFORMATION: Linker 2

<400> SEQUENCE: 7
aaccccgggg gaggaggagg gagcggggga ggaggcagcg gcggggggagg ctctggagga    60 ggagggagcg gatcc                                                     75

<210> SEQ ID NO 8
<211> LENGTH: 25
<212> TYPE: PRT
<213> ORGANISM: Artificial Sequence
<220> FEATURE:
<223> OTHER INFORMATION: Description of Artificial Sequence: Synthetic
       peptide
<220> FEATURE:
<223> OTHER INFORMATION: Linker 2

<400> SEQUENCE: 8

Asn Pro Gly Gly Gly Gly Gly Ser Gly Gly Gly Ser Gly Gly Gly
1               5                   10                  15

Gly Ser Gly Gly Gly Gly Ser Gly Ser
            20                  25

<210> SEQ ID NO 9
<211> LENGTH: 66
<212> TYPE: DNA
<213> ORGANISM: Artificial Sequence
<220> FEATURE:
<223> OTHER INFORMATION: Description of Artificial Sequence: Synthetic
       oligonucleotide
<220> FEATURE:
<223> OTHER INFORMATION: CD4 based linker

<400> SEQUENCE: 9
agcggacagg tgctgctgga atccaatatc aaagtcctgc ccacttggtc taccccgtg    60 cagcct                                                              66

<210> SEQ ID NO 10
<211> LENGTH: 22
<212> TYPE: PRT
<213> ORGANISM: Artificial Sequence
<220> FEATURE:
<223> OTHER INFORMATION: Description of Artificial Sequence: Synthetic
       peptide
<220> FEATURE:
<223> OTHER INFORMATION: CD4 based linker

<400> SEQUENCE: 10

Ser Gly Gln Val Leu Leu Glu Ser Asn Ile Lys Val Leu Pro Thr Trp

```
1               5                   10                  15

Ser Thr Pro Val Gln Pro
            20

<210> SEQ ID NO 11
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Short Helix connector

<400> SEQUENCE: 11
gccgaagcag cagcaaagga ggccgcagcg aaggaagcag ctgcgaaggc c          51

<210> SEQ ID NO 12
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Short Helix connector

<400> SEQUENCE: 12

Ala Glu Ala Ala Ala Lys Glu Ala Ala Ala Lys Glu Ala Ala Ala Lys
1               5                   10                  15

Ala

<210> SEQ ID NO 13
<211> LENGTH: 81
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Long Helix connector

<400> SEQUENCE: 13
gccgaggcag ctgcaaagga agctgcggcg aaggaggccg cagcgaaaga agcagcggca      60
aaagaagcag ccgccaaagc c                                                81

<210> SEQ ID NO 14
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Long Helix connector

<400> SEQUENCE: 14

Ala Glu Ala Ala Ala Lys Glu Ala Ala Ala Lys Glu Ala Ala Ala Lys
1               5                   10                  15

Glu Ala Ala Ala Lys Glu Ala Ala Ala Lys Ala
            20                  25

<210> SEQ ID NO 15
<211> LENGTH: 576
<212> TYPE: DNA
<213> ORGANISM: Artificial Sequence
```

```
<220> FEATURE:
<223> OTHER INFORMATION: Description of Artificial Sequence: Synthetic
      polynucleotide
<220> FEATURE:
<223> OTHER INFORMATION: Large domain connector

<400> SEQUENCE: 15
atcgtagtgt tggcatttca aaaagcgtct agcatcgtct ataagaagga aggtgaacaa        60
gtcgagtttt ctttccccct tgcatttacg gtggaaaagc ttacgggtag cggcgagctg       120
tggtggcaag ctgaacgggc ttcaagctca aaatcttgga ttacttttga cttgaagaac       180
aaagaggtga gtgtcaaaag agttactcag gacccaaagc ttcaaatggg gaagaaactt       240
ccgctgcacc tgacgttgcc tcaggccctg cctcaatatg ccggctcagg caatctgacc       300
ctcgcgctgg aagctaagac cggaaaattg caccaggaag tcaatttggt tgtgatgcgc       360
gccactcagc tccaaaaaaa tctcacttgc gaggtatggg ggcctacgag cccaaaactt       420
atgctgtctt tgaagcttga aaacaaggaa gcgaaagttt ctaagcgcga gaaagcggta       480
tgggttttga atcctgaggc tggaatgtgg caatgcctcc tgagcgatag cgggcaggtg       540
ctgttggaga gcaacatcaa ggttttgcca gcagcc                                576

<210> SEQ ID NO 16
<211> LENGTH: 192
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Large domain connector

<400> SEQUENCE: 16

Ile Val Val Leu Ala Phe Gln Lys Ala Ser Ser Ile Val Tyr Lys Lys
 1               5                  10                  15

Glu Gly Glu Gln Val Glu Phe Ser Phe Pro Leu Ala Phe Thr Val Glu
            20                  25                  30

Lys Leu Thr Gly Ser Gly Glu Leu Trp Trp Gln Ala Glu Arg Ala Ser
        35                  40                  45

Ser Ser Lys Ser Trp Ile Thr Phe Asp Leu Lys Asn Lys Glu Val Ser
    50                  55                  60

Val Lys Arg Val Thr Gln Asp Pro Lys Leu Gln Met Gly Lys Lys Leu
65                  70                  75                  80

Pro Leu His Leu Thr Leu Pro Gln Ala Leu Pro Gln Tyr Ala Gly Ser
                85                  90                  95

Gly Asn Leu Thr Leu Ala Leu Glu Ala Lys Thr Gly Lys Leu His Gln
            100                 105                 110

Glu Val Asn Leu Val Val Met Arg Ala Thr Gln Leu Gln Lys Asn Leu
        115                 120                 125

Thr Cys Glu Val Trp Gly Pro Thr Ser Pro Lys Leu Met Leu Ser Leu
    130                 135                 140

Lys Leu Glu Asn Lys Glu Ala Lys Val Ser Lys Arg Glu Lys Ala Val
145                 150                 155                 160

Trp Val Leu Asn Pro Glu Ala Gly Met Trp Gln Cys Leu Leu Ser Asp
                165                 170                 175

Ser Gly Gln Val Leu Leu Glu Ser Asn Ile Lys Val Leu Pro Ala Ala
            180                 185                 190

<210> SEQ ID NO 17
```

```
<211> LENGTH: 60
<212> TYPE: DNA
<213> ORGANISM: Homo sapiens
<220> FEATURE:
<223> OTHER INFORMATION: huIgG

<400> SEQUENCE: 17
atggagaccc ccgcccagct gctgttcctg ctgctgctgt ggctgcccga caccaccggc      60

<210> SEQ ID NO 18
<211> LENGTH: 20
<212> TYPE: PRT
<213> ORGANISM: Homo sapiens
<220> FEATURE:
<223> OTHER INFORMATION: huIgG

<400> SEQUENCE: 18

Met Glu Thr Pro Ala Gln Leu Leu Phe Leu Leu Leu Leu Trp Leu Pro
1               5                   10                  15

Asp Thr Thr Gly
            20

<210> SEQ ID NO 19
<211> LENGTH: 63
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: huCD8a (1162)

<400> SEQUENCE: 19
atggccctgc cagtgaccgc cctgctgctg ccactggccc tgctgctgca cgccgccaga      60
ccc                                                                   63

<210> SEQ ID NO 20
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: huCD8a (1162)

<400> SEQUENCE: 20

Met Ala Leu Pro Val Thr Ala Leu Leu Leu Pro Leu Ala Leu Leu Leu
1               5                   10                  15

His Ala Ala Arg Pro
            20

<210> SEQ ID NO 21
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Whitlow

<400> SEQUENCE: 21
ggatctacca gcggatccgg caagcctggc agcggagagg gatccacaaa ggga            54

<210> SEQ ID NO 22
```

```
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Whitlow

<400> SEQUENCE: 22

Gly Ser Thr Ser Gly Ser Gly Lys Pro Gly Ser Gly Glu Gly Ser Thr
1               5                   10                  15

Lys Gly

<210> SEQ ID NO 23
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: (G4S)3 linker

<400> SEQUENCE: 23
ggcggcggcg gaagtggagg aggaggctca ggcggaggag ggagc             45

<210> SEQ ID NO 24
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: (G4S)3 linker

<400> SEQUENCE: 24

Gly Gly Gly Gly Ser Gly Gly Gly Gly Ser Gly Gly Gly Gly Ser
1               5                   10                  15

<210> SEQ ID NO 25
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: (G4S)4-based linker

<400> SEQUENCE: 25
ggaggaggag ggagcggggg aggaggcagc ggcggggag gctctggagg aggagggagc    60

<210> SEQ ID NO 26
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: (G4S)4-based linker

<400> SEQUENCE: 26

Gly Gly Gly Gly Ser Gly Gly Gly Gly Ser Gly Gly Gly Gly Ser Gly
1               5                   10                  15

Gly Gly Gly Ser
```

<210> SEQ ID NO 27
<211> LENGTH: 15
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: G4S-based linker

<400> SEQUENCE: 27
ggaggaggag ggagc                                                  15

<210> SEQ ID NO 28
<211> LENGTH: 5
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: G4S-based linker

<400> SEQUENCE: 28

Gly Gly Gly Gly Ser
1               5

<210> SEQ ID NO 29
<211> LENGTH: 63
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: huCD8a (1165)

<400> SEQUENCE: 29
atggccctgc cagtgaccgc cctgctgctg ccactggccc tgctgctgca cgccgcccgg    60
cct                                                                 63

<210> SEQ ID NO 30
<211> LENGTH: 21
<212> TYPE: PRT
<213> ORGANISM: Artificial Sequence
<220> FEATURE:
<223> OTHER INFORMATION: Description of Artificial Sequence: Synthetic peptide
<220> FEATURE:
<223> OTHER INFORMATION: huCD8a (1165)

<400> SEQUENCE: 30

Met Ala Leu Pro Val Thr Ala Leu Leu Leu Pro Leu Ala Leu Leu Leu
1               5                   10                  15

His Ala Ala Arg Pro
            20

<210> SEQ ID NO 31
<211> LENGTH: 750
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: UCHT11

<400> SEQUENCE: 31

```
atggacatcc agatgactca gaccacaagc tccctgtctg caagtctggg cgaccgggtg      60
acaatctcct gcagagcctc tcaggatatt aggaactacc tgaattggta tcagcagaaa     120
cctgatggca cagtcaagct gctgatctac tataccagcc ggctgcactc aggcgtgcca     180
agcaaattct caggaagcgg ctccgggact gactactccc tgaccatctc taacctggag     240
caggaagata ttgctaccta tttctgccag cagggcaata cactgccctg gacttttgcc     300
ggaggcacca aactggagat caagggggga ggcgggagtg gaggcggggg atcaggagga     360
ggaggcagcg gaggaggagg gtccgaggtc cagctgcagc agagcggacc agaactggtg     420
aagcccggag caagtatgaa aatctcctgt aaggcctcag gatacagctt caccggctat     480
acaatgaact gggtgaaaca gtcccatggc aagaacctgg aatggatggg gctgattaat     540
ccttacaaag gcgtcagcac ctataatcag aagtttaaag acaaggccac actgactgtg     600
gataagtcta gttcaaccgc ttacatggag ctgctgtccc tgacatctga agacagtgcc     660
gtgtactatt gtgctcggtc tggctactat ggggacagtg attggtactt cgatgtctgg     720
ggacagggca ctaccctgac cgtgttttct                                      750
```

<210> SEQ ID NO 32
<211> LENGTH: 250
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: UCHT12

<400> SEQUENCE: 32

```
Met Asp Ile Gln Met Thr Gln Thr Thr Ser Ser Leu Ser Ala Ser Leu
1               5                   10                  15

Gly Asp Arg Val Thr Ile Ser Cys Arg Ala Ser Gln Asp Ile Arg Asn
            20                  25                  30

Tyr Leu Asn Trp Tyr Gln Gln Lys Pro Asp Gly Thr Val Lys Leu Leu
        35                  40                  45

Ile Tyr Tyr Thr Ser Arg Leu His Ser Gly Val Pro Ser Lys Phe Ser
    50                  55                  60

Gly Ser Gly Ser Gly Thr Asp Tyr Ser Leu Thr Ile Ser Asn Leu Glu
65                  70                  75                  80

Gln Glu Asp Ile Ala Thr Tyr Phe Cys Gln Gln Gly Asn Thr Leu Pro
                85                  90                  95

Trp Thr Phe Ala Gly Gly Thr Lys Leu Glu Ile Lys Gly Gly Gly Gly
            100                 105                 110

Ser Gly Gly Gly Gly Ser Gly Gly Gly Gly Ser Gly Gly Gly Gly Ser
        115                 120                 125

Glu Val Gln Leu Gln Gln Ser Gly Pro Glu Leu Val Lys Pro Gly Ala
    130                 135                 140

Ser Met Lys Ile Ser Cys Lys Ala Ser Gly Tyr Ser Phe Thr Gly Tyr
145                 150                 155                 160

Thr Met Asn Trp Val Lys Gln Ser His Gly Lys Asn Leu Glu Trp Met
                165                 170                 175

Gly Leu Ile Asn Pro Tyr Lys Gly Val Ser Thr Tyr Asn Gln Lys Phe
            180                 185                 190

Lys Asp Lys Ala Thr Leu Thr Val Asp Lys Ser Ser Ser Thr Ala Tyr
```

```
                195                 200                 205
Met Glu Leu Leu Ser Leu Thr Ser Glu Asp Ser Ala Val Tyr Tyr Cys
            210                 215                 220

Ala Arg Ser Gly Tyr Tyr Gly Asp Ser Asp Trp Tyr Phe Asp Val Trp
225                 230                 235                 240

Gly Gln Gly Thr Thr Leu Thr Val Phe Ser
            245                 250
```

<210> SEQ ID NO 33
<211> LENGTH: 769
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: OKT3

<400> SEQUENCE: 33

```
atggccgaca tcgtgctgac acagagcccc gccatcatgt ctgccagccc tggcgagaaa    60
gtgaccatga cctgtagcgc cagcagcagc gtgtcctaca tgaactggta tcagcagaag   120
tccggcacca gccccaagcg tggatctac gacacaagca gctggcctc tggcgtgccc    180
gcccacttta gaggctctgg cagcggcaca agctacagcc tgaccatcag cggcatggaa   240
gccgaggatg ccgccaccta ctactgccag cagtggtcca gcaaccctt cacctttggc   300
tccggcacaa agctggaaat caaccgggcc gacaccgccc ctacaggcgg cggaggatct   360
ggcggaggcg gatctggggg cggaggaagt ggggggggag gatctatggc tcaggtgcag   420
ctgcagcagt ctggcgccga actggctaga cctggcgcct ccgtgaagat gagctgcaag   480
gccagcggct acaccttcac ccggtacacc atgcactggg tcaagcagag gcctggacag   540
ggcctggaat ggatcggcta catcaacccc agccggggct acaccaacta caaccagaag   600
ttcaaggaca aggccaccct gaccaccgac aagagcagca gcaccgccta catgcagctg   660
tcctccctga ccagcgagga cagcgccgtg tactactgcg cccggtacta cgacgaccac   720
tactccctgg actactgggg ccagggcacc acactgaccg tgtctagta               769
```

<210> SEQ ID NO 34
<211> LENGTH: 256
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: OKT3

<400> SEQUENCE: 34

```
Met Ala Asp Ile Val Leu Thr Gln Ser Pro Ala Ile Met Ser Ala Ser
1               5                   10                  15

Pro Gly Glu Lys Val Thr Met Thr Cys Ser Ala Ser Ser Ser Val Ser
            20                  25                  30

Tyr Met Asn Trp Tyr Gln Gln Lys Ser Gly Thr Ser Pro Lys Arg Trp
        35                  40                  45

Ile Tyr Asp Thr Ser Lys Leu Ala Ser Gly Val Pro Ala His Phe Arg
    50                  55                  60

Gly Ser Gly Ser Gly Thr Ser Tyr Ser Leu Thr Ile Ser Gly Met Glu
65                  70                  75                  80

Ala Glu Asp Ala Ala Thr Tyr Tyr Cys Gln Gln Trp Ser Ser Asn Pro
```

```
                85                  90                  95
Phe Thr Phe Gly Ser Gly Thr Lys Leu Glu Ile Asn Arg Ala Asp Thr
            100                 105                 110

Ala Pro Thr Gly Gly Gly Ser Gly Gly Gly Ser Gly Gly Gly
        115                 120                 125

Gly Ser Gly Gly Gly Ser Met Ala Gln Val Gln Leu Gln Gln Ser
    130                 135                 140

Gly Ala Glu Leu Ala Arg Pro Gly Ala Ser Val Lys Met Ser Cys Lys
145                 150                 155                 160

Ala Ser Gly Tyr Thr Phe Thr Arg Tyr Thr Met His Trp Val Lys Gln
                165                 170                 175

Arg Pro Gly Gln Gly Leu Glu Trp Ile Gly Tyr Ile Asn Pro Ser Arg
            180                 185                 190

Gly Tyr Thr Asn Tyr Asn Gln Lys Phe Lys Asp Lys Ala Thr Leu Thr
        195                 200                 205

Thr Asp Lys Ser Ser Ser Thr Ala Tyr Met Gln Leu Ser Ser Leu Thr
    210                 215                 220

Ser Glu Asp Ser Ala Val Tyr Tyr Cys Ala Arg Tyr Tyr Asp Asp His
225                 230                 235                 240

Tyr Ser Leu Asp Tyr Trp Gly Gln Gly Thr Thr Leu Thr Val Ser Ser
                245                 250                 255
```

<210> SEQ ID NO 35
<211> LENGTH: 747
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: F6A

<400> SEQUENCE: 35

```
cagaccgtgg tgacccagga gcccagcctg accgtgagcc ccggcggcac cgtgaccctg      60
acctgcggca gcagcaccgg cgccgtgacc agcggctact accccaactg ggtgcagcag     120
aagcccggcc aggccccag gggcctgatc ggcggcacca agttcctggc ccccggcacc     180
cccgccaggt tcagcggcag cctgctgggc ggcaaggccg ccctgaccct gagcggcgtg     240
cagcccgagg acgaggccga gtactactgc gccctgtggt acagcaacag gtgggtgttc     300
ggcggcggca ccaagctgac cgtgctgggc ggcggcggca gcggcggcgg cggcagcggc     360
ggcggcggca gcgaggtgca gctgctggag agcggcggcg gcctggtgca gcccggcggc     420
agcctgaagc tgagctgcgc cgccagcggc ttcaccttca acatctacgc catgaactgg     480
gtgaggcagg cccccggcaa gggcctggag tgggtggcca ggatcaggag caagtacaac     540
aactacgcca cctactacgc cgacagcgtg aagagcaggt tcaccatcag cagggacgac     600
agcaagaaca ccgcctacct gcagatgaac aacctgaaga ccgaggacac cgccgtgtac     660
tactgcgtga ggcacggcaa cttcggcaac agctacgtga gcttcttcgc ctactggggc     720
cagggcaccc tggtgaccgt gagcagc                                          747
```

<210> SEQ ID NO 36
<211> LENGTH: 249
<212> TYPE: PRT
<213> ORGANISM: Artificial Sequence
<220> FEATURE:
<223> OTHER INFORMATION: Description of Artificial Sequence: Synthetic
      polypeptide

<220> FEATURE:
<223> OTHER INFORMATION: F6A

<400> SEQUENCE: 36

Gln Thr Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Ser Gly
            20                  25                  30

Tyr Tyr Pro Asn Trp Val Gln Gln Lys Pro Gly Gln Ala Pro Arg Gly
        35                  40                  45

Leu Ile Gly Gly Thr Lys Phe Leu Ala Pro Gly Thr Pro Ala Arg Phe
    50                  55                  60

Ser Gly Ser Leu Leu Gly Gly Lys Ala Ala Leu Thr Leu Ser Gly Val
65                  70                  75                  80

Gln Pro Glu Asp Glu Ala Glu Tyr Tyr Cys Ala Leu Trp Tyr Ser Asn
                85                  90                  95

Arg Trp Val Phe Gly Gly Gly Thr Lys Leu Thr Val Leu Gly Gly Gly
            100                 105                 110

Gly Ser Gly Gly Gly Gly Ser Gly Gly Gly Ser Glu Val Gln Leu
        115                 120                 125

Leu Glu Ser Gly Gly Gly Leu Val Gln Pro Gly Gly Ser Leu Lys Leu
    130                 135                 140

Ser Cys Ala Ala Ser Gly Phe Thr Phe Asn Ile Tyr Ala Met Asn Trp
145                 150                 155                 160

Val Arg Gln Ala Pro Gly Lys Gly Leu Glu Trp Val Ala Arg Ile Arg
                165                 170                 175

Ser Lys Tyr Asn Asn Tyr Ala Thr Tyr Tyr Ala Asp Ser Val Lys Ser
            180                 185                 190

Arg Phe Thr Ile Ser Arg Asp Asp Ser Lys Asn Thr Ala Tyr Leu Gln
        195                 200                 205

Met Asn Asn Leu Lys Thr Glu Asp Thr Ala Val Tyr Tyr Cys Val Arg
    210                 215                 220

His Gly Asn Phe Gly Asn Ser Tyr Val Ser Phe Phe Ala Tyr Trp Gly
225                 230                 235                 240

Gln Gly Thr Leu Val Thr Val Ser Ser
                245

<210> SEQ ID NO 37
<211> LENGTH: 720
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: L2K

<400> SEQUENCE: 37
gacatccagc tgacccagag ccccgccatc atgagcgcca gccccggcga gaaggtgacc    60
atgacctgca gggccagcag cagcgtgagc tacatgaact ggtaccagca gaagagcggc   120
accagcccca gaggtggat ctacgacacc agcaaggtgg ccagcggcgt gccctacagg    180
ttcagcggca gcggcagcgg caccagctac agcctgacca tcagcagcat ggaggccgag   240
gacgccgcca cctactactg ccagcagtgg agcagcaacc ccctgacctt cggcgccggc   300
accaagctgg agctgaaggg cggcggcggc agcggcggcg gcggcagcgg cggcggcggc   360
agcgacatca gctgcagca gagcggcgcc gagctggcca ggcccggcgc cagcgtgaag   420

```
atgagctgca agaccagcgg ctacaccttc accaggtaca ccatgcactg ggtgaagcag    480
aggcccggcc agggcctgga gtggatcggc tacatcaacc ccagcagggg ctacaccaac    540
tacaaccaga agttcaagga caaggccacc ctgaccaccg acaagagcag cagcaccgcc    600
tacatgcagc tgagcagcct gaccagcgag gacagcgccg tgtactactg cgccaggtac    660
tacgacgacc actactgcct ggactactgg ggccagggca ccaccctgac cgtgagcagc    720
```

<210> SEQ ID NO 38
<211> LENGTH: 240
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: L2K

<400> SEQUENCE: 38

```
Asp Ile Gln Leu Thr Gln Ser Pro Ala Ile Met Ser Ala Ser Pro Gly
1               5                   10                  15

Glu Lys Val Thr Met Thr Cys Arg Ala Ser Ser Val Ser Tyr Met
            20                  25                  30

Asn Trp Tyr Gln Gln Lys Ser Gly Thr Ser Pro Lys Arg Trp Ile Tyr
        35                  40                  45

Asp Thr Ser Lys Val Ala Ser Gly Val Pro Tyr Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ser Ser Asn Pro Leu Thr
                85                  90                  95

Phe Gly Ala Gly Thr Lys Leu Glu Leu Lys Gly Gly Gly Gly Ser Gly
            100                 105                 110

Gly Gly Gly Ser Gly Gly Gly Gly Ser Asp Ile Lys Leu Gln Gln Ser
        115                 120                 125

Gly Ala Glu Leu Ala Arg Pro Gly Ala Ser Val Lys Met Ser Cys Lys
    130                 135                 140

Thr Ser Gly Tyr Thr Phe Thr Arg Tyr Thr Met His Trp Val Lys Gln
145                 150                 155                 160

Arg Pro Gly Gln Gly Leu Glu Trp Ile Gly Tyr Ile Asn Pro Ser Arg
                165                 170                 175

Gly Tyr Thr Asn Tyr Asn Gln Lys Phe Lys Asp Lys Ala Thr Leu Thr
            180                 185                 190

Thr Asp Lys Ser Ser Ser Thr Ala Tyr Met Gln Leu Ser Ser Leu Thr
        195                 200                 205

Ser Glu Asp Ser Ala Val Tyr Tyr Cys Ala Arg Tyr Tyr Asp Asp His
    210                 215                 220

Tyr Cys Leu Asp Tyr Trp Gly Gln Gly Thr Thr Leu Thr Val Ser Ser
225                 230                 235                 240
```

<210> SEQ ID NO 39
<211> LENGTH: 735
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: huUCHT1

<400> SEQUENCE: 39

```
atggatatcc agatgaccca gtccccgagc tccctgtccg cctctgtggg cgatagggtc      60
accatcacct gccgtgccag tcaggacatc cgtaattatc tgaactggta tcaacagaaa     120
ccaggaaaag ctccgaaact actgatttac tatacctccc gcctggagtc tggagtccct     180
tctcgcttct ctggttctgg ttctgggacg gattacactc tgaccatcag cagtctgcaa     240
ccggaagact cgcaactta ttactgtcag caaggtaata ctctgccgtg gacgttcgga     300
cagggcacca aggtggagat caaaggcggc ggcggaagtg gaggaggagg ctcaggcgga     360
ggagggagcg aggttcagct ggtggagtct ggcggtggcc tggtgcagcc aggggggctca    420
ctccgtttgt cctgtgcagc ttctggctac tcctttaccg gctacactat gaactgggtg     480
cgtcaggccc caggtaaggg cctggaatgg gttgcactga ttaatcctta taaaggtgtt     540
agtacctaca accagaagtt caaggaccgt ttcactataa gcgtagataa atccaaaaac     600
acagcctacc tgcaaatgaa cagcctgcgt gctgaggaca ctgccgtcta ttattgtgct     660
agaagcggat actacggcga tagtgactgg tatttttgacg tgtggggtca aggaaccctg     720
gtcaccgtct cctcg                                                      735
```

<210> SEQ ID NO 40
<211> LENGTH: 245
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: huUCHT1

<400> SEQUENCE: 40

```
Met Asp Ile Gln Met Thr Gln Ser Pro Ser Ser Leu Ser Ala Ser Val
1               5                   10                  15
Gly Asp Arg Val Thr Ile Thr Cys Arg Ala Ser Gln Asp Ile Arg Asn
                20                  25                  30
Tyr Leu Asn Trp Tyr Gln Gln Lys Pro Gly Lys Ala Pro Lys Leu Leu
            35                  40                  45
Ile Tyr Tyr Thr Ser Arg Leu Glu Ser Gly Val Pro Ser Arg Phe Ser
        50                  55                  60
Gly Ser Gly Ser Gly Thr Asp Tyr Thr Leu Thr Ile Ser Ser Leu Gln
65                  70                  75                  80
Pro Glu Asp Phe Ala Thr Tyr Tyr Cys Gln Gln Gly Asn Thr Leu Pro
                85                  90                  95
Trp Thr Phe Gly Gln Gly Thr Lys Val Glu Ile Lys Gly Gly Gly Gly
            100                 105                 110
Ser Gly Gly Gly Gly Ser Gly Gly Gly Ser Glu Val Gln Leu Val
        115                 120                 125
Glu Ser Gly Gly Gly Leu Val Gln Pro Gly Gly Ser Leu Arg Leu Ser
    130                 135                 140
Cys Ala Ala Ser Gly Tyr Ser Phe Thr Gly Tyr Thr Met Asn Trp Val
145                 150                 155                 160
Arg Gln Ala Pro Gly Lys Gly Leu Glu Trp Val Ala Leu Ile Asn Pro
                165                 170                 175
Tyr Lys Gly Val Ser Thr Tyr Asn Gln Lys Phe Lys Asp Arg Phe Thr
            180                 185                 190
Ile Ser Val Asp Lys Ser Lys Asn Thr Ala Tyr Leu Gln Met Asn Ser
```

```
                  195                 200                 205
Leu Arg Ala Glu Asp Thr Ala Val Tyr Tyr Cys Ala Arg Ser Gly Tyr
            210                 215                 220

Tyr Gly Asp Ser Asp Trp Tyr Phe Asp Val Trp Gly Gln Gly Thr Leu
225                 230                 235                 240

Val Thr Val Ser Ser
                245

<210> SEQ ID NO 41
<211> LENGTH: 735
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: huUCHT1 (Y177T)

<400> SEQUENCE: 41
atggatatcc agatgaccca gtccccgagc tccctgtccg cctctgtggg cgatagggtc      60
accatcacct gccgtgccag tcaggacatc cgtaattatc tgaactggta tcaacagaaa     120
ccaggaaaag ctccgaaact actgatttac tatacctccc gcctggagtc tggagtccct     180
tctcgcttct ctggttctgg ttctgggacg gattacactc tgaccatcag cagtctgcaa     240
ccggaagact tcgcaactta ttactgtcag caagtaata  ctctgccgtg acgttcgga      300 cagggcacca aggtggagat caaaggcggc ggcggaagtg gaggaggagg ctcaggcgga     360
ggagggagcg aggttcagct ggtggagtct ggcggtggcc tggtgcagcc aggggggctca    420 ctccgtttgt cctgtgcagc ttctggctac tcctttaccg gctacactat gaactgggtg     480
cgtcaggccc caggtaaggg cctggaatgg gttgcactga ttaatcctac aaaggtgtt     540 agtacctaca ccagaagtt caaggaccgt ttcactataa gcgtagataa atccaaaaac     600
acagcctacc tgcaaatgaa cagcctgcgt gctgaggaca ctgccgtcta ttattgtgct     660
agaagcggat actacggcga tagtgactgg tattttgacg tgtggggtca aggaaccctg     720
gtcaccgtct cctcg                                                      735

<210> SEQ ID NO 42
<211> LENGTH: 245
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: huUCHT1 (Y177T)

<400> SEQUENCE: 42

Met Asp Ile Gln Met Thr Gln Ser Pro Ser Ser Leu Ser Ala Ser Val
1               5                  10                  15

Gly Asp Arg Val Thr Ile Thr Cys Arg Ala Ser Gln Asp Ile Arg Asn
            20                  25                  30

Tyr Leu Asn Trp Tyr Gln Gln Lys Pro Gly Lys Ala Pro Lys Leu Leu
        35                  40                  45

Ile Tyr Tyr Thr Ser Arg Leu Glu Ser Gly Val Pro Ser Arg Phe Ser
    50                  55                  60

Gly Ser Gly Ser Gly Thr Asp Tyr Thr Leu Thr Ile Ser Ser Leu Gln
65                  70                  75                  80

Pro Glu Asp Phe Ala Thr Tyr Tyr Cys Gln Gln Gly Asn Thr Leu Pro
```

```
                85                  90                  95
Trp Thr Phe Gly Gln Gly Thr Lys Val Glu Ile Lys Gly Gly Gly
                100                 105                 110

Ser Gly Gly Gly Ser Gly Gly Gly Ser Glu Val Gln Leu Val
        115                 120                 125

Glu Ser Gly Gly Gly Leu Val Gln Pro Gly Gly Ser Leu Arg Leu Ser
    130                 135                 140

Cys Ala Ala Ser Gly Tyr Ser Phe Thr Gly Tyr Thr Met Asn Trp Val
145                 150                 155                 160

Arg Gln Ala Pro Gly Lys Gly Leu Glu Trp Val Ala Leu Ile Asn Pro
                165                 170                 175

Thr Lys Gly Val Ser Thr Tyr Asn Gln Lys Phe Lys Asp Arg Phe Thr
            180                 185                 190

Ile Ser Val Asp Lys Ser Lys Asn Thr Ala Tyr Leu Gln Met Asn Ser
        195                 200                 205

Leu Arg Ala Glu Asp Thr Ala Val Tyr Tyr Cys Ala Arg Ser Gly Tyr
    210                 215                 220

Tyr Gly Asp Ser Asp Trp Tyr Phe Asp Val Trp Gly Gln Gly Thr Leu
225                 230                 235                 240

Val Thr Val Ser Ser
                245

<210> SEQ ID NO 43
<211> LENGTH: 750
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: UCHT1 (Y182T)

<400> SEQUENCE: 43
atggacatcc agatgactca gaccacaagc tccctgtctg caagtctggg cgaccgggtg      60
acaatctcct gcagagcctc tcaggatatt aggaactacc tgaattggta tcagcagaaa    120
cctgatggca cagtcaagct gctgatctac tataccagcc ggctgcactc aggcgtgcca    180
agcaaattct caggaagcgg ctccgggact gactactccc tgaccatctc taacctggag    240
caggaagata ttgctaccta tttctgccag cagggcaata cactgccctg gacttttgcc    300
ggaggcacca aactggagat caaggggggga ggcgggagtg gaggcggggg atcaggagga    360
ggaggcagcg aggaggaggg gtccgaggtc cagctgcagc agagcggacc agaactggtg    420
aagcccggag caagtatgaa aatctcctgt aaggcctcag atacagcttc accggctat    480 acaatgaact gggtgaaaca gtcccatggc aagaacctgg aatggatggg gctgattaat    540
cctaccaaag gcgtcagcac ctataatcag aagtttaaag acaaggccac actgactgtg    600
gataagtcta gttcaaccgc ttacatggag ctgctgtccc tgacatctga agacagtgcc    660
gtgtactatt gtgctcggtc tggctactat ggggacagtg attggtactt cgatgtctgg    720
ggacagggca ctaccctgac cgtgttttct                                      750

<210> SEQ ID NO 44
<211> LENGTH: 250
<212> TYPE: PRT
<213> ORGANISM: Artificial Sequence
<220> FEATURE:
<223> OTHER INFORMATION: Description of Artificial Sequence: Synthetic
      polypeptide
```

<220> FEATURE:
<223> OTHER INFORMATION: UCHT1 (Y182T)

<400> SEQUENCE: 44

Met Asp Ile Gln Met Thr Gln Thr Thr Ser Ser Leu Ser Ala Ser Leu
1               5                   10                  15

Gly Asp Arg Val Thr Ile Ser Cys Arg Ala Ser Gln Asp Ile Arg Asn
            20                  25                  30

Tyr Leu Asn Trp Tyr Gln Gln Lys Pro Asp Gly Thr Val Lys Leu Leu
        35                  40                  45

Ile Tyr Tyr Thr Ser Arg Leu His Ser Gly Val Pro Ser Lys Phe Ser
    50                  55                  60

Gly Ser Gly Ser Gly Thr Asp Tyr Ser Leu Thr Ile Ser Asn Leu Glu
65                  70                  75                  80

Gln Glu Asp Ile Ala Thr Tyr Phe Cys Gln Gln Gly Asn Thr Leu Pro
                85                  90                  95

Trp Thr Phe Ala Gly Gly Thr Lys Leu Glu Ile Lys Gly Gly Gly Gly
            100                 105                 110

Ser Gly Gly Gly Gly Ser Gly Gly Gly Gly Ser Gly Gly Gly Gly Ser
        115                 120                 125

Glu Val Gln Leu Gln Gln Ser Gly Pro Glu Leu Val Lys Pro Gly Ala
    130                 135                 140

Ser Met Lys Ile Ser Cys Lys Ala Ser Gly Tyr Ser Phe Thr Gly Tyr
145                 150                 155                 160

Thr Met Asn Trp Val Lys Gln Ser His Gly Lys Asn Leu Glu Trp Met
                165                 170                 175

Gly Leu Ile Asn Pro Thr Lys Gly Val Ser Thr Tyr Asn Gln Lys Phe
            180                 185                 190

Lys Asp Lys Ala Thr Leu Thr Val Asp Lys Ser Ser Ser Thr Ala Tyr
        195                 200                 205

Met Glu Leu Leu Ser Leu Thr Ser Glu Asp Ser Ala Val Tyr Tyr Cys
    210                 215                 220

Ala Arg Ser Gly Tyr Tyr Gly Asp Ser Asp Trp Tyr Phe Asp Val Trp
225                 230                 235                 240

Gly Gln Gly Thr Thr Leu Thr Val Phe Ser
                245                 250

<210> SEQ ID NO 45
<211> LENGTH: 252
<212> TYPE: DNA
<213> ORGANISM: Homo sapiens
<220> FEATURE:
<223> OTHER INFORMATION: CD4 Domain1

<400> SEQUENCE: 45
agcggacagg tgctgctgga atccaatatc aaagtcctgc ccacttggtc taccccgtg      60 cagcctatgg ctctgattgt gctgggagga gtcgcaggac tgctgctgtt tatcgggctg    120
ggaattttct tttgcgtgcg ctgccggcac cggagaaggc aggccgagcg catgagccag    180
atcaagcgac tgctgagcga gaagaaaacc tgtcagtgtc cccatagatt ccagaagacc    240
tgttcaccca tt                                                        252

<210> SEQ ID NO 46
<211> LENGTH: 84
<212> TYPE: PRT
<213> ORGANISM: Homo sapiens
<220> FEATURE:

<223> OTHER INFORMATION: CD4 Domain2

<400> SEQUENCE: 46

Ser Gly Gln Val Leu Leu Glu Ser Asn Ile Lys Val Leu Pro Thr Trp
1               5                   10                  15

Ser Thr Pro Val Gln Pro Met Ala Leu Ile Val Leu Gly Gly Val Ala
            20                  25                  30

Gly Leu Leu Leu Phe Ile Gly Leu Gly Ile Phe Phe Cys Val Arg Cys
        35                  40                  45

Arg His Arg Arg Arg Gln Ala Glu Arg Met Ser Gln Ile Lys Arg Leu
    50                  55                  60

Leu Ser Glu Lys Lys Thr Cys Gln Cys Pro His Arg Phe Gln Lys Thr
65                  70                  75                  80

Cys Ser Pro Ile

<210> SEQ ID NO 47
<211> LENGTH: 237
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: CD8alpha Domain

<400> SEQUENCE: 47
ctcgagctga ggcccgaggc ttctagacct gctgccggcg agccgtgca caccagaggc    60 ctggacttcg ccagcgacat ctacatctgg gcccctctgg ccggcacctg tggcgtgctg   120
ctgctgagcc tggtcatcac cctgtactgc aaccaccgga accggcggag agtgtgcaag   180
tgccccagac ccgtggtcaa gagcggcgac aagcccagcc tgagcgccag atacgtg     237

<210> SEQ ID NO 48
<211> LENGTH: 79
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CD8alpha Domain

<400> SEQUENCE: 48

Leu Glu Leu Arg Pro Glu Ala Ser Arg Pro Ala Ala Gly Gly Ala Val
1               5                   10                  15

His Thr Arg Gly Leu Asp Phe Ala Ser Asp Ile Tyr Ile Trp Ala Pro
            20                  25                  30

Leu Ala Gly Thr Cys Gly Val Leu Leu Leu Ser Leu Val Ile Thr Leu
        35                  40                  45

Tyr Cys Asn His Arg Asn Arg Arg Val Cys Lys Cys Pro Arg Pro
    50                  55                  60

Val Val Lys Ser Gly Asp Lys Pro Ser Leu Ser Ala Arg Tyr Val
65                  70                  75

<210> SEQ ID NO 49
<211> LENGTH: 234
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:

-continued

<223> OTHER INFORMATION: CD8alpha+R(beta) Domain

<400> SEQUENCE: 49

```
ctcgagctga ggcccgaggc ttctagacct gctgccggcg agccgtgca caccagaggc    60
ctggacttcg ccagcgacat ctacatctgg gcccctctgg ccggcacctg tggcgtgctg   120
ctgctgagcc tggtcatcac cctgtacctg tgctgcagac ggcggagagt gtgcaagtgc   180
cccagacccg tggtcaagag cggcgacaag cccagcctga cgccagata cgtg          234
```

<210> SEQ ID NO 50
<211> LENGTH: 78
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CD8alpha+R(beta) Domain

<400> SEQUENCE: 50

```
Leu Glu Leu Arg Pro Glu Ala Ser Arg Pro Ala Ala Gly Gly Ala Val
1               5                   10                  15
His Thr Arg Gly Leu Asp Phe Ala Ser Asp Ile Tyr Ile Trp Ala Pro
            20                  25                  30
Leu Ala Gly Thr Cys Gly Val Leu Leu Leu Ser Leu Val Ile Thr Leu
        35                  40                  45
Tyr Leu Cys Cys Arg Arg Arg Val Cys Lys Cys Pro Arg Pro Val
    50                  55                  60
Val Lys Ser Gly Asp Lys Pro Ser Leu Ser Ala Arg Tyr Val
65                  70                  75
```

<210> SEQ ID NO 51
<211> LENGTH: 213
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: CD8 alpha +Lck Domain

<400> SEQUENCE: 51

```
ctcgagaaga agtccaccct gaagaaacgg gtgtcccggc tgcccagacc cgagacacag    60
aagggccccc tgagcagccc tatcaccctg gactgctgg tggccggcgt gctggtgctg   120
ctggtgtctc tgggagtggc catccacctg tgctgccggc ggagaagggc ctgcaagtgc   180
cccagactgc ggttcatgaa gcagttctac aag                                213
```

<210> SEQ ID NO 52
<211> LENGTH: 71
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: CD8 alpha +Lck Domain

<400> SEQUENCE: 52

```
Leu Glu Lys Lys Ser Thr Leu Lys Lys Arg Val Ser Arg Leu Pro Arg
1               5                   10                  15
Pro Glu Thr Gln Lys Gly Pro Leu Ser Ser Pro Ile Thr Leu Gly Leu
            20                  25                  30
```

```
Leu Val Ala Gly Val Leu Val Leu Val Ser Leu Gly Val Ala Ile
        35                  40                  45

His Leu Cys Cys Arg Arg Arg Ala Cys Lys Cys Pro Arg Leu Arg
    50                  55                  60

Phe Met Lys Gln Phe Tyr Lys
65                  70
```

<210> SEQ ID NO 53
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: 3625 VL - CDR1

<400> SEQUENCE: 53

```
Ser Val Ser Ser Ala
1               5
```

<210> SEQ ID NO 54
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: 3625 VL - CDR2

<400> SEQUENCE: 54

```
Ser Ala Ser Ser Leu Tyr Ser
1               5
```

<210> SEQ ID NO 55
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: 3625 VL - CDR3

<400> SEQUENCE: 55

```
Ser Val Trp Val Gly Tyr Ser Leu Ile
1               5
```

<210> SEQ ID NO 56
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 3625 VL

<400> SEQUENCE: 56

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Ala
            20                  25                  30

Val Ala Trp Tyr Gln Gln Lys Pro Gly Lys Ala Pro Lys Leu Leu Ile
        35                  40                  45
```

```
Tyr Ser Ala Ser Ser Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Val Trp Val Gly Tyr
                85                  90                  95

Ser Leu Ile Thr Phe Gly Gln Gly Thr Lys Val Glu Ile Lys
                100                 105                 110

<210> SEQ ID NO 57
<211> LENGTH: 330
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: 3625 VL

<400> SEQUENCE: 57
gacatccaga tgacacagtc cccatccagc ctcagcgctt ccgtgggaga cagagtgacc      60
atcacatgca gggcaagcca gtccgtgtct agcgccgtgg catggtacca gcagaagccc    120
ggcaaggccc ctaagctgct gatctacagc gcctcctctc tgtattccgg cgtgccatct    180
cggttctctg gcagcagatc cggcaccgac tttacccctga caatcagctc cctgcagccc    240
gaggatttcg ccacatacta ttgccagcag agcgtgtggg tgggctactc cctgatcacc    300
tttggccagg gcacaaaagt cgaaattaag                                     330

<210> SEQ ID NO 58
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: 3625 VH - CDR1

<400> SEQUENCE: 58

Ile Tyr Tyr Ser Tyr Met
1               5

<210> SEQ ID NO 59
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: 3625 VH - CDR2

<400> SEQUENCE: 59

Ser Ile Ser Pro Tyr Tyr Gly Tyr Thr Ser
1               5                   10

<210> SEQ ID NO 60
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
```

<223> OTHER INFORMATION: 3625 VH - CDR3

<400> SEQUENCE: 60

His Gly Tyr Ala Leu
1               5

<210> SEQ ID NO 61
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 3625 VH

<400> SEQUENCE: 61

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Tyr Tyr Ser
            20                  25                  30

Tyr Met His Trp Val Arg Gln Ala Pro Gly Lys Gly Leu Glu Trp Val
        35                  40                  45

Ala Ser Ile Ser Pro Tyr Tyr Gly Tyr Thr Ser Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg His Gly Tyr Ala Leu Asp Tyr Trp Gly Gln Gly Thr Leu Val
            100                 105                 110

Thr Val Ser Ser
        115

<210> SEQ ID NO 62
<211> LENGTH: 348
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: 3625 VH

<400> SEQUENCE: 62
gaggtgcagc tcgtggaaag cggcggaggg ctggtccagc caggcggctc tctgaggctg      60
agctgtgcag catccggctt caacatctac tatagctaca tgcattgggt ccgccaggct     120
cctggcaaag gactggaatg ggtggcctct atcagccctt actatggcta cacctcttat     180
gccgacagcg tgaagggccg gtttacaatc tccgccgata cctctaagaa cacagcctat     240
ctgcagatga attccctgag gcagaggac accgccgtgt actattgtgc cagacacggc     300
tacgccctgg attattgggg ccagggcacc ctggtgacag tgtctagc               348

<210> SEQ ID NO 63
<211> LENGTH: 244
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 3625 scFv (VL-VH)

<400> SEQUENCE: 63

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Ala
            20                  25                  30

Val Ala Trp Tyr Gln Gln Lys Pro Gly Lys Ala Pro Lys Leu Leu Ile
        35                  40                  45

Tyr Ser Ala Ser Ser Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Val Trp Val Gly Tyr
                85                  90                  95

Ser Leu Ile Thr Phe Gly Gln Gly Thr Lys Val Glu Ile Lys Gly Ser
            100                 105                 110

Thr Ser Gly Ser Gly Lys Pro Gly Ser Gly Glu Gly Ser Thr Lys Gly
            115                 120                 125

Glu Val Gln Leu Val Glu Ser Gly Gly Gly Leu Val Gln Pro Gly Gly
130                 135                 140

Ser Leu Arg Leu Ser Cys Ala Ala Ser Gly Phe Asn Ile Tyr Tyr Ser
145                 150                 155                 160

Tyr Met His Trp Val Arg Gln Ala Pro Gly Lys Gly Leu Glu Trp Val
                165                 170                 175

Ala Ser Ile Ser Pro Tyr Tyr Gly Tyr Thr Ser Tyr Ala Asp Ser Val
            180                 185                 190

Lys Gly Arg Phe Thr Ile Ser Ala Asp Thr Ser Lys Asn Thr Ala Tyr
        195                 200                 205

Leu Gln Met Asn Ser Leu Arg Ala Glu Asp Thr Ala Val Tyr Tyr Cys
    210                 215                 220

Ala Arg His Gly Tyr Ala Leu Asp Tyr Trp Gly Gln Gly Thr Leu Val
225                 230                 235                 240

Thr Val Ser Ser

<210> SEQ ID NO 64
<211> LENGTH: 732
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: 3625 scFv (VL-VH)

<400> SEQUENCE: 64
gacatccaga tgacacagtc cccatccagc ctcagcgctt ccgtgggaga cagagtgacc      60
atcacatgca ggcaagcca gtccgtgtct agcgccgtgg catggtacca gcagaagccc     120
ggcaaggccc ctaagctgct gatctacagc gcctcctctc tgtattccgg cgtgccatct    180
cggttctctg gcagcagatc cggcaccgac tttaccctga caatcagctc cctgcagccc    240
gaggatttcg ccacatacta ttgccagcag agcgtgtggg tgggctactc cctgatcacc    300
tttggccagg gcacaaaagt cgaaattaag ggatctacca gcggatccgg caagcctggc    360
agcggagagg gatccacaaa gggagaggtg cagctcgtgg aaagcggcgg agggctggtc    420
cagccaggcg gctctctgag gctgagctgt gcagcatccg gcttcaacat ctactatagc    480

```
tacatgcatt gggtccgcca ggctcctggc aaaggactgg aatgggtggc ctctatcagc    540
ccttactatg ctacacctc ttatgccgac agcgtgaagg ccggtttac aatctccgcc      600 gataccctcta agaacacagc ctatctgcag atgaattccc tgagggcaga ggacaccgcc   660
gtgtactatt gtgccagaca cggctacgcc ctggattatt ggggccaggg cacccctggtg  720 acagtgtcta gc                                                        732
```

<210> SEQ ID NO 65
<211> LENGTH: 244
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 3625 scFv (VH-VL)

<400> SEQUENCE: 65

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Tyr Tyr Ser
            20                  25                  30

Tyr Met His Trp Val Arg Gln Ala Pro Gly Lys Gly Leu Glu Trp Val
        35                  40                  45

Ala Ser Ile Ser Pro Tyr Tyr Gly Tyr Thr Ser Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg His Gly Tyr Ala Leu Asp Tyr Trp Gly Gln Gly Thr Leu Val
            100                 105                 110

Thr Val Ser Ser Gly Ser Thr Ser Gly Ser Gly Lys Pro Gly Ser Gly
        115                 120                 125

Glu Gly Ser Thr Lys Gly Asp Ile Gln Met Thr Gln Ser Pro Ser Ser
    130                 135                 140

Leu Ser Ala Ser Val Gly Asp Arg Val Thr Ile Thr Cys Arg Ala Ser
145                 150                 155                 160

Gln Ser Val Ser Ser Ala Val Ala Trp Tyr Gln Gln Lys Pro Gly Lys
                165                 170                 175

Ala Pro Lys Leu Leu Ile Tyr Ser Ala Ser Ser Leu Tyr Ser Gly Val
            180                 185                 190

Pro Ser Arg Phe Ser Gly Ser Arg Ser Gly Thr Asp Phe Thr Leu Thr
        195                 200                 205

Ile Ser Ser Leu Gln Pro Glu Asp Phe Ala Thr Tyr Tyr Cys Gln Gln
    210                 215                 220

Ser Val Trp Val Gly Tyr Ser Leu Ile Thr Phe Gly Gln Gly Thr Lys
225                 230                 235                 240

Val Glu Ile Lys
```

<210> SEQ ID NO 66
<211> LENGTH: 732
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:

<223> OTHER INFORMATION: 3625 scFv (VH-VL)

<400> SEQUENCE: 66

```
gaggtgcagc tggtggagtc tggaggaggc ctggtgcagc ctggcggctc cctgaggctg      60
tcttgcgcag caagcggctt caacatctac tatagctaca tgcactgggt gcgccaggcc     120
cctggcaagg gcctggagtg ggtggcctcc atctctccat actatggcta cacctcctat     180
gccgactctg tgaagggccg gtttacaatc agcgccgata cctccaagaa cacagcctat     240
ctgcagatga attccctgag gcagaggac accgccgtgt actattgcgc cagacacggc     300
tacgccctgg attattgggg ccagggcacc ctggtgacag tgagctccgg cagcacatcc     360
ggatctggca agccaggctc tggagaggga agcaccaagg gcgacatcca gatgacacag     420
tccccatcta gcctgagcgc ctccgtgggc gatagggtga ccatcacatg tcgcgcctct     480
cagagcgtgt cctctgccgt ggcatggtac cagcagaagc ccggcaaggc ccctaagctg     540
ctgatctaca gcgccagctc cctgtattcc ggcgtgcctt ctcggttctc cggctctaga     600
agcggcaccg actttaccct gacaatctct agcctgcagc ccgaggattt cgccacatac     660
tattgtcagc agagcgtgtg ggtgggctac tccctgatca cctttggcca gggcacaaag     720
gtggagatca ag                                                        732
```

<210> SEQ ID NO 67
<211> LENGTH: 617
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 1165 TAC (w/o leader sequence)

<400> SEQUENCE: 67

Asp Ile Gln Met Thr Gln Ser Pro Ser Leu Ser Ala Ser Val Gly
1               5                   10                  15

Asp Arg Val Thr Ile Thr Cys Arg Ala Ser Gln Ser Val Ser Ser Ala
            20                  25                  30

Val Ala Trp Tyr Gln Gln Lys Pro Gly Lys Ala Pro Lys Leu Leu Ile
        35                  40                  45

Tyr Ser Ala Ser Ser Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Val Trp Val Gly Tyr
                85                  90                  95

Ser Leu Ile Thr Phe Gly Gln Gly Thr Lys Val Glu Ile Lys Gly Ser
            100                 105                 110

Thr Ser Gly Ser Gly Lys Pro Gly Ser Gly Glu Gly Ser Thr Lys Gly
        115                 120                 125

Glu Val Gln Leu Val Glu Ser Gly Gly Gly Leu Val Gln Pro Gly Gly
    130                 135                 140

Ser Leu Arg Leu Ser Cys Ala Ala Ser Gly Phe Asn Ile Tyr Tyr Ser
145                 150                 155                 160

Tyr Met His Trp Val Arg Gln Ala Pro Gly Lys Gly Leu Glu Trp Val
                165                 170                 175

Ala Ser Ile Ser Pro Tyr Tyr Gly Tyr Thr Ser Tyr Ala Asp Ser Val
            180                 185                 190
```

```
Lys Gly Arg Phe Thr Ile Ser Ala Asp Thr Ser Lys Asn Thr Ala Tyr
                195                 200                 205
Leu Gln Met Asn Ser Leu Arg Ala Glu Asp Thr Ala Val Tyr Tyr Cys
        210                 215                 220
Ala Arg His Gly Tyr Ala Leu Asp Tyr Trp Gly Gln Gly Thr Leu Val
225                 230                 235                 240
Thr Val Ser Ser Glu Gln Lys Leu Ile Ser Glu Glu Asp Leu Asn Pro
                245                 250                 255
Gly Gly Gly Gly Ser Gly Gly Gly Ser Gly Gly Gly Ser
                260                 265                 270
Gly Gly Gly Gly Ser Gly Ser Met Asp Ile Gln Met Thr Gln Ser Pro
        275                 280                 285
Ser Ser Leu Ser Ala Ser Val Gly Asp Arg Val Thr Ile Thr Cys Arg
        290                 295                 300
Ala Ser Gln Asp Ile Arg Asn Tyr Leu Asn Trp Tyr Gln Gln Lys Pro
305                 310                 315                 320
Gly Lys Ala Pro Lys Leu Leu Ile Tyr Tyr Thr Ser Arg Leu Glu Ser
                325                 330                 335
Gly Val Pro Ser Arg Phe Ser Gly Ser Gly Ser Gly Thr Asp Tyr Thr
                340                 345                 350
Leu Thr Ile Ser Ser Leu Gln Pro Glu Asp Phe Ala Thr Tyr Tyr Cys
        355                 360                 365
Gln Gln Gly Asn Thr Leu Pro Trp Thr Phe Gly Gln Gly Thr Lys Val
        370                 375                 380
Glu Ile Lys Gly Gly Gly Gly Ser Gly Gly Gly Gly Ser Gly Gly Gly
385                 390                 395                 400
Gly Ser Glu Val Gln Leu Val Glu Ser Gly Gly Gly Leu Val Gln Pro
                405                 410                 415
Gly Gly Ser Leu Arg Leu Ser Cys Ala Ala Ser Gly Tyr Ser Phe Thr
                420                 425                 430
Gly Tyr Thr Met Asn Trp Val Arg Gln Ala Pro Gly Lys Gly Leu Glu
        435                 440                 445
Trp Val Ala Leu Ile Asn Pro Thr Lys Gly Val Ser Thr Tyr Asn Gln
450                 455                 460
Lys Phe Lys Asp Arg Phe Thr Ile Ser Val Asp Lys Ser Lys Asn Thr
465                 470                 475                 480
Ala Tyr Leu Gln Met Asn Ser Leu Arg Ala Glu Asp Thr Ala Val Tyr
                485                 490                 495
Tyr Cys Ala Arg Ser Gly Tyr Tyr Gly Asp Ser Asp Trp Tyr Phe Asp
                500                 505                 510
Val Trp Gly Gln Gly Thr Leu Val Thr Val Ser Ser Thr Ser Gly Gly
        515                 520                 525
Gly Gly Ser Leu Glu Ser Gly Gln Val Leu Leu Glu Ser Asn Ile Lys
        530                 535                 540
Val Leu Pro Thr Trp Ser Thr Pro Val Gln Pro Met Ala Leu Ile Val
545                 550                 555                 560
Leu Gly Gly Val Ala Gly Leu Leu Leu Phe Ile Gly Leu Gly Ile Phe
                565                 570                 575
Phe Cys Val Arg Cys Arg His Arg Arg Arg Gln Ala Glu Arg Met Ser
                580                 585                 590
Gln Ile Lys Arg Leu Leu Ser Glu Lys Lys Thr Cys Gln Cys Pro His
        595                 600                 605
Arg Phe Gln Lys Thr Cys Ser Pro Ile
```

<210> SEQ ID NO 68
<211> LENGTH: 1854
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: 1165 TAC (w/o leader sequence)

<400> SEQUENCE: 68

```
gacatccaga tgacacagtc cccatccagc ctcagcgctt ccgtgggaga cagagtgacc      60
atcacatgca gggcaagcca gtccgtgtct agcgccgtgg catggtacca gcagaagccc     120
ggcaaggccc ctaagctgct gatctacagc gcctcctctc tgtattccgg cgtgccatct     180
cggttctctg gcagcagatc cggcaccgac tttaccctga caatcagctc cctgcagccc     240
gaggatttcg ccacatacta ttgccagcag agcgtgtggg tgggctactc cctgatcacc     300
tttggccagg gcacaaaagt cgaaattaag ggatctacca gcggatccgg caagcctggc     360
agcggagagg gatccacaaa gggagaggtg cagctcgtgg aaagcggcgg agggctggtc     420
cagccaggcg gctctctgag gctgagctgt gcagcatccg gcttcaacat ctactatagc     480
tacatgcatt gggtccgcca ggctcctggc aaaggactgg aatgggtggc ctctatcagc     540
ccttactatg gctacaccct ttatgccgac agcgtgaagg gccggtttac aatctccgcc     600
gatacctcta gaacacagc ctatctgcag atgaattccc tgagggcaga ggacaccgcc     660
gtgtactatt gtgccagaca cggctacgcc ctggattatt ggggccaggg caccctggtg     720
acagtgtcta gcgagcagaa gctgatcagc gaggaggacc tgaatcccgg ggaggagga     780
gggagcgggg gaggaggcag cggcggggga ggctctggag gaggagggag cggatccatg     840
gatatccaga tgacccagtc cccgagctcc ctgtccgcct ctgtgggcga tagggtcacc     900
atcacctgcc gtgccagtca ggacatccgt aattatctga actggtatca acagaaacca     960
ggaaaagctc cgaaactact gatttactat acctcccgcc tggagtctgg agtcccttct    1020
cgcttctctg gttctggttc tgggacggat tacactctga ccatcagcag tctgcaaccg    1080
gaagacttcg caacttatta ctgtcagcaa ggtaatactc tgccgtggac gttcggacag    1140
ggcaccaagg tggagatcaa aggcggcggc ggaagtggag gaggaggctc aggcggagga    1200
gggagcgagg ttcagctggt ggagtctggc ggtggcctgg tgcagccagg ggctcactc    1260
cgtttgtcct gtgcagcttc tggctactcc tttaccggct acactatgaa ctgggtgcgt    1320
caggccccag gtaagggcct ggaatgggtt gcactgatta atcctaccaa aggtgttagt    1380
acctacaacc agaagttcaa ggaccgtttc actataagcg tagataaatc caaaacaca    1440
gcctacctgc aaatgaacag cctgcgtgct gaggacactg ccgtctatta ttgtgctaga    1500
agcggatact acggcgatag tgactggtat tttgacgtgt ggggtcaagg aaccctggtc    1560
accgtctcct cgactagtgg cggaggagga tcactcgaga gcggacaggt gctgctggaa    1620
tccaatatca aagtcctgcc cacttggtct acccccgtgc agcctatggc tctgattgtg    1680
ctgggaggag tcgcaggact gctgctgttt atcgggctgg gaattttctt ttgcgtgcgc    1740
tgccggcacc ggagaaggca ggccgagcgc atgagccaga tcaagcgact gctgagcgag    1800
aagaaaacct gtcagtgtcc ccatagattc agaagacct gttcacccat ttga          1854
```

<210> SEQ ID NO 69

<211> LENGTH: 638
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: 1165 TAC (w/ leader sequence)

<400> SEQUENCE: 69

```
Met Ala Leu Pro Val Thr Ala Leu Leu Pro Leu Ala Leu Leu Leu
1               5                   10                  15

His Ala Ala Arg Pro Asp Ile Gln Met Thr Gln Ser Pro Ser Ser Leu
            20                  25                  30

Ser Ala Ser Val Gly Asp Arg Val Thr Ile Thr Cys Arg Ala Ser Gln
        35                  40                  45

Ser Val Ser Ser Ala Val Ala Trp Tyr Gln Gln Lys Pro Gly Lys Ala
50                  55                  60

Pro Lys Leu Leu Ile Tyr Ser Ala Ser Ser Leu Tyr Ser Gly Val Pro
65                  70                  75                  80

Ser Arg Phe Ser Gly Ser Arg Ser Gly Thr Asp Phe Thr Leu Thr Ile
                85                  90                  95

Ser Ser Leu Gln Pro Glu Asp Phe Ala Thr Tyr Tyr Cys Gln Gln Ser
            100                 105                 110

Val Trp Val Gly Tyr Ser Leu Ile Thr Phe Gly Gln Gly Thr Lys Val
        115                 120                 125

Glu Ile Lys Gly Ser Thr Ser Gly Ser Gly Lys Pro Gly Ser Gly Glu
    130                 135                 140

Gly Ser Thr Lys Gly Glu Val Gln Leu Val Glu Ser Gly Gly Gly Leu
145                 150                 155                 160

Val Gln Pro Gly Gly Ser Leu Arg Leu Ser Cys Ala Ala Ser Gly Phe
                165                 170                 175

Asn Ile Tyr Tyr Ser Tyr Met His Trp Val Arg Gln Ala Pro Gly Lys
            180                 185                 190

Gly Leu Glu Trp Val Ala Ser Ile Ser Pro Tyr Tyr Gly Tyr Thr Ser
        195                 200                 205

Tyr Ala Asp Ser Val Lys Gly Arg Phe Thr Ile Ser Ala Asp Thr Ser
    210                 215                 220

Lys Asn Thr Ala Tyr Leu Gln Met Asn Ser Leu Arg Ala Glu Asp Thr
225                 230                 235                 240

Ala Val Tyr Tyr Cys Ala Arg His Gly Tyr Ala Leu Asp Tyr Trp Gly
                245                 250                 255

Gln Gly Thr Leu Val Thr Val Ser Ser Glu Gln Lys Leu Ile Ser Glu
            260                 265                 270

Glu Asp Leu Asn Pro Gly Gly Gly Gly Ser Gly Gly Gly Gly Ser
        275                 280                 285

Gly Gly Gly Gly Ser Gly Gly Gly Ser Gly Ser Met Asp Ile Gln
    290                 295                 300

Met Thr Gln Ser Pro Ser Ser Leu Ser Ala Ser Val Gly Asp Arg Val
305                 310                 315                 320

Thr Ile Thr Cys Arg Ala Ser Gln Asp Ile Arg Asn Tyr Leu Asn Trp
                325                 330                 335

Tyr Gln Gln Lys Pro Gly Lys Ala Pro Lys Leu Leu Ile Tyr Tyr Thr
            340                 345                 350

Ser Arg Leu Glu Ser Gly Val Pro Ser Arg Phe Ser Gly Ser Gly Ser
        355                 360                 365
```

Gly Thr Asp Tyr Thr Leu Thr Ile Ser Ser Leu Gln Pro Glu Asp Phe
    370                 375                 380

Ala Thr Tyr Tyr Cys Gln Gln Gly Asn Thr Leu Pro Trp Thr Phe Gly
385                 390                 395                 400

Gln Gly Thr Lys Val Glu Ile Lys Gly Gly Gly Ser Gly Gly Gly
            405                 410                 415

Gly Ser Gly Gly Gly Gly Ser Glu Val Gln Leu Val Glu Ser Gly Gly
            420                 425                 430

Gly Leu Val Gln Pro Gly Gly Ser Leu Arg Leu Ser Cys Ala Ala Ser
            435                 440                 445

Gly Tyr Ser Phe Thr Gly Tyr Thr Met Asn Trp Val Arg Gln Ala Pro
            450                 455                 460

Gly Lys Gly Leu Glu Trp Val Ala Leu Ile Asn Pro Thr Lys Gly Val
465                 470                 475                 480

Ser Thr Tyr Asn Gln Lys Phe Lys Asp Arg Phe Thr Ile Ser Val Asp
                485                 490                 495

Lys Ser Lys Asn Thr Ala Tyr Leu Gln Met Asn Ser Leu Arg Ala Glu
            500                 505                 510

Asp Thr Ala Val Tyr Tyr Cys Ala Arg Ser Gly Tyr Tyr Gly Asp Ser
            515                 520                 525

Asp Trp Tyr Phe Asp Val Trp Gly Gln Gly Thr Leu Val Thr Val Ser
530                 535                 540

Ser Thr Ser Gly Gly Gly Gly Ser Leu Glu Ser Gly Gln Val Leu Leu
545                 550                 555                 560

Glu Ser Asn Ile Lys Val Leu Pro Thr Trp Ser Thr Pro Val Gln Pro
            565                 570                 575

Met Ala Leu Ile Val Leu Gly Gly Val Ala Gly Leu Leu Leu Phe Ile
            580                 585                 590

Gly Leu Gly Ile Phe Phe Cys Val Arg Cys Arg His Arg Arg Arg Gln
            595                 600                 605

Ala Glu Arg Met Ser Gln Ile Lys Arg Leu Leu Ser Glu Lys Lys Thr
            610                 615                 620

Cys Gln Cys Pro His Arg Phe Gln Lys Thr Cys Ser Pro Ile
625                 630                 635

<210> SEQ ID NO 70
<211> LENGTH: 1917
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: 1165 TAC (w/ leader sequence)

<400> SEQUENCE: 70
atggccctgc cagtgaccgc cctgctgctg ccactggccc tgctgctgca cgccgcccgg     60
cctgacatcc agatgacaca gtccccatcc agcctcagcg cttccgtggg agacagagtg    120
accatcacat gcagggcaag ccagtccgtg tctagcgccg tggcatggta ccagcagaag    180
cccggcaagg cccctaagct gctgatctac agcgcctcct ctctgtattc cggcgtgcca    240
tctcggttct ctggcagcag atccggcacc gactttaccc tgacaatcag ctccctgcag    300
cccgaggatt tcgccacata ctattgccag cagagcgtgt gggtgggcta ctccctgatc    360
acctttggcc agggcacaaa agtcgaaatt aagggatcta ccagcggatc cggcaagcct    420

-continued

```
ggcagcggag agggatccac aaagggagag gtgcagctcg tggaaagcgg cggagggctg    480
gtccagccag gcggctctct gaggctgagc tgtgcagcat ccggcttcaa catctactat    540
agctacatgc attgggtccg ccaggctcct ggcaaaggac tggaatgggt ggcctctatc    600
agcccttact atggctacac ctcttatgcc gacagcgtga aggccggtt tacaatctcc     660 gccgatacct ctaagaacac agcctatctg cagatgaatt ccctgagggc agaggacacc    720
gccgtgtact attgtgccag acacggctac gccctggatt attggggcca gggcaccctg    780
gtgacagtgt ctagcgagca aagctgatc agcgaggagg acctgaatcc cggggagga     840 ggagggagcg ggggaggagg cagcggcggg ggaggctctg gaggaggagg gagcggatcc    900
atggatatcc agatgaccca gtccccgagc tccctgtccg cctctgtggg cgatagggtc    960
accatcacct gccgtgccag tcaggacatc cgtaattatc tgaactggta tcaacagaaa    1020
ccaggaaaag ctccgaaact actgatttac tatacctccc gcctggagtc tggagtccct    1080
tctcgcttct ctggttctgg ttctgggacg gattacactc tgaccatcag cagtctgcaa    1140
ccggaagact tcgcaactta ttactgtcag caaggtaata tctgccgtg acgttcgga     1200 cagggcacca aggtggagat caaaggcggc ggcggaagtg gaggaggagg ctcaggcgga    1260
ggagggagcg aggttcagct ggtggagtct ggcggtggcc tggtgcagcc aggggggctca   1320 ctccgtttgt cctgtgcagc ttctggctac tcctttaccg gctacactat gaactgggtg    1380
cgtcaggccc caggtaaggg cctggaatgg gttgcactga ttaatcctac caaaggtgtt    1440
agtacctaca accagaagtt caaggaccgt ttcactataa gcgtagataa atccaaaaac    1500
acagcctacc tgcaaatgaa cagcctgcgt gctgaggaca ctgccgtcta ttattgtgct    1560
agaagcggat actacggcga tagtgactgg tattttgacg tgtggggtca aggaaccctg    1620
gtcaccgtct cctcgactag tggcggagga ggatcactcg agagcggaca ggtgctgctg    1680
gaatccaata tcaaagtcct gcccacttgg tctacccccg tgcagcctat ggctctgatt    1740
gtgctgggag gagtcgcagg actgctgctg tttatcgggc tgggaatttt cttttgcgtg    1800
cgctgccggc accggagaag gcaggccgag cgcatgagcc agatcaagcg actgctgagc    1860
gagaagaaaa cctgtcagtg tccccataga ttccagaaga cctgttcacc catttga       1917
```

<210> SEQ ID NO 71
<211> LENGTH: 617
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: 1162 TAC (w/o leader sequence)

<400> SEQUENCE: 71

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Tyr Tyr Ser
            20                  25                  30

Tyr Met His Trp Val Arg Gln Ala Pro Gly Lys Gly Leu Glu Trp Val
        35                  40                  45

Ala Ser Ile Ser Pro Tyr Tyr Gly Tyr Thr Ser Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
```

-continued

```
                 85                  90                  95
Ala Arg His Gly Tyr Ala Leu Asp Tyr Trp Gly Gln Gly Thr Leu Val
            100                 105                 110
Thr Val Ser Ser Gly Ser Thr Ser Gly Ser Gly Lys Pro Gly Ser Gly
            115                 120                 125
Glu Gly Ser Thr Lys Gly Asp Ile Gln Met Thr Gln Ser Pro Ser Ser
        130                 135                 140
Leu Ser Ala Ser Val Gly Asp Arg Val Thr Ile Thr Cys Arg Ala Ser
145                 150                 155                 160
Gln Ser Val Ser Ala Val Ala Trp Tyr Gln Gln Lys Pro Gly Lys
                165                 170                 175
Ala Pro Lys Leu Leu Ile Tyr Ser Ala Ser Ser Leu Tyr Ser Gly Val
                180                 185                 190
Pro Ser Arg Phe Ser Gly Ser Arg Ser Gly Thr Asp Phe Thr Leu Thr
            195                 200                 205
Ile Ser Ser Leu Gln Pro Glu Asp Phe Ala Thr Tyr Tyr Cys Gln Gln
        210                 215                 220
Ser Val Trp Val Gly Tyr Ser Leu Ile Thr Phe Gly Gln Gly Thr Lys
225                 230                 235                 240
Val Glu Ile Lys Glu Gln Lys Leu Ile Ser Glu Asp Leu Asn Pro
                245                 250                 255
Gly Gly Gly Gly Ser Gly Gly Gly Ser Gly Gly Gly Ser
                260                 265                 270
Gly Gly Gly Gly Ser Gly Ser Met Asp Ile Gln Met Thr Gln Ser Pro
            275                 280                 285
Ser Ser Leu Ser Ala Ser Val Gly Asp Arg Val Thr Ile Thr Cys Arg
        290                 295                 300
Ala Ser Gln Asp Ile Arg Asn Tyr Leu Asn Trp Tyr Gln Gln Lys Pro
305                 310                 315                 320
Gly Lys Ala Pro Lys Leu Leu Ile Tyr Tyr Thr Ser Arg Leu Glu Ser
                325                 330                 335
Gly Val Pro Ser Arg Phe Ser Gly Ser Gly Ser Gly Thr Asp Tyr Thr
                340                 345                 350
Leu Thr Ile Ser Ser Leu Gln Pro Glu Asp Phe Ala Thr Tyr Tyr Cys
            355                 360                 365
Gln Gln Gly Asn Thr Leu Pro Trp Thr Phe Gly Gln Gly Thr Lys Val
        370                 375                 380
Glu Ile Lys Gly Gly Gly Gly Ser Gly Gly Gly Gly Ser Gly Gly Gly
385                 390                 395                 400
Gly Ser Glu Val Gln Leu Val Glu Ser Gly Gly Gly Leu Val Gln Pro
                405                 410                 415
Gly Gly Ser Leu Arg Leu Ser Cys Ala Ala Ser Gly Tyr Ser Phe Thr
                420                 425                 430
Gly Tyr Thr Met Asn Trp Val Arg Gln Ala Pro Gly Lys Gly Leu Glu
            435                 440                 445
Trp Val Ala Leu Ile Asn Pro Thr Lys Gly Val Ser Thr Tyr Asn Gln
        450                 455                 460
Lys Phe Lys Asp Arg Phe Thr Ile Ser Val Asp Lys Ser Lys Asn Thr
465                 470                 475                 480
Ala Tyr Leu Gln Met Asn Ser Leu Arg Ala Glu Asp Thr Ala Val Tyr
                485                 490                 495
Tyr Cys Ala Arg Ser Gly Tyr Tyr Gly Asp Ser Asp Trp Tyr Phe Asp
                500                 505                 510
```

Val Trp Gly Gln Gly Thr Leu Val Thr Val Ser Ser Thr Gly Gly
    515                 520                 525

Gly Gly Ser Leu Glu Ser Gly Gln Val Leu Leu Glu Ser Asn Ile Lys
    530                 535                 540

Val Leu Pro Thr Trp Ser Thr Pro Val Gln Pro Met Ala Leu Ile Val
545                 550                 555                 560

Leu Gly Gly Val Ala Gly Leu Leu Leu Phe Ile Gly Leu Gly Ile Phe
                565                 570                 575

Phe Cys Val Arg Cys Arg His Arg Arg Gln Ala Glu Arg Met Ser
                580                 585                 590

Gln Ile Lys Arg Leu Leu Ser Glu Lys Lys Thr Cys Gln Cys Pro His
    595                 600                 605

Arg Phe Gln Lys Thr Cys Ser Pro Ile
    610                 615

<210> SEQ ID NO 72
<211> LENGTH: 1854
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: 1162 TAC (w/o leader sequence)

<400> SEQUENCE: 72
gaggtgcagc tcgtggaaag cggcggaggg ctggtccagc caggcggctc cctgaggctg      60
tcttgcgcag caagcggctt caacatctac tatagctaca tgcattgggt ccgccaggct     120
cctggcaaag gactggaatg ggtggcctcc atctctccat actatggcta cacctcctat     180
gccgactctg tgaagggccg gtttacaatc agcgccgata cctccaagaa cacagcctat     240
ctgcagatga attccctgag ggcagaggac accgccgtgt actattgcgc agacacggc      300 tacgccctgg attattgggg ccagggcacc ctggtgacag tgagctccgg cagcacatcc     360
ggatctggca agccaggctc tggagaggga agcaccaagg gcgacatcca gatgacacag     420
tccccatcta gcctgagcgc ctccgtggga gacagagtga ccatcacatg tcgcgcctct     480
cagagcgtgt cctctgccgt ggcatggtac cagcagaagc ccggcaaggc ccctaagctg     540
ctgatctaca cgccagctc cctgtattcc ggcgtgcctt ctcggttctc cggctctaga     600
agcggcaccg actttaccct gacaatctct agcctgcagc ccgaggattt cgccacatac     660
tattgtcagc agagcgtgtg ggtgggctac tccctgatca cctttggcca gggcacaaaa     720
gtcgaaatta aggagcagaa gctgatcagc gaggaggacc tgaatcccgg gggaggagga     780
gggagcgggg gaggaggcag cggcggggga ggctctggag gaggagggag cggatccatg     840
gatatccaga tgacccagtc cccgagctcc ctgtccgcct ctgtgggcga tagggtcacc     900
atcacctgcc gtgccagtca ggacatccgt aattatctga actggtatca acagaaacca     960
ggaaaagctc cgaaactact gatttactat acctcccgcc tggagtctgg agtcccttct    1020
cgcttctctg gttctggttc tgggacggat tacactctga ccatcagcag tctgcaaccg    1080
gaagacttcg caacttatta ctgtcagcaa ggtaatactc tgccgtggac gttcggacag    1140
ggcaccaagg tggagatcaa aggcggcggc ggaagtggag gaggaggctc aggcggagga    1200
gggagcgagg ttcagctggt ggagtctggc ggtggcctgg tgcagccagg ggctcactc    1260 cgtttgtcct gtgcagcttc tggctactcc tttaccggct acactatgaa ctgggtgcgt    1320

```
caggccccag gtaagggcct ggaatgggtt gcactgatta atcctaccaa aggtgttagt    1380
acctacaacc agaagttcaa ggaccgtttc actataagcg tagataaatc caaaaacaca    1440
gcctacctgc aaatgaacag cctgcgtgct gaggacactg ccgtctatta ttgtgctaga    1500
agcggatact acggcgatag tgactggtat tttgacgtgt ggggtcaagg aaccctggtc    1560
accgtctcct cgactagtgg cggaggagga tcactcgaga gcggacaggt gctgctggaa    1620
tccaatatca aagtcctgcc cacttggtct accccgtgc agcctatggc tctgattgtg     1680
ctgggaggag tcgcaggact gctgctgttt atcgggctgg gaattttctt ttgcgtgcgc    1740
tgccggcacc ggagaaggca ggccgagcgc atgagccaga tcaagcgact gctgagcgag    1800
aagaaaacct gtcagtgtcc ccatagattc cagaagacct gttcacccat ttga          1854
```

<210> SEQ ID NO 73
<211> LENGTH: 638
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 1162 TAC (w/ leader sequence)

<400> SEQUENCE: 73

```
Met Ala Leu Pro Val Thr Ala Leu Leu Leu Pro Leu Ala Leu Leu Leu
1               5                   10                  15

His Ala Ala Arg Pro Glu Val Gln Leu Val Glu Ser Gly Gly Gly Leu
            20                  25                  30

Val Gln Pro Gly Gly Ser Leu Arg Leu Ser Cys Ala Ala Ser Gly Phe
        35                  40                  45

Asn Ile Tyr Tyr Ser Tyr Met His Trp Val Arg Gln Ala Pro Gly Lys
    50                  55                  60

Gly Leu Glu Trp Val Ala Ser Ile Ser Pro Tyr Tyr Gly Tyr Thr Ser
65                  70                  75                  80

Tyr Ala Asp Ser Val Lys Gly Arg Phe Thr Ile Ser Ala Asp Thr Ser
                85                  90                  95

Lys Asn Thr Ala Tyr Leu Gln Met Asn Ser Leu Arg Ala Glu Asp Thr
            100                 105                 110

Ala Val Tyr Tyr Cys Ala Arg His Gly Tyr Ala Leu Asp Tyr Trp Gly
        115                 120                 125

Gln Gly Thr Leu Val Thr Val Ser Ser Gly Ser Thr Ser Gly Ser Gly
    130                 135                 140

Lys Pro Gly Ser Gly Glu Gly Ser Thr Lys Gly Asp Ile Gln Met Thr
145                 150                 155                 160

Gln Ser Pro Ser Ser Leu Ser Ala Ser Val Gly Asp Arg Val Thr Ile
                165                 170                 175

Thr Cys Arg Ala Ser Gln Ser Val Ser Ser Ala Val Ala Trp Tyr Gln
            180                 185                 190

Gln Lys Pro Gly Lys Ala Pro Lys Leu Leu Ile Tyr Ser Ala Ser Ser
        195                 200                 205

Leu Tyr Ser Gly Val Pro Ser Arg Phe Ser Gly Ser Arg Ser Gly Thr
    210                 215                 220

Asp Phe Thr Leu Thr Ile Ser Ser Leu Gln Pro Glu Asp Phe Ala Thr
225                 230                 235                 240

Tyr Tyr Cys Gln Gln Ser Val Trp Val Gly Tyr Ser Leu Ile Thr Phe
                245                 250                 255
```

Gly Gln Gly Thr Lys Val Glu Ile Lys Glu Gln Lys Leu Ile Ser Glu
                260                 265                 270

Glu Asp Leu Asn Pro Gly Gly Gly Gly Ser Gly Gly Gly Gly Ser
            275                 280                 285

Gly Gly Gly Gly Ser Gly Gly Gly Ser Gly Ser Met Asp Ile Gln
        290                 295                 300

Met Thr Gln Ser Pro Ser Ser Leu Ser Ala Ser Val Gly Asp Arg Val
305                 310                 315                 320

Thr Ile Thr Cys Arg Ala Ser Gln Asp Ile Arg Asn Tyr Leu Asn Trp
                325                 330                 335

Tyr Gln Gln Lys Pro Gly Lys Ala Pro Lys Leu Leu Ile Tyr Tyr Thr
            340                 345                 350

Ser Arg Leu Glu Ser Gly Val Pro Ser Arg Phe Ser Gly Ser Gly Ser
        355                 360                 365

Gly Thr Asp Tyr Thr Leu Thr Ile Ser Ser Leu Gln Pro Glu Asp Phe
    370                 375                 380

Ala Thr Tyr Tyr Cys Gln Gln Gly Asn Thr Leu Pro Trp Thr Phe Gly
385                 390                 395                 400

Gln Gly Thr Lys Val Glu Ile Lys Gly Gly Gly Gly Ser Gly Gly Gly
                405                 410                 415

Gly Ser Gly Gly Gly Gly Ser Glu Val Gln Leu Val Glu Ser Gly Gly
            420                 425                 430

Gly Leu Val Gln Pro Gly Gly Ser Leu Arg Leu Ser Cys Ala Ala Ser
        435                 440                 445

Gly Tyr Ser Phe Thr Gly Tyr Thr Met Asn Trp Val Arg Gln Ala Pro
    450                 455                 460

Gly Lys Gly Leu Glu Trp Val Ala Leu Ile Asn Pro Thr Lys Gly Val
465                 470                 475                 480

Ser Thr Tyr Asn Gln Lys Phe Lys Asp Arg Phe Thr Ile Ser Val Asp
                485                 490                 495

Lys Ser Lys Asn Thr Ala Tyr Leu Gln Met Asn Ser Leu Arg Ala Glu
            500                 505                 510

Asp Thr Ala Val Tyr Tyr Cys Ala Arg Ser Gly Tyr Tyr Gly Asp Ser
        515                 520                 525

Asp Trp Tyr Phe Asp Val Trp Gly Gln Gly Thr Leu Val Thr Val Ser
    530                 535                 540

Ser Thr Ser Gly Gly Gly Gly Ser Leu Glu Ser Gly Gln Val Leu Leu
545                 550                 555                 560

Glu Ser Asn Ile Lys Val Leu Pro Thr Trp Ser Thr Pro Val Gln Pro
                565                 570                 575

Met Ala Leu Ile Val Leu Gly Gly Val Ala Gly Leu Leu Leu Phe Ile
            580                 585                 590

Gly Leu Gly Ile Phe Phe Cys Val Arg Cys Arg His Arg Arg Arg Gln
        595                 600                 605

Ala Glu Arg Met Ser Gln Ile Lys Arg Leu Leu Ser Glu Lys Lys Thr
    610                 615                 620

Cys Gln Cys Pro His Arg Phe Gln Lys Thr Cys Ser Pro Ile
625                 630                 635

<210> SEQ ID NO 74
<211> LENGTH: 1917
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: 1162 TAC (w/ leader sequence)

<400> SEQUENCE: 74

| | | | | | |
|---|---|---|---|---|---|
| atggccctgc | cagtgaccgc | cctgctgctg | ccactggccc | tgctgctgca | cgccgccaga | 60 |
| cccgaggtgc | agctcgtgga | aagcggcgga | gggctggtcc | agccaggcgg | ctccctgagg | 120 |
| ctgtcttgcg | cagcaagcgg | cttcaacatc | tactatagct | acatgcattg | ggtccgccag | 180 |
| gctcctggca | aaggactgga | atgggtggcc | tccatctctc | catactatgg | ctacacctcc | 240 |
| tatgccgact | ctgtgaaggg | ccggtttaca | atcagcgccg | ataccctcca | agaacacagcc | 300 |
| tatctgcaga | tgaattccct | gagggcagag | gacaccgccg | tgtactattg | cgccagacac | 360 |
| ggctacgccc | tggattattg | gggccagggc | accctggtga | cagtgagctc | cggcagcaca | 420 |
| tccggatctg | gcaagccagg | ctctggagag | ggaagcacca | agggcgacat | ccagatgaca | 480 |
| cagtccccat | ctagcctgag | cgcctccgtg | ggagacagag | tgaccatcac | atgtcgcgcc | 540 |
| tctcagagcg | tgtcctctgc | cgtggcatgg | taccagcaga | agcccggcaa | ggcccctaag | 600 |
| ctgctgatct | acagcgccag | ctccctgtat | ccggcgtgc | cttctcggtt | ctccggctct | 660 |
| agaagcggca | ccgactttac | cctgacaatc | tctagcctgc | agcccgagga | tttcgccaca | 720 |
| tactattgtc | agcagagcgt | gtgggtgggc | tactccctga | tcacctttgg | ccagggcaca | 780 |
| aaagtcgaaa | ttaaggagca | gaagctgatc | agcgaggagg | acctgaatcc | cggggaggga | 840 |
| ggagggagcg | ggggaggagg | cagcggcggg | ggaggctctg | gaggaggagg | gagcggatcc | 900 |
| atggatatcc | agatgaccca | gtcccccagc | tccctgtccg | cctctgtggg | cgataggtc | 960 |
| accatcacct | gccgtgccag | tcaggacatc | cgtaattatc | tgaactggta | tcaacagaaa | 1020 |
| ccaggaaaag | ctccgaaact | actgatttac | tatacctccc | gcctggagtc | tggagtccct | 1080 |
| tctcgcttct | ctggttctgg | ttctgggacg | gattacactc | tgaccatcag | cagtctgcaa | 1140 |
| ccggaagact | tcgcaactta | ttactgtcag | caaggtaata | tctgccgtg | gacgttcgga | 1200 |
| cagggcacca | aggtggagat | caaaggcggc | ggcggaagtg | gaggaggagg | ctcaggcgga | 1260 |
| ggagggagcg | aggttcagct | ggtggagtct | ggcggtggcc | tggtgcagcc | aggggggctca | 1320 |
| ctccgtttgt | cctgtgcagc | ttctggctac | tcctttaccg | gctacactat | gaactgggtg | 1380 |
| cgtcaggccc | caggtaaggg | cctggaatgg | gttgcactga | ttaatcctac | caaaggtgtt | 1440 |
| agtacctaca | accagaagtt | caaggaccgt | ttcactataa | gcgtagataa | atccaaaaac | 1500 |
| acagcctacc | tgcaaatgaa | cagcctgcgt | gctgaggaca | ctgccgtcta | ttattgtgct | 1560 |
| agaagcggat | actacggcga | tagtgactgg | tattttgacg | tgtggggtca | aggaaccctg | 1620 |
| gtcaccgtct | cctcgactag | tggcggagga | ggatcactcg | agagcggaca | ggtgctgctg | 1680 |
| gaatccaata | tcaaagtcct | gcccacttgg | tctaccccg | tgcagcctat | ggctctgatt | 1740 |
| gtgctgggag | gagtcgcagg | actgctgctg | tttatcgggc | tgggaatttt | cttttgcgtg | 1800 |
| cgctgccggc | accggagaag | gcaggccgag | cgcatgagcc | agatcaagcg | actgctgagc | 1860 |
| gagaagaaaa | cctgtcagtg | tccccataga | ttccagaaga | cctgttcacc | catttga | 1917 |

<210> SEQ ID NO 75
<211> LENGTH: 635
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:

<223> OTHER INFORMATION: 1002 TAC (w/ leader Sequence)

<400> SEQUENCE: 75

```
Met Ala Leu Pro Val Thr Ala Leu Leu Leu Pro Leu Ala Leu Leu Leu
1               5                   10                  15

His Ala Ala Arg Pro Asp Ile Gln Met Thr Gln Ser Pro Ser Ser Leu
            20                  25                  30

Ser Ala Ser Val Gly Asp Arg Val Thr Ile Thr Cys Arg Ala Ser Gln
        35                  40                  45

Ser Val Ser Ser Ala Val Ala Trp Tyr Gln Gln Lys Pro Gly Lys Ala
    50                  55                  60

Pro Lys Leu Leu Ile Tyr Ser Ala Ser Ser Leu Tyr Ser Gly Val Pro
65                  70                  75                  80

Ser Arg Phe Ser Gly Ser Arg Ser Gly Thr Asp Phe Thr Leu Thr Ile
                85                  90                  95

Ser Ser Leu Gln Pro Glu Asp Phe Ala Thr Tyr Tyr Cys Gln Gln Ser
            100                 105                 110

Val Trp Val Gly Tyr Ser Leu Ile Thr Phe Gly Gln Gly Thr Lys Val
        115                 120                 125

Glu Ile Lys Gly Ser Thr Ser Gly Ser Gly Lys Pro Gly Ser Gly Glu
    130                 135                 140

Gly Ser Thr Lys Gly Glu Val Gln Leu Val Glu Ser Gly Gly Gly Leu
145                 150                 155                 160

Val Gln Pro Gly Gly Ser Leu Arg Leu Ser Cys Ala Ala Ser Gly Phe
                165                 170                 175

Asn Ile Tyr Tyr Ser Tyr Met His Trp Val Arg Gln Ala Pro Gly Lys
            180                 185                 190

Gly Leu Glu Trp Val Ala Ser Ile Ser Pro Tyr Tyr Gly Tyr Thr Ser
        195                 200                 205

Tyr Ala Asp Ser Val Lys Gly Arg Phe Thr Ile Ser Ala Asp Thr Ser
    210                 215                 220

Lys Asn Thr Ala Tyr Leu Gln Met Asn Ser Leu Arg Ala Glu Asp Thr
225                 230                 235                 240

Ala Val Tyr Tyr Cys Ala Arg His Gly Tyr Ala Leu Asp Tyr Trp Gly
                245                 250                 255

Gln Gly Thr Leu Val Thr Val Ser Ser Glu Gln Lys Leu Ile Ser Glu
            260                 265                 270

Glu Asp Leu Asn Pro Gly Ala Glu Ala Ala Lys Glu Ala Ala Ala
        275                 280                 285

Lys Glu Ala Ala Ala Lys Ala Gly Ser Met Asp Ile Gln Met Thr Gln
    290                 295                 300

Ser Pro Ser Ser Leu Ser Ala Ser Val Gly Asp Arg Val Thr Ile Thr
305                 310                 315                 320

Cys Arg Ala Ser Gln Asp Ile Arg Asn Tyr Leu Asn Trp Tyr Gln Gln
                325                 330                 335

Lys Pro Gly Lys Ala Pro Lys Leu Leu Ile Tyr Tyr Thr Ser Arg Leu
            340                 345                 350

Glu Ser Gly Val Pro Ser Arg Phe Ser Gly Ser Gly Ser Gly Thr Asp
        355                 360                 365

Tyr Thr Leu Thr Ile Ser Ser Leu Gln Pro Glu Asp Phe Ala Thr Tyr
    370                 375                 380

Tyr Cys Gln Gln Gly Asn Thr Leu Pro Trp Thr Phe Gly Gln Gly Thr
385                 390                 395                 400
```

```
Lys Val Glu Ile Lys Gly Gly Gly Gly Ser Gly Gly Gly Gly Ser Gly
                405                 410                 415

Gly Gly Gly Ser Glu Val Gln Leu Val Glu Ser Gly Gly Gly Leu Val
            420                 425                 430

Gln Pro Gly Gly Ser Leu Arg Leu Ser Cys Ala Ala Ser Gly Tyr Ser
        435                 440                 445

Phe Thr Gly Tyr Thr Met Asn Trp Val Arg Gln Ala Pro Gly Lys Gly
    450                 455                 460

Leu Glu Trp Val Ala Leu Ile Asn Pro Tyr Lys Gly Val Ser Thr Tyr
465                 470                 475                 480

Asn Gln Lys Phe Lys Asp Arg Phe Thr Ile Ser Val Asp Lys Ser Lys
                485                 490                 495

Asn Thr Ala Tyr Leu Gln Met Asn Ser Leu Arg Ala Glu Asp Thr Ala
            500                 505                 510

Val Tyr Tyr Cys Ala Arg Ser Gly Tyr Tyr Gly Asp Ser Asp Trp Tyr
        515                 520                 525

Phe Asp Val Trp Gly Gln Gly Thr Leu Val Thr Val Ser Ser Thr Ser
    530                 535                 540

Gly Gly Gly Gly Ser Leu Glu Ser Gly Gln Val Leu Leu Glu Ser Asn
545                 550                 555                 560

Ile Lys Val Leu Pro Thr Trp Ser Thr Pro Val Gln Pro Met Ala Leu
                565                 570                 575

Ile Val Leu Gly Gly Val Ala Gly Leu Leu Leu Phe Ile Gly Leu Gly
            580                 585                 590

Ile Phe Phe Cys Val Arg Cys Arg His Arg Arg Gln Ala Glu Arg
        595                 600                 605

Met Ser Gln Ile Lys Arg Leu Leu Ser Glu Lys Lys Thr Cys Gln Cys
    610                 615                 620

Pro His Arg Phe Gln Lys Thr Cys Ser Pro Ile
625                 630                 635

<210> SEQ ID NO 76
<211> LENGTH: 635
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 1042 TAC (w/ leader Sequence)

<400> SEQUENCE: 76

Met Ala Leu Pro Val Thr Ala Leu Leu Leu Pro Leu Ala Leu Leu Leu
1               5                   10                  15

His Ala Ala Arg Pro Glu Val Gln Leu Val Glu Ser Gly Gly Gly Leu
            20                  25                  30

Val Gln Pro Gly Gly Ser Leu Arg Leu Ser Cys Ala Ala Ser Gly Phe
        35                  40                  45

Asn Ile Tyr Tyr Ser Tyr Met His Trp Val Arg Gln Ala Pro Gly Lys
    50                  55                  60

Gly Leu Glu Trp Val Ala Ser Ile Ser Pro Tyr Tyr Gly Tyr Thr Ser
65                  70                  75                  80

Tyr Ala Asp Ser Val Lys Gly Arg Phe Thr Ile Ser Ala Asp Thr Ser
                85                  90                  95

Lys Asn Thr Ala Tyr Leu Gln Met Asn Ser Leu Arg Ala Glu Asp Thr
            100                 105                 110
```

-continued

Ala Val Tyr Tyr Cys Ala Arg His Gly Tyr Ala Leu Asp Tyr Trp Gly
            115                 120                 125

Gln Gly Thr Leu Val Thr Val Ser Ser Gly Ser Thr Ser Gly Ser Gly
130                 135                 140

Lys Pro Gly Ser Gly Glu Gly Ser Thr Lys Gly Asp Ile Gln Met Thr
145                 150                 155                 160

Gln Ser Pro Ser Ser Leu Ser Ala Ser Val Gly Asp Arg Val Thr Ile
                165                 170                 175

Thr Cys Arg Ala Ser Gln Ser Val Ser Ala Val Ala Trp Tyr Gln
            180                 185                 190

Gln Lys Pro Gly Lys Ala Pro Lys Leu Leu Ile Tyr Ser Ala Ser Ser
            195                 200                 205

Leu Tyr Ser Gly Val Pro Ser Arg Phe Ser Gly Ser Arg Ser Gly Thr
            210                 215                 220

Asp Phe Thr Leu Thr Ile Ser Ser Leu Gln Pro Glu Asp Phe Ala Thr
225                 230                 235                 240

Tyr Tyr Cys Gln Gln Ser Val Trp Val Gly Tyr Ser Leu Ile Thr Phe
                245                 250                 255

Gly Gln Gly Thr Lys Val Glu Ile Lys Glu Gln Lys Leu Ile Ser Glu
            260                 265                 270

Glu Asp Leu Asn Pro Gly Ala Glu Ala Ala Lys Glu Ala Ala Ala
275                 280                 285

Lys Glu Ala Ala Ala Lys Ala Gly Ser Met Asp Ile Gln Met Thr Gln
            290                 295                 300

Ser Pro Ser Ser Leu Ser Ala Ser Val Gly Asp Arg Val Thr Ile Thr
305                 310                 315                 320

Cys Arg Ala Ser Gln Asp Ile Arg Asn Tyr Leu Asn Trp Tyr Gln Gln
                325                 330                 335

Lys Pro Gly Lys Ala Pro Lys Leu Leu Ile Tyr Tyr Thr Ser Arg Leu
            340                 345                 350

Glu Ser Gly Val Pro Ser Arg Phe Ser Gly Ser Gly Ser Gly Thr Asp
            355                 360                 365

Tyr Thr Leu Thr Ile Ser Ser Leu Gln Pro Glu Asp Phe Ala Thr Tyr
            370                 375                 380

Tyr Cys Gln Gln Gly Asn Thr Leu Pro Trp Thr Phe Gly Gln Gly Thr
385                 390                 395                 400

Lys Val Glu Ile Lys Gly Gly Gly Gly Ser Gly Gly Gly Gly Ser Gly
                405                 410                 415

Gly Gly Gly Ser Glu Val Gln Leu Val Glu Ser Gly Gly Gly Leu Val
            420                 425                 430

Gln Pro Gly Gly Ser Leu Arg Leu Ser Cys Ala Ala Ser Gly Tyr Ser
            435                 440                 445

Phe Thr Gly Tyr Thr Met Asn Trp Val Arg Gln Ala Pro Gly Lys Gly
450                 455                 460

Leu Glu Trp Val Ala Leu Ile Asn Pro Tyr Lys Gly Val Ser Thr Tyr
465                 470                 475                 480

Asn Gln Lys Phe Lys Asp Arg Phe Thr Ile Ser Val Asp Lys Ser Lys
                485                 490                 495

Asn Thr Ala Tyr Leu Gln Met Asn Ser Leu Arg Ala Glu Asp Thr Ala
            500                 505                 510

Val Tyr Tyr Cys Ala Arg Ser Gly Tyr Tyr Gly Asp Ser Asp Trp Tyr
            515                 520                 525

Phe Asp Val Trp Gly Gln Gly Thr Leu Val Thr Val Ser Ser Thr Ser

-continued

```
                530                 535                 540
Gly Gly Gly Gly Ser Leu Glu Ser Gly Gln Val Leu Leu Glu Ser Asn
545                 550                 555                 560

Ile Lys Val Leu Pro Thr Trp Ser Thr Pro Val Gln Pro Met Ala Leu
                565                 570                 575

Ile Val Leu Gly Gly Val Ala Gly Leu Leu Leu Phe Ile Gly Leu Gly
                580                 585                 590

Ile Phe Phe Cys Val Arg Cys Arg His Arg Arg Arg Gln Ala Glu Arg
                595                 600                 605

Met Ser Gln Ile Lys Arg Leu Leu Ser Glu Lys Lys Thr Cys Gln Cys
                610                 615                 620

Pro His Arg Phe Gln Lys Thr Cys Ser Pro Ile
625                 630                 635
```